US011026904B2

(12) United States Patent
Dorn, II

(10) Patent No.: US 11,026,904 B2
(45) Date of Patent: *Jun. 8, 2021

(54) MITOFUSIN ACTIVATORS AND METHODS OF USE THEREOF

(71) Applicant: MITOCHONDRIA EMOTION, INC., Hamilton, OH (US)

(72) Inventor: Gerald W. Dorn, II, Hamilton, OH (US)

(73) Assignee: Mitochondria Emotion, Inc., Hamilton, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/087,971

(22) Filed: Nov. 3, 2020

(65) Prior Publication Data
US 2021/0046028 A1 Feb. 18, 2021

Related U.S. Application Data

(63) Continuation of application No. 16/935,489, filed on Jul. 22, 2020, which is a continuation-in-part of application No. PCT/US2019/046356, filed on Aug. 13, 2019.

(60) Provisional application No. 62/797,513, filed on Jan. 28, 2019.

(51) Int. Cl.
*A61K 31/17* (2006.01)
*A61K 31/165* (2006.01)
*A61K 31/351* (2006.01)

(52) U.S. Cl.
CPC ............ *A61K 31/17* (2013.01); *A61K 31/165* (2013.01); *A61K 31/351* (2013.01)

(58) Field of Classification Search
CPC ..... A61K 31/17; A61K 31/351; A61K 31/165
See application file for complete search history.

(56) References Cited

U.S. PATENT DOCUMENTS

| | | |
|---|---|---|
| 4,438,130 A | 3/1984 | Kaplan |
| 4,463,013 A | 7/1984 | Collins et al. |
| 4,466,977 A | 8/1984 | McMillan et al. |
| 4,588,591 A | 5/1986 | Kaplan et al. |
| 4,618,621 A | 10/1986 | Tang |
| 4,632,935 A | 12/1986 | Kaplan |
| 4,656,182 A | 4/1987 | Horwell |
| 4,677,122 A | 6/1987 | Horwell |
| 4,737,493 A | 4/1988 | Horwell |
| 4,801,604 A | 1/1989 | Vonvoigtlander et al. |
| 4,855,316 A | 8/1989 | Horwell et al. |
| 5,051,428 A | 9/1991 | Horwell et al. |
| 5,063,242 A | 11/1991 | Horwell et al. |
| 5,366,987 A | 11/1994 | Lee et al. |
| 5,721,276 A | 2/1998 | Lesieur et al. |
| 6,127,159 A | 10/2000 | Fuller et al. |
| 6,284,507 B1 | 9/2001 | Fuller et al. |
| 6,417,177 B1 * | 7/2002 | Nelson ................ A61K 31/47 514/82 |
| 6,953,680 B2 | 10/2005 | Fuller et al. |
| 7,662,910 B2 | 2/2010 | Hammock et al. |
| 7,727,717 B2 | 6/2010 | Vance et al. |
| 7,989,500 B2 | 8/2011 | Bhat et al. |
| 8,206,922 B2 | 6/2012 | Vance et al. |
| 8,226,928 B1 | 7/2012 | Sung et al. |
| 8,354,094 B1 | 1/2013 | Sung et al. |
| 8,361,439 B1 | 1/2013 | Sung et al. |
| 8,466,140 B2 | 6/2013 | Altieri et al. |
| 8,574,544 B1 | 11/2013 | Sung et al. |
| 8,604,244 B2 | 12/2013 | Bhat et al. |
| 8,791,069 B1 | 7/2014 | Sung et al. |
| 8,975,020 B2 | 3/2015 | Vance et al. |
| 9,238,625 B2 | 1/2016 | Bhat et al. |
| 9,296,681 B2 | 3/2016 | Bhat et al. |
| 9,388,156 B2 | 7/2016 | Blaauw et al. |
| 9,603,890 B2 | 3/2017 | Mann |
| 9,708,411 B2 | 7/2017 | Shi |
| 9,987,294 B2 | 6/2018 | Altieri et al. |
| 10,059,748 B2 | 8/2018 | Dunia et al. |
| 10,113,163 B2 | 10/2018 | Liu et al. |
| 10,119,142 B2 | 11/2018 | Choi et al. |
| 10,143,719 B2 | 12/2018 | Qi |
| 10,245,297 B2 | 4/2019 | Mochly-Rosen et al. |
| 10,301,356 B2 | 5/2019 | Hakansson |
| 10,485,782 B2 | 11/2019 | Rinsch et al. |

(Continued)

FOREIGN PATENT DOCUMENTS

| | | |
|---|---|---|
| FR | 2617164 A1 | 12/1988 |
| WO | 2004074482 A1 | 9/2004 |

(Continued)

OTHER PUBLICATIONS

PubChem CID 3379738, create date: Sep. 8, 2005, 10 pp.
PubChem CID 4219375, create date: Sep. 13, 2005, 11 pp.
PubChem CID 4193377, create date: Sep. 13, 2005, 10 pp.
PubChem CID 109013974, create date: Jan. 15, 2016, 8 pp.
PubChem CID 5051687, create date: Sep. 18, 2005, 8 pp.
PubChem CID 4228546, create date: Sep. 13, 2005, 9 pp.
PubChem CID 1565360, create date: Jul. 11, 2005, 10 pp.
PubChem CID 5051690, create date: Sep. 18, 2005, 9 pp.
PubChem CID 5164287, create date: Sep. 26, 2005, 9 pp.
PubChem CID 249951, create date: Mar. 26, 2005, 9 pp.
Pubchem 249951 deposited Mar. 26, 2005 (Mar. 26, 2005) p. 1-9. p. 2.

(Continued)

*Primary Examiner* — Sahar Javanmard
(74) *Attorney, Agent, or Firm* — Vorys, Sater, Seymour and Pease LLP

(57) ABSTRACT

Compositions including small molecule mitofusin activators are described. The mitofusin activators are useful for treating diseases or disorders associated with a mitochondria-associated disease, disorder, or condition such as diseases or disorders associated with mitofusin 1 (MFN1) and/or mitofusin 2 (MFN2), or mitochondrial dysfunction. Methods of treatment, pharmaceutical formulations, and screening methods for identifying compounds that activate mitochondrial fusion are also described.

21 Claims, 10 Drawing Sheets

(56) References Cited

U.S. PATENT DOCUMENTS

| | | |
|---|---|---|
| 10,494,611 B2 | 12/2019 | Cho et al. |
| 10,526,418 B2 | 1/2020 | Shi |
| 10,578,610 B2 | 3/2020 | Mochly-Rosen et al. |
| 10,617,664 B2 | 4/2020 | Pahan et al. |
| 10,640,498 B2 | 5/2020 | Gibson et al. |
| 10,709,724 B2 | 7/2020 | Alvarez et al. |
| 10,723,737 B2 | 7/2020 | Hertz et al. |
| 10,744,178 B2 | 8/2020 | Wilson |
| 10,815,211 B2 | 10/2020 | Beyrath et al. |
| 10,844,023 B2 | 11/2020 | Dorn et al. |
| 2004/0152715 A1 | 8/2004 | Kawai et al. |
| 2011/0256565 A1 | 10/2011 | Schon et al. |
| 2011/0268722 A1 | 11/2011 | Siegelin et al. |
| 2011/0275670 A1 | 11/2011 | Chapman et al. |
| 2012/0164243 A1 | 6/2012 | Rinsch et al. |
| 2012/0277286 A1 | 11/2012 | Youle et al. |
| 2014/0011890 A1 | 1/2014 | Milbrandt et al. |
| 2014/0065099 A1 | 3/2014 | Alvarez et al. |
| 2014/0142121 A1 | 5/2014 | Alfieri et al. |
| 2015/0132760 A1 | 5/2015 | Vance et al. |
| 2015/0168379 A1 | 6/2015 | Luo et al. |
| 2016/0030517 A1 | 2/2016 | Morrison et al. |
| 2016/0213643 A1 | 7/2016 | Rinsch et al. |
| 2017/0027957 A1 | 2/2017 | Fernyhough et al. |
| 2017/0180276 A1 | 6/2017 | Gershony et al. |
| 2017/0274046 A1 | 9/2017 | Morrison et al. |
| 2018/0015057 A1 | 1/2018 | Evans et al. |
| 2018/0015098 A1 | 1/2018 | Lichenstein et al. |
| 2018/0028520 A1 | 2/2018 | Henderson et al. |
| 2018/0080926 A1 | 3/2018 | Mochly-Rosen et al. |
| 2018/0085391 A1 | 3/2018 | Bouchon et al. |
| 2018/0147252 A1 | 5/2018 | Mochly-Rosen et al. |
| 2018/0305328 A1 | 10/2018 | Beyrath et al. |
| 2018/0371007 A1 | 12/2018 | Moghadam |
| 2019/0086429 A1 | 3/2019 | Nagele |
| 2019/0091291 A1 | 3/2019 | Sue et al. |
| 2019/0169158 A1 | 6/2019 | Springer et al. |
| 2019/0204342 A1 | 7/2019 | Canto Alvarez et al. |
| 2019/0262308 A1 | 8/2019 | Kolliputi et al. |
| 2019/0328758 A1 | 10/2019 | Alvarez et al. |
| 2019/0374558 A1 | 12/2019 | Reddy et al. |
| 2020/0054718 A1 | 2/2020 | Milane |
| 2020/0109136 A1 | 4/2020 | Shi et al. |
| 2020/0172518 A1 | 6/2020 | Stockley et al. |
| 2020/0231542 A1 | 7/2020 | Kemp et al. |
| 2020/0246429 A1 | 8/2020 | Sue et al. |
| 2020/0261469 A1 | 8/2020 | Gavathiotis et al. |
| 2020/0281899 A1 | 9/2020 | Dorn, II |

FOREIGN PATENT DOCUMENTS

| | | |
|---|---|---|
| WO | 2009114700 A1 | 9/2009 |
| WO | 2016054083 A1 | 4/2016 |
| WO | 2016115632 A1 | 7/2016 |
| WO | 2018013811 A1 | 1/2018 |
| WO | 2018/200323 A1 | 11/2018 |
| WO | 2019067771 A1 | 4/2019 |
| WO | 2019068865 A1 | 4/2019 |
| WO | 2019202162 A1 | 10/2019 |
| WO | 2019229133 A1 | 12/2019 |
| WO | 2019234664 A1 | 12/2019 |
| WO | 2020030954 A1 | 2/2020 |
| WO | 2020112565 A1 | 6/2020 |

OTHER PUBLICATIONS

Huang et al. 'A Quantitative Assay for Mitochondrial Fusion Using Renilla Luciferase Complementation', Mitochondrion, 2010, vol. 10, pp. 559-566. p. 560, col. 2, pare 1; col. 2, para 3-5.

Cassidy-Stone et al. 'Chemical Inhibition of the Mitochondrial Division Dynamin Reveals Its Role in Bax/Bak-dependent Mitochondrial Outer Membrane Permeabilization', Developmental Cell, 2008, vol. 14, pp. 193-204. p. 194, col. 2, para 3; p. 195, Figure 1.

PubChem CID: 43476810 Create Date: Jul. 21, 2009 (Jul. 21, 2009) pp. 1-7; p. 2, structure.

Rocha et al. 'MFN2 agonists reverse mitochondrial defects in preclinical models of Charcot-Marie-Tooth disease type 2A', Science, Apr. 20, 2018, vol. 360, pp. 336-341 [pp. 1-6). p. 3, Fig.2; p. 5, Fig.4; p. 5, col. 1, para 2 to p. 6, col. 1, para 1.

Pubchem—CID; 67977602 Create Date: Nov. 30, 2012 (Nov. 30, 2012) pp. 1-8; p. 2, structure.

Pubchem—CID: 78971265 Create Date: Oct. 19, 2014 (Oct. 19, 2014) pp. 1-8; p. 2, structure.

International Search Report and Written Opinion for PCT/US2019/046356 dated Dec. 13, 2019.

International Search Report and Written Opinion for PCT/US2020/014784 dated Apr. 14, 2020.

* cited by examiner

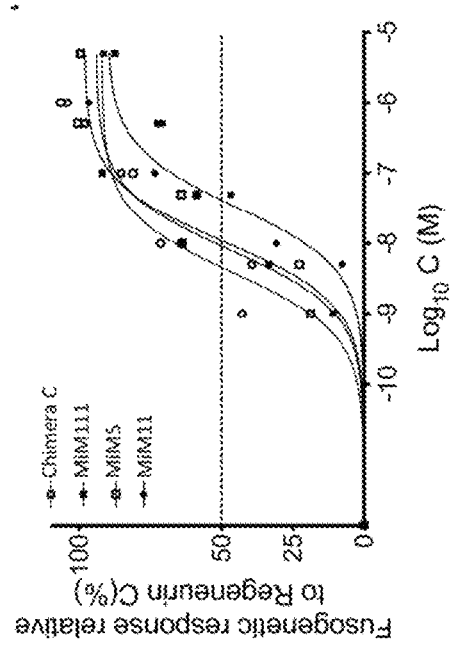
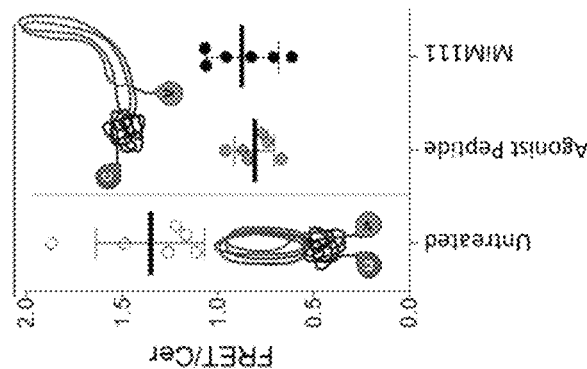
FIG. 6A
FIG. 6B

MITOFUSIN ACTIVATORS AND METHODS OF USE THEREOF

CROSS-REFERENCE TO RELATED APPLICATIONS

The present application is a continuation of U.S. patent application Ser. No. 16/935,489, filed on Jul. 22, 2020, which is a continuation-in-part of International Patent Application PCT/US2019/046356, filed on Aug. 13, 2019, which claims the benefit of priority under 35 U.S.C. § 119 from U.S. Provisional Patent Application 62/797,513, filed on Jan. 28, 2019, each of which is incorporated herein by reference in its entirety.

FIELD OF THE INVENTION

The present disclosure generally relates to compositions and methods for treating genetic and traumatic neurodegenerative diseases, disorders, or conditions. Also provided are methods for high-throughput screening of compositions.

SUMMARY

Among the various aspects of the present disclosure is the provision of novel chemical classes of small molecule mitofusin activators and methods of use thereof.

One aspect of the present disclosure provides for methods of treating neurodegenerative diseases, disorders, or conditions. In some features, the method comprises administering to a subject a therapeutically effective amount of a composition of one or more mitofusin activators or pharmaceutically acceptable salts thereof; the mitofusin activators stimulate mitochondrial fusion and subcellular mitochondrial transport.

Another aspect of the present disclosure provides for a method of activating mitofusin in a subject in need thereof. In some features, the method comprises administering to a subject a composition of one or more mitofusin activators or pharmaceutically acceptable salts thereof; the mitofusin activator stimulates mitochondrial fusion and subcellular transport; the subject has a genetic or traumatic neurodegenerative disease, disorder, or condition; the mitofusin activator is not a compound selected from the following compounds:

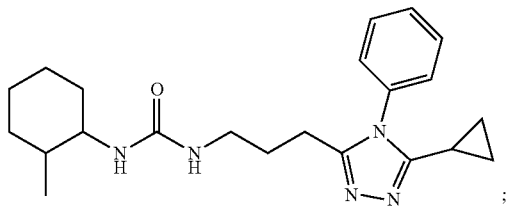

1-(3-(5-cyclopropyl-4-phenyl-4H-1,2,4-triazol-3-yl)propyl)-3-(2-methylcyclohexyl)urea

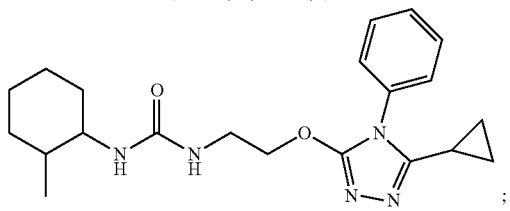

1-(2-((5-cyclopropyl-4-phenyl-4H-1,2,4-triazol-3-yl)oxy)ethyl)-3-(2-methylcyclohexyl)urea

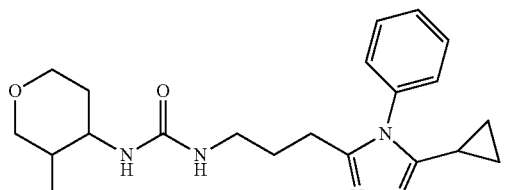

1-(3-(5-cyclopropyl-4-phenyl-4H-1,2,4-triazol-3-yl)propyl)-3-(tetrahydro-2H-pyran-4-yl)urea

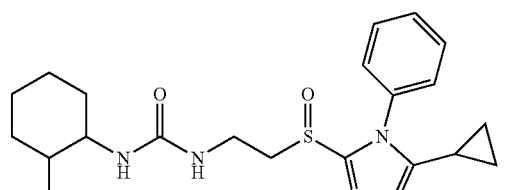

1-(2-((5-cyclopropyl-4-phenyl-4H-1,2,4-triazol-3-yl)sulfinyl)ethyl)-3-(2-methylcyclohexyl)urea

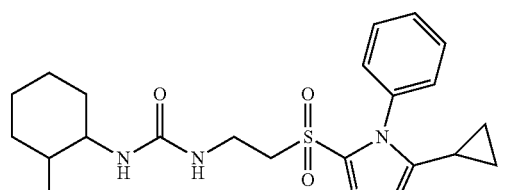

1-(2-((5-cyclopropyl-4-phenyl-4H-1,2,4-triazol-3-yl)sulfonyl)ethyl)-3-(2-methylcyclohexyl)urea

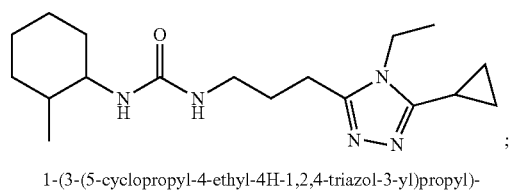

1-(3-(5-cyclopropyl-4-ethyl-4H-1,2,4-triazol-3-yl)propyl)-3-(2-methylcyclohexyl)urea

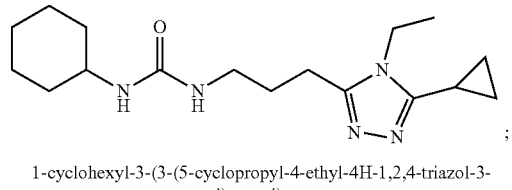

1-cyclohexyl-3-(3-(5-cyclopropyl-4-ethyl-4H-1,2,4-triazol-3-yl)propyl)urea

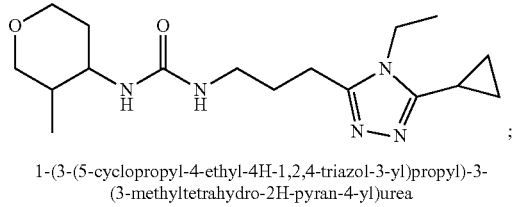

1-(3-(5-cyclopropyl-4-ethyl-4H-1,2,4-triazol-3-yl)propyl)-3-(3-methyltetrahydro-2H-pyran-4-yl)urea

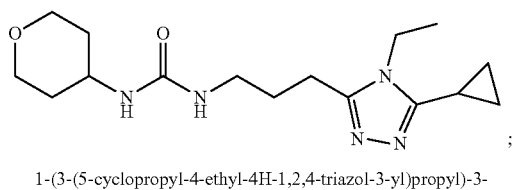

1-(3-(5-cyclopropyl-4-ethyl-4H-1,2,4-triazol-3-yl)propyl)-3-(tetrahydro-2H-pyran-4-yl)urea

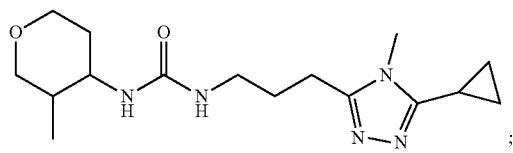

1-(3-(5-cyclopropyl-4-methyl-4H-1,2,4-triazol-3-yl)propyl)-3-
(3-methyltetrahydro-2H-pyran-4-yl)urea

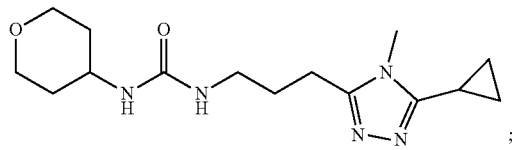

1-(3-(5-cyclopropyl-4-methyl-4H-1,2,4-triazol-3-yl)propyl)-3-
(tetrahydro-2H-pyran-4-yl)urea

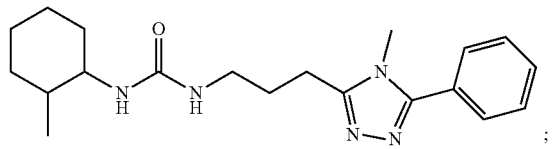

1-(3-(4-methyl-5-phenyl-4H-1,2,4-triazol-3-yl)propyl)-3-
(2-methylcyclohexyl)urea

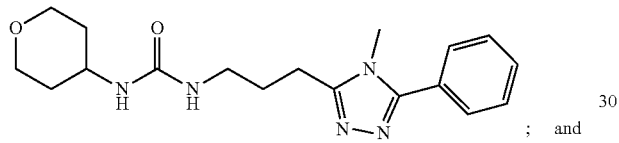

1-(3-(4-methyl-5-phenyl-4H-1,2,4-triazol-3-yl)propyl)-3-
(tetrahydro-2H-pyran-4-yl)urea ; and

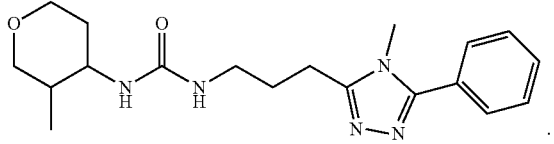

1-(3-(4-methyl-5-phenyl-4H-1,2,4-triazol-3-yl)propyl)-3-
(3-methyltetrahydro-2H-pyran-4-yl)urea

.

Another aspect of the present disclosure provides for methods of enhancing damaged nerve repair or regeneration in a subject in need thereof. In some features, the method comprises administering to a subject a composition comprising one or more mitofusin activators or pharmaceutically acceptable salts thereof; the mitofusin activator regulates mitochondrial fusion and subcellular transport; the subject has genetic neurodegeneration or traumatic nerve injury; the mitofusin activator is not a compound selected from the following compounds:

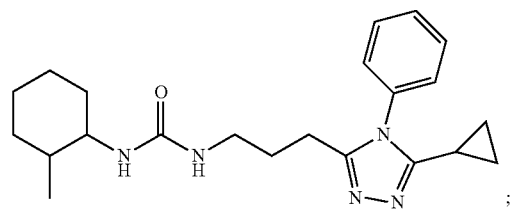

1-(3-(5-cyclopropyl-4-phenyl-4H-1,2,4-triazol-3-yl)propyl)-
3-(2-methylcyclohexyl)urea

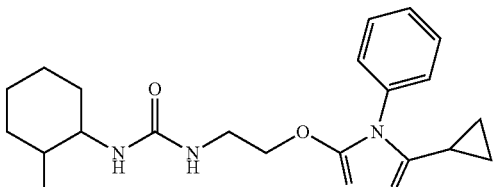

1-(2-((5-cyclopropyl-4-phenyl-4H-1,2,4-triazol-3-yl)oxy)ethyl)-
3-(2-methylcyclohexyl)urea

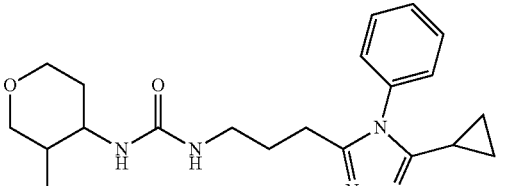

1-(3-(5-cyclopropyl-4-phenyl-4H-1,2,4-triazol-3-yl)propyl)-3-
(tetrahydro-2H-pyran-4-yl)urea

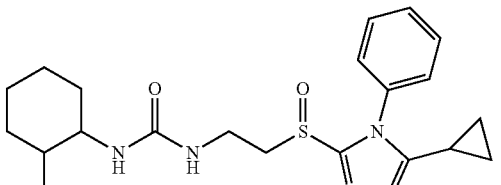

1-(2-((5-cyclopropyl-4-phenyl-4H-1,2,4-triazol-3-
yl)sulfinyl)ethyl)-3-(2-methylcyclohexyl)urea

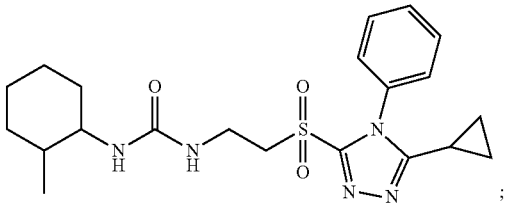

1-(2-((5-cyclopropyl-4-phenyl-4H-1,2,4-triazol-3-
yl)sulfonyl)ethyl)-3-(2-methylcyclohexyl)urea

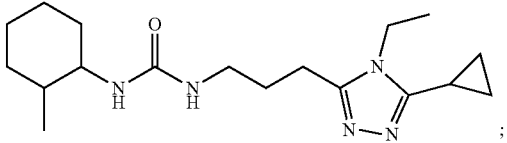

1-(3-(5-cyclopropyl-4-ethyl-4H-1,2,4-triazol-3-yl)propyl)-
3-(2-methylcyclohexyl)urea

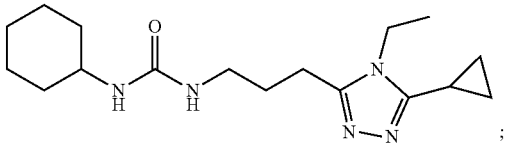

1-cyclohexyl-3-(3-(5-cyclopropyl-4-ethyl-4H-1,2,4-triazol-3-
yl)propyl)urea

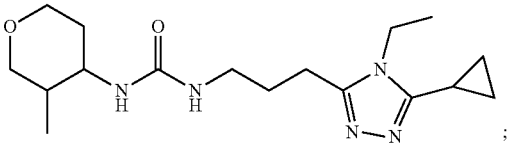

1-(3-(5-cyclopropyl-4-ethyl-4H-1,2,4-triazol-3-yl)propyl)-3-
(3-methyltetrahydro-2H-pyran-4-yl)urea

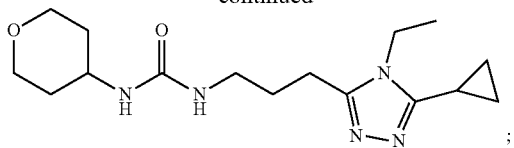

1-(3-(5-cyclopropyl-4-ethyl-4H-1,2,4-triazol-3-yl)propyl)-3-(tetrahydro-2H-pyran-4-yl)urea

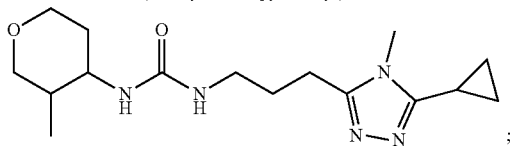

1-(3-(5-cyclopropyl-4-methyl-4H-1,2,4-triazol-3-yl)propyl)-3-(3-methyltetrahydro-2H-pyran-4-yl)urea

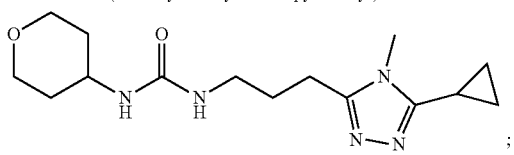

1-(3-(5-cyclopropyl-4-methyl-4H-1,2,4-triazol-3-yl)propyl)-3-(tetrahydro-2H-pyran-4-yl)urea

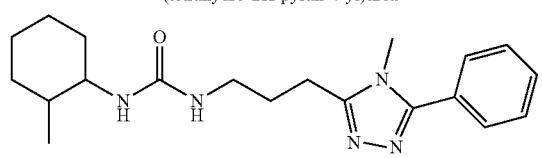

1-(3-(4-methyl-5-phenyl-4H-1,2,4-triazol-3-yl)propyl)-3-(2-methylcyclohexyl)urea

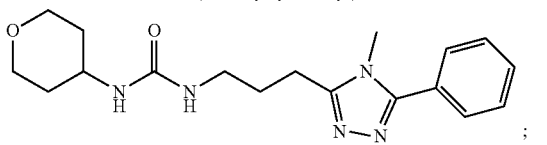

1-(3-(4-methyl-5-phenyl-4H-1,2,4-triazol-3-yl)propyl)-3-(tetrahydro-2H-pyran-4-yl)urea ; and

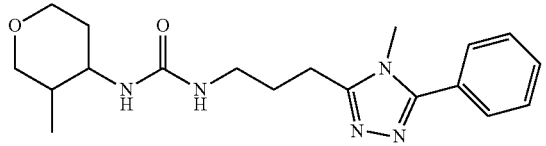

1-(3-(4-methyl-5-phenyl-4H-1,2,4-triazol-3-yl)propyl)-3-(3-methyltetrahydro-2H-pyran-4-yl)urea In some aspects, the mitofusin activator: has substantially better functional potency of both 1-[2-(benzylsulfanyl)ethyl]-3-(2-methylcyclohexyl)urea (Cpd A, Rocha *Science* 2018) and 2-{2-[(5-cyclopropyl-4-phenyl-4H-1,2,4-triazol-3-yl)sulfanyl]propanamido}-4H,5H,6H-cyclopenta[b]thiophene-3-carboxamide (Cpd B, Rocha *Science* 2018); or stimulates mitofusin activity (e.g., mitochondrial fusion and subcellular transport).

In some aspects, the mitofusin activator: enhances mitochondrial transport in nerve axons; increases mitochondrial polarization; corrects cell and organ dysfunction caused by primary abnormalities in mitochondrial fission or fusion; corrects cell and organ defects in which secondary mitochondrial dysfunction is a contributing factor; reverses mitochondrial defects (e.g., dysmorphometry, clustering, loss of polarization, loss of motility); restores, activates, regulates, modulates, promotes, or enhances the fusion, function, tethering, transport, trafficking (e.g., axonal mitochondrial trafficking), mobility, or movement of mitochondria (in, optionally, a nerve or a neuron); enhances mitochondrial elongation or mitochondrial aspect ratio; disrupts intramolecular restraints in MFN2; allosterically activates MFN2; corrects mitochondrial dysfunction and cellular dysfunction; repairs defects in neurons with mitochondrial mutations; or targets MFN1 or MFN2.

In some aspects, the mitofusin activator comprises one or more compounds having structures represented by formulas (I) or (II):

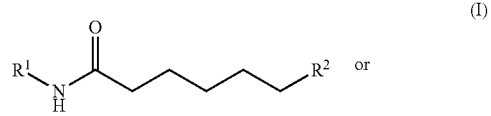

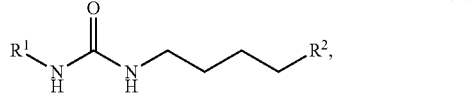

or a pharmaceutically acceptable salt, tautomer, or stereoisomer thereof wherein $R^1$ is a non-, mono-, or poly-substituted aryl, $C_{3-8}$ cycloalkyl, $C_{3-8}$ heteroaryl, or $C_{3-8}$ heterocyclyl, and $R^2$ is a non-, mono-, or poly-substituted aryl, $C_{3-8}$ cycloalkyl, $C_{3-8}$ heteroaryl, or $C_{3-8}$ heterocyclyl.

In some aspects, the mitofusin activator is selected from a compound having a structure represented by formulas (I) or (II)

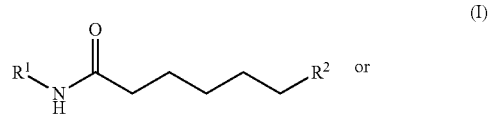

wherein $R^1$ is selected from the following moieties:

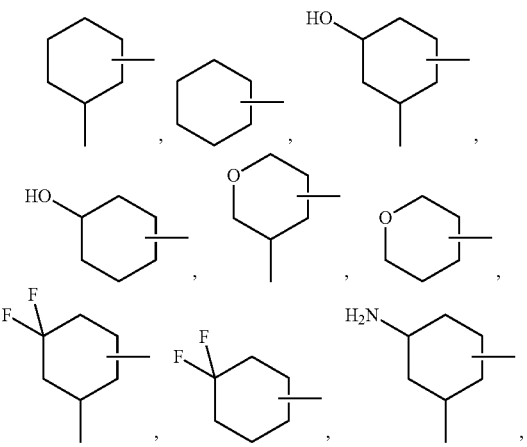

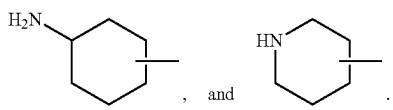, and and $R^2$ is selected from the following moieties:

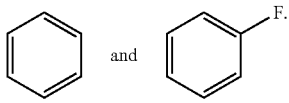 [SMILES: c1ccccc1 ; Fc1ccccc1]

In some aspects, $R^1$ and $R^2$ are optionally substituted by one or more of: acetamide, $C_{1-8}$ alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene; and optionally further substituted with one or more acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene. Optionally the aforementioned alkyl, cycloalkyl, heteroaryl, heterocyclyl, indole, or phenyl is further substituted with one or more of the following: acetamide, alkoxy, amino, azo, Br, $C_{1-8}$alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene.

In some aspects, the compound is selected from the following moieties:

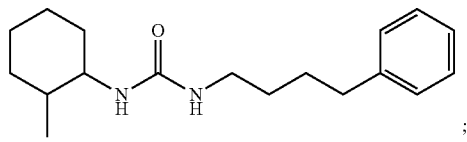

1-(2-methylcyclohexyl)-3-(4-phenylbutyl)urea

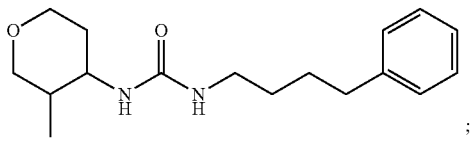

1-(3-methyltetrahydro-2H-pyran-4yl)-3-(4-phenylbutyl)urea

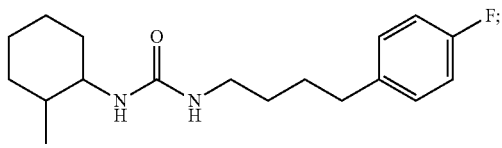

1-(4-(4-fluorophenyl)butyl)-3-(2-methylcyclohexyl)urea

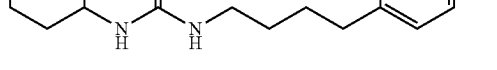

1-(4,4-difluoro-2-methylcyclohexyl)-3-(4-phenylbutyl)urea

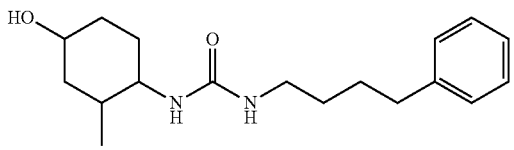

1-(4-hydroxy-2-methylcyclohexyl)-3-(4-phenylbutyl)urea

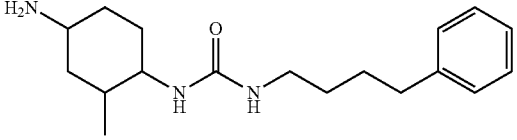

1-(4-amino-2-methylcyclohexyl)-3-(4-phenylbutyl)urea

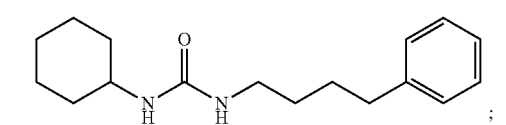

1-cyclohexyl-3-(4-phenylbutyl)urea

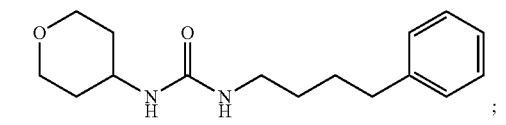

1-(4-phenylbutyl)-3-(tetrahydro-2H-pyran-4-yl)urea

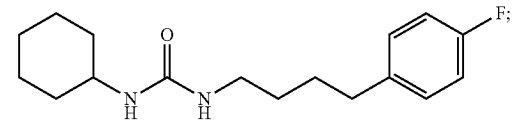

1-cyclohexyl-3-(4-(4-fluorophenyl)butyl)urea

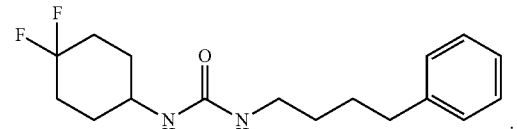

1-(4,4-difluorocyclohexyl)-3-(4-phenylbutyl)urea

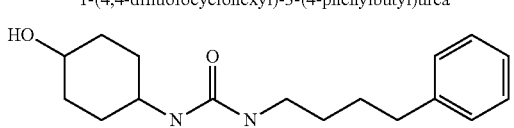

1-(4-hydroxycyclohexyl)-3-(4-phenylbutyl)urea

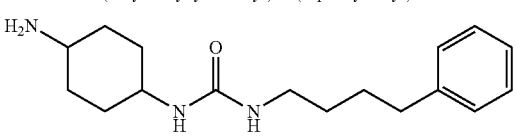

1-(4-aminocyclohexyl)-3-(4-phenylbutyl)urea

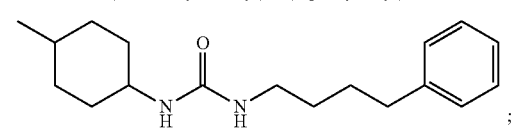

1-(4-methylcyclohexyl)-3-(4-phenylbutyl)urea

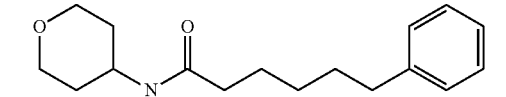

6-phenyl-N-(tetrahydro-2H-pyran-4-yl)hexanamide

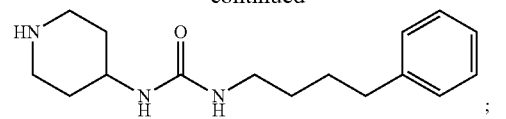

1-(4-phenylbutyl)-3-(piperidin-4-yl)urea

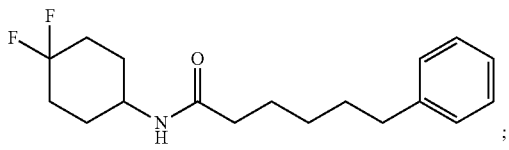

N-(4,4-difluorocyclohexyl)-6-phenylhexanamide

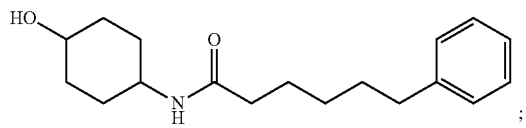

N-(4-hydroxycyclohexyl)-6-phenylhexanamide

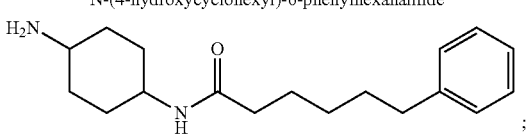

N-(4-aminocyclohexyl)-6-phenylhexanamide

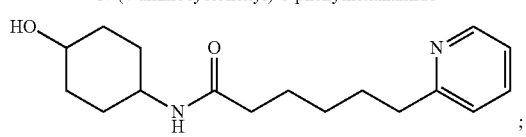

N-(4-hydroxycyclohexyl)-6-(pyridin-2-yl)hexanamide

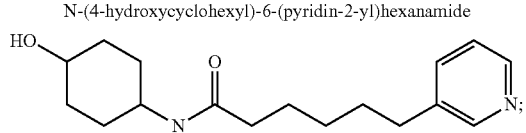

N-(4-hydroxycyclohexyl)-6-(pyridin-3-yl)hexanamide

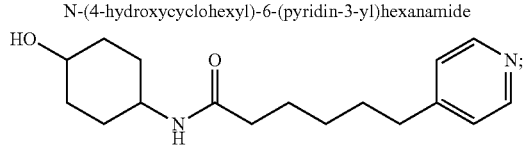

N-(4-hydroxycyclohexyl)-6-(pyridin-4-yl)hexanamide

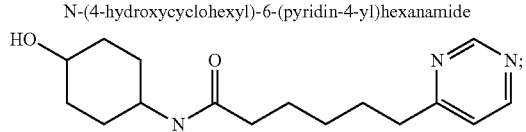

N-(4-hydroxycyclohexyl)-6-(pyrimidin-4-yl)hexanamide

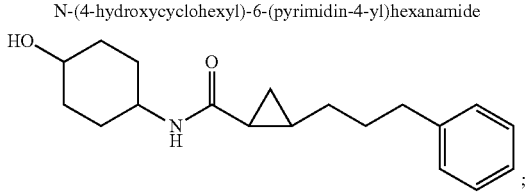

N-(4-hydroxycyclohexyl)-2-(3-phenylpropyl)cyclopropane-1-carboxamide

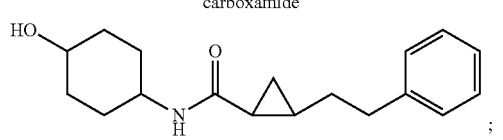

N-(4-hydroxycyclohexyl)-2-phenethylcyclopropane-1-carboxamide

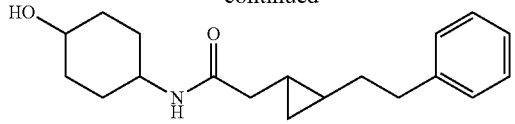

N-(4-hydroxycyclohexyl)-2-(2-phenethylcyclopropyl)acetamide

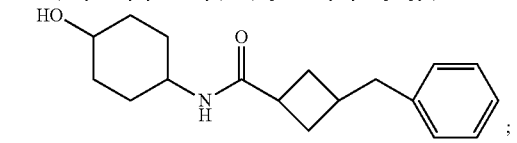

3-benzyl-N-(4-hydroxycyclohexyl)cyclobutane-1-carboxamide

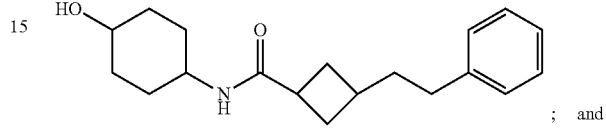

; and

N-(4-hydroxycyclohexyl)-3-phenethylcyclobutane-1-carboxamide

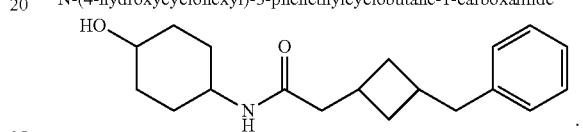

2-(3-benzylcyclobutyl)-N-(4-hydroxycyclohexyl)acetamide

Yet another aspect of present disclosure provides for a pharmaceutical composition comprising a mitofusin activator, optionally in combination with one or more therapeutically acceptable diluents or carriers.

In some aspects, the pharmaceutical composition comprises a pharmaceutically acceptable excipient.

In some aspects, the pharmaceutical composition comprises at least one compound selected from neuroprotectants, anti-Parkinsonian drugs, amyloid protein deposition inhibitors, beta amyloid synthesis inhibitors, antidepressants, anxiolytic drugs, antipsychotic drugs, anti-amyotrophic lateral sclerosis drugs, anti-Huntington's drugs, anti-Alzheimer's drugs, anti-epileptic drugs, and/or steroids.

Yet another aspect of the present disclosure provides for a method of treating a mitochondria-associated disease, disorder, or condition in a subject, the method comprising administering to the subject a therapeutically effective amount of a mitofusin activator.

In some aspects, the subject is diagnosed with or is suspected of having a mitochondria-associated disease, disorder, or condition. In some aspects, the mitochondria-associated disease, disorder, or condition is one or more of: a central nervous system (CNS) or peripheral nervous system (PNS) injury or trauma, such as trauma to the CNS or PNS, crush injury, spinal cord injury (SCI), traumatic brain injury, stroke, optic nerve injury, or related conditions that involve axonal disconnection; a chronic neurodegenerative condition wherein mitochondrial fusion, fitness, or trafficking are impaired; a disease or disorder associated with mitofusin 1 (MFN1) or mitofusin 2 (MFN2) or mitochondrial dysfunction, fragmentation, or fusion; dysfunction in MFN1 or MFN2 unfolding; mitochondria dysfunction caused by mutations; a degenerative neurological condition, such as Alzheimer's disease, Parkinson's disease, Charcot-Marie-Tooth disease, or Huntington's disease; hereditary motor and sensory neuropathy, autism, autosomal dominant optic atrophy (ADOA), muscular dystrophy, Lou Gehrig's disease, cancer, mitochondrial myopathy, diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), mtDNA depletion, mitochondrial neurogastrointestinal encephalomyopathy (MNGIE), dysautonomic mitochondrial myopathy, mitochondrial channelopathy, and/or pyruvate dehydrogenase complex deficiency (PDCD/PDH).

Other objects and features will be in part apparent and in part pointed out hereinafter.

DESCRIPTION OF THE DRAWINGS

Those of skill in the art will understand that the drawings, described below are for illustrative purposes only. The drawings are not intended to limit the scope of the present teachings in any way.

FIG. 6A shows the dose-response relations of MiM5, MiM11, and MiM111 compared to a prototype Chimera compound described in Rocha et al *Science* 2018; FIG. 6B shows MiM111 conformational opening of MFN 2 mimics that of an agonist peptide described in Franco et al *Nature* 2016.

DETAILED DESCRIPTION

Figure 1:
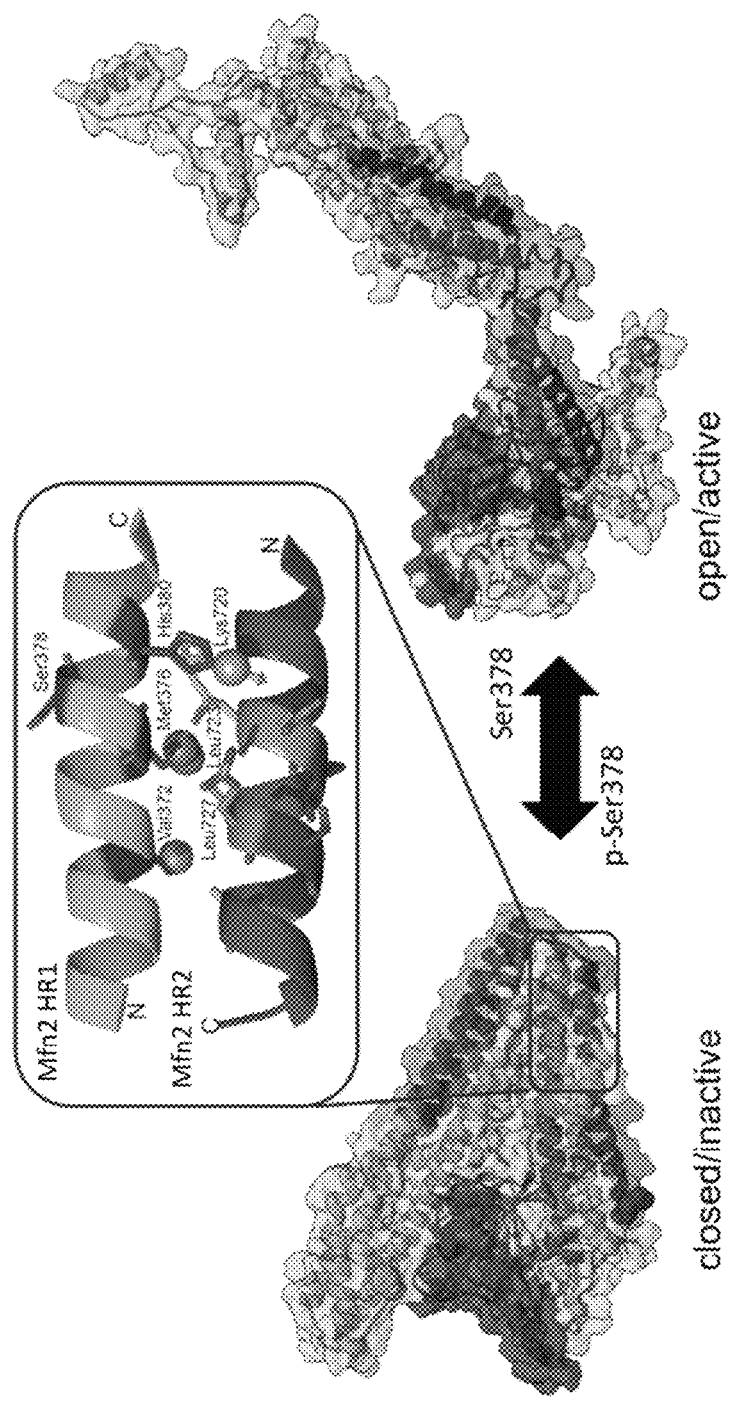
FIG. 1 illustrates a structural model of human MFN2 in the closed/inactive (left) and open/active conformation (right) that is promoted by mitofusin activators.

The present disclosure is based, at least in part, on the discovery that pharmacophore modeling of function-critical MFN2-derived interacting peptides may produce small molecule peptidomimetic activators useful to treat mitochondrial-associated diseases, disorders, and conditions. As shown herein, the present disclosure provides new chemical classes of compositions for regulating mitochondrial function. These compositions may be useful to correct cell and organ dysfunction caused by primary abnormalities in mitochondrial fission, fusion and subcellular motility/distribution, or in which secondary mitochondrial abnormalities contribute to disease.

Mitofusin Activators

The present disclosure provides for a new structurally-distinct class of small molecule inhibitors of a function-critical MFN2 peptide-peptide interaction. As described herein, a composition for the treatment of a mitochondria-associated disease, disorder, or condition may comprise a mitofusin activator, such as a peptidomimetic (e.g., a small-molecule that mimics the chemico-structural features of a peptide). A peptidomimetic may be a chemical peptidomimetic. For example, the peptidomimetic may mimic a mitofusin-derived mini-peptide.

As described herein, a new generation of peptidomimetic small molecules has been developed. These compounds activate mitochondrial fusion by directing MFN1 and MFN2 to different conformational states. The first small molecule peptidomimetics to target MFN1 or MFN2 (described in Rocha et al. *Science*, 2018) had poor pharmacokinetic characteristics, making them "undruggable." Described herein are members of a structurally distinct class of small molecule mitofusin activators that activate mitochondrial fusion and subcellular transport, have favorable pharmacokinetic properties, and may be used to correct mitochondrial and cellular dysfunction.

Mitofusin activators enhance mitochondrial elongation. Mitochondrial elongation may be measured by mitochondrial aspect ratio, but doing so is a time-consuming and indirect means of measuring mitofusin activator activity. Mitofusin activator activity is best measured through determining the rate of mitochondria to fuse, or to exchange contents. As described herein, a method of high-throughput assaying of small molecules, peptides, or other bioactive compounds for mitochondrial fusion may be used to screen compounds for mitofusin activator activity.

Mitofusin Mini-Peptide

As described herein, a peptide mitofusin activator may be an MFN2-derived mini-peptide as described in Franco et al. *Nature* 2016.

MFN Activator (Fusion-Promoting) Peptidomimetic

As described herein, a peptidomimetic may be a MFN activator (fusion-promoting) peptidomimetic that competes with endogenous MFN1 or MFN2 HR1-HR2 peptide-peptide interactions as described in Franco et al. *Nature* 2016 and Rocha et al. *Science* 2018.

Mitofusin activators may include the following compounds:

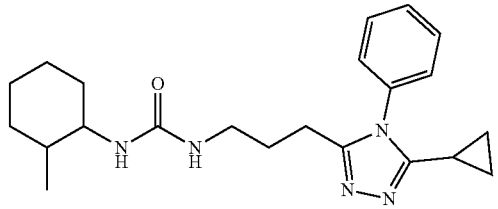

1-(3-(5-cyclopropyl-4-phenyl-4H-1,2,4-triazol-3-yl)
propyl)-3-(2-methylcyclohexyl)urea
(Chimera-C, M.W.: 381.52 g/mol, Formula: $C_{22}H_{31}N_5O$) ;

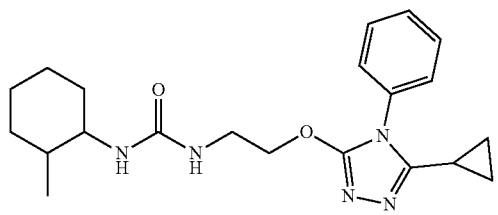

1-(2-((5-cyclopropyl-4-phenyl-4H-1,2,4-triazol-3-yl)
oxy)ethyl)-3-(2-methylcyclohexyl)urea
(Chimera-O, M.W.: 383.49 g/mol, Formula: $C_{21}H_{29}N_5O_2$) ;

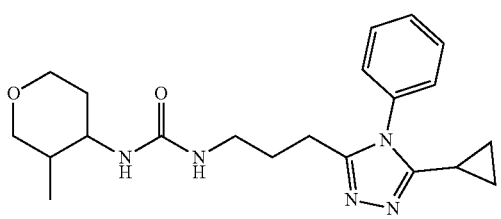

1-(3-(5-cyclopropyl-4-phenyl-4H-1,2,4-triazol-3-yl)
propyl)-3-(tetrahydro-2H-pyran-4-yl)urea
(Chimera-O, M.W.: 369.47 g/mol, Formula: $C_{20}H_{27}N_5O_2$) ;

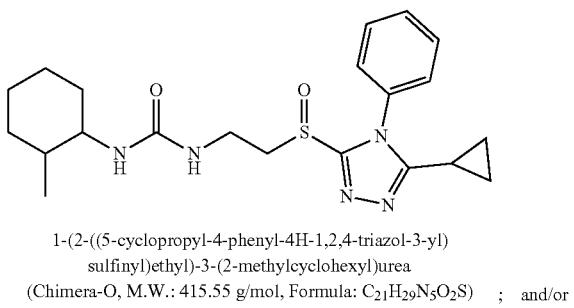

1-(2-((5-cyclopropyl-4-phenyl-4H-1,2,4-triazol-3-yl)
sulfinyl)ethyl)-3-(2-methylcyclohexyl)urea
(Chimera-O, M.W.: 415.55 g/mol, Formula: $C_{21}H_{29}N_5O_2S$) ; and/or

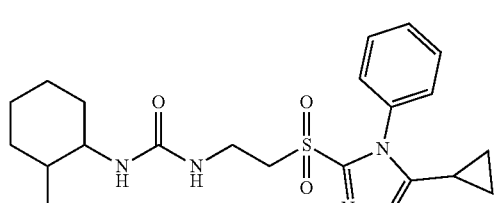

1-(2-((5-cyclopropyl-4-phenyl-4H-1,2,4-triazol-3-yl)
sulfonyl)ethyl)-3-(2-methylcyclohexyl)urea
(Chimera-O, M.W.: 431.56 g/mol, Formula: $C_{21}H_{29}N_5O_3S$) .

Mitofusin activators of the "M" class include the following compounds:

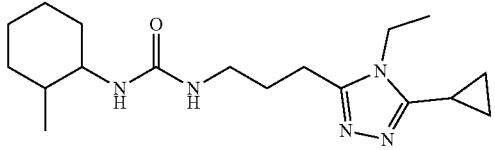

1-(3-(5-cyclopropyl-4-ethyl-4H-1,2,4-triazol-3-yl)
propyl)-3-(2-methylcyclohexyl)urea
(M-1, M.W.: 333.47 g/mol, Formula: $C_{18}H_{31}N_5O$) ;

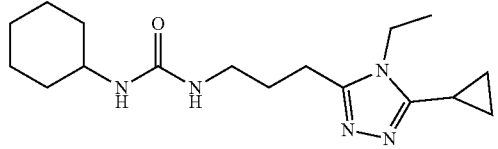

1-cyclohexyl-3-(3-(5-cyclopropyl)-4-ethyl-4H-1,2,4-triazol-3-
yl)propyl)urea (M-2, M.W.: 319.45 g/mol, Formula: $C_{17}H_{29}N_5O$) ;

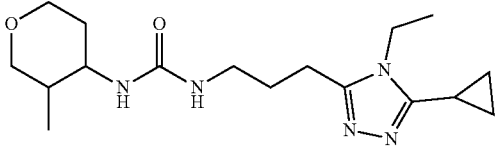

1-(3-(5-cyclopropyl-4-ethyl-4H-1,2,4-triazol-3-yl)
propyl)-3-(methyltetrahydro-2H-pyran-4-yl)urea
(M-3, M.W.: 335.45 g/mol, Formula: $C_{17}H_{29}N_5O_2$) ;

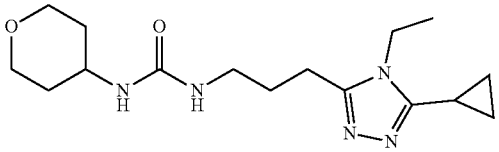

1-(3-(5-cyclopropyl-4-ethyl-4H-1,2,4-triazol-3-yl)
propyl)-3-(tetrahydro-2H-pyran-4-yl)urea
(M-4, M.W.: 321.42 g/mol, Formula: $C_{16}H_{27}N_5O_2$) ;

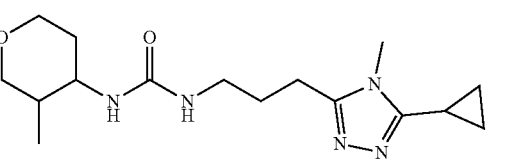

1-(3-(5-cyclopropyl-4-methyl-4H-1,2,4-triazol-3-yl)
propyl)-3-(3-methyltetrahydro-2H-pyran-4-yl)urea
(M-5, M.W.: 321.43 g/mol, Formula: $C_{16}H_{27}N_5O_2$) ; and/or

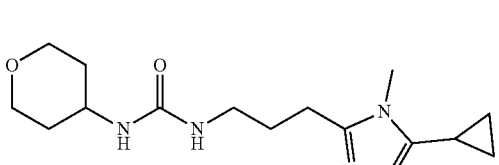

1-(3-(5-cyclopropyl-4-methyl-4H-1,2,4-triazol-3-yl)
propyl)-3-(tetrahydro-2H-pyran-4-yl)urea
(M-6, M.W.: 307.4 g/mol, Formula: $C_{15}H_{25}N_5O_2$) .

Mitofusin activators of the "F" class include the following compounds:

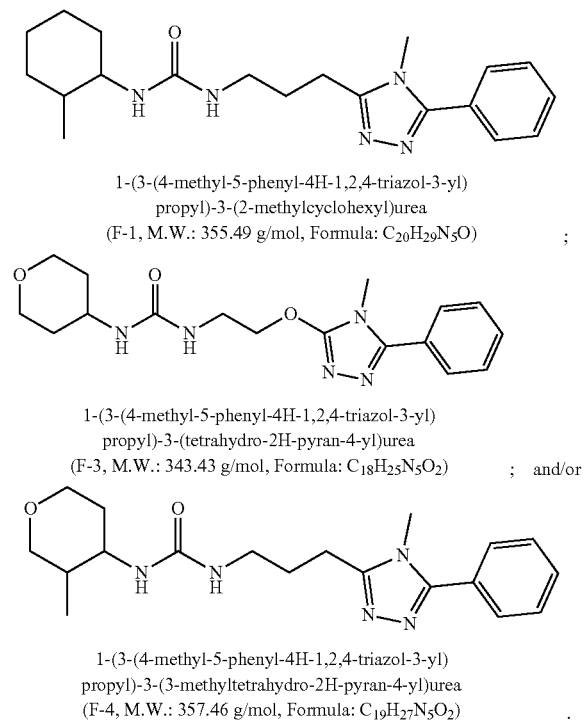

1-(3-(4-methyl-5-phenyl-4H-1,2,4-triazol-3-yl)
propyl)-3-(2-methylcyclohexyl)urea
(F-1, M.W.: 355.49 g/mol, Formula: $C_{20}H_{29}N_5O$)    ;

1-(3-(4-methyl-5-phenyl-4H-1,2,4-triazol-3-yl)
propyl)-3-(tetrahydro-2H-pyran-4-yl)urea
(F-3, M.W.: 343.43 g/mol, Formula: $C_{18}H_{25}N_5O_2$)   ; and/or 1-(3-(4-methyl-5-phenyl-4H-1,2,4-triazol-3-yl)
propyl)-3-(3-methyltetrahydro-2H-pyran-4-yl)urea
(F-4, M.W.: 357.46 g/mol, Formula: $C_{19}H_{27}N_5O_2$)   .

Mitofusin Activators: Structurally Distinct Small Molecules that Activate MFN1 and/or MFN2

The small molecule mitofusin activators described herein are allosteric mitofusin activators derived from the pharmacophore HR1-HR2 peptide-peptide interaction model described in Rocha et al. *Science* 2018, but which are structurally distinct and of separate chemical classes from those previously described. An activator is a substance that partially or fully activates the protein to which it binds.

The mitofusin activators of the present disclosure may be of the formula (I) or (II):

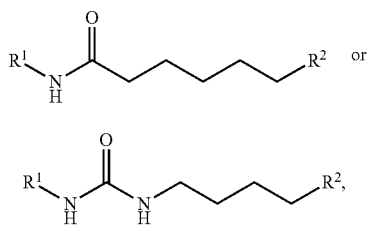

(I)

(II)

or a pharmaceutically acceptable salt, tautomer, or stereoisomer thereof, wherein $R^1$ is selected from the following moieties:

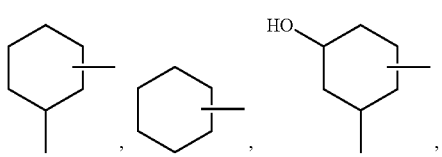

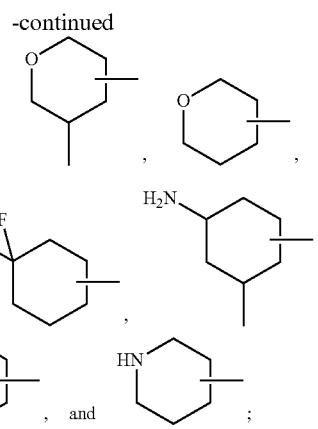

and wherein $R^2$ is selected from the following moieties:

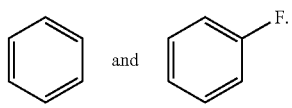 [SMILES: c1ccccc1 ; Fc1ccccc1]

Optionally, $R^1$ or $R^2$ in formula (I) or (II) may be independently substituted by one or more of the following groups: acetamide, $C_{1-8}$ alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene and optionally further substituted with acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene and the alkyl, cycloalkyl, heteroaryl, heterocyclyl, indole, or phenyl is optionally further substituted with one or more of the following groups: acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, and/or thiophene.

Optionally, the $R^1$ and $R^2$ groups in formula (I) or (II) may be independently substituted with one or more of the following groups: hydroxyl; $C_{1-10}$ alkyl hydroxyl; amine; $C_{1-10}$ carboxylic acid; $C_{1-10}$ carboxyl; straight chain or branched $C_{1-10}$ alkyl, optionally containing unsaturation; a $C_{2-8}$ cycloalkyl optionally containing unsaturation or one oxygen or nitrogen atom; straight chain or branched $C_{1-10}$ alkyl amine; heterocyclyl; heterocyclic amine; and/or aryl comprising phenyl, heteroaryl containing from one to four of the following heteroatoms: N, O, and/or S, unsubstituted phenyl ring, substituted phenyl ring, unsubstituted heterocyclyl, and substituted heterocyclyl. Optionally, the unsubstituted phenyl ring or substituted phenyl ring may be independently substituted with one or more of the following groups: hydroxyl; $C_{1-10}$ alkyl hydroxyl; amine; $C_{1-10}$ carboxylic acid; $C_{1-10}$ carboxyl; straight chain or branched $C_{1-10}$ alkyl, optionally containing unsaturation; straight chain or branched $C_{1-10}$ alkyl amine, optionally containing unsaturation; a $C_{2-10}$ cycloalkyl optionally containing unsaturation or one oxygen or nitrogen atom; straight chain or branched $C_{1-10}$ alkyl amine; heterocyclyl; heterocyclic amine; and/or aryl comprising phenyl and heteroaryl containing from one to four of the following heteroatoms: N, O, and/or S. Optionally, the unsubstituted heterocyclyl or substituted heterocyclyl may be independently substituted with one or more of the following groups: hydroxyl; $C_{1-10}$ alkyl hydroxyl; amine; $C_{1-10}$ carboxylic acid; $C_{1-10}$ carboxyl; straight chain or branched $C_{1-10}$ alkyl optionally containing unsaturation; straight chain or branched $C_{1-10}$ alkyl amine optionally containing unsaturation; a $C_{2-8}$ cycloalkyl optionally containing unsaturation or one oxygen or nitrogen atom; heterocyclyl; straight chain or branched $C_{1-10}$ alkyl amine; heterocyclic amine; and/or aryl comprising a phenyl and a heteroaryl containing from one to four of the following heteroatoms: N, O, and S. Any of the above may be further optionally substituted.

In some aspects, $R^1$ or $R^2$ in formula (I) or (II) are optionally substituted by one or more of the following groups: acetamide, alkoxy, amino, azo, Br, $C_{1-8}$ alkyl, carbonyl, carboxyl, Cl, cyano, $C_{3-8}$cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene; and optionally further substituted with one or more of the following groups: acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, or thiophene; wherein the alkyl, cycloalkyl, heteroaryl, heterocyclyl, indole, or phenyl, is optionally further substituted with one or more of acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfone, and/or thiophene.

In another aspect of the disclosure, the mitofusin activator may be of the formula (III):

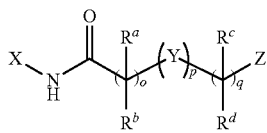

(III)

or a pharmaceutically salt thereof.

In Formula (III), o may be 0, 1, 2, 3, 4, or 5; p may be 0 or 1; and q may be 0, 1, 2, 3, 4, or 5 with the proviso that the sum of o+p+q is not less than 3 or greater than 7; X may be cycloalkyl, heterocycloalkyl, aryl, or heteroaryl; Z may be cycloalkyl, heterocycloalkyl, aryl, or heteroaryl; $R^a$ and $R^b$ may be independently H, F, alkyl, or $C_{3-7}$ cycloalkyl, or $R^a$ and $R^b$ taken together may form a $C_{3-7}$ cycloalkyl or heterocycloalkyl; $R^c$ and $R^d$ may be independently H, F, alkyl, $COR^g$, or $C_{3-7}$ cycloalkyl, or $R^c$ and $R^d$ taken together may form a $C_{3-7}$ cycloalkyl or heterocycloalkyl; Y may be O, $CR^eR^f$, $CR^g$=$CR^h$, C≡C, cycloalkyl, heterocycloalkyl, aryl, heteroaryl, $NR^g$, S, $SO_2$, $SONR^h$, $NR^hSO_2$, $NR^gCO$, $CONR^g$, or $NR^gCONR^h$; $R^e$ and $R^f$ may independently be H, F, alkyl, or cycloalkyl, or $R^e$ and $R^f$ may be taken together to form $C_{3-7}$ cycloalkyl or heterocycloalkyl; $R^g$ may be H, alkyl, or $C_{3-7}$ cycloalkyl; and $R^h$ may be H, alkyl, or $C_{3-7}$ cycloalkyl.

In some aspects, in the mitofusin activator of formula (III), o is 0, 1, 2, 3, 4, or 5; p is 0 or 1; and q is 0, 1, 2, 3, 4, or 5 with the proviso that the sum of o+p+q is not less than 3 or greater than 7; X is cycloalkyl or heterocycloalkyl; Z is cycloalkyl, heterocycloalkyl, aryl, or heteroaryl; Y is O, $CR^eR^f$, cycloalkyl, or aryl; and $R^a$, $R^b$, $R^c$, $R^d$, $R^e$, $R^f$, and $R^g$ are independently H or alkyl.

In some aspects, in the mitofusin activator of formula (III), o may be 0, 1, 2, 3, 4, or 5; p may be 0 or 1 and q may be 0, 1, 2, 3, 4, or 5 with the proviso that the sum of o+p+q is not less than 3 or greater than 5; X may be a cycloalkyl having one to three of the following substituents: $R^g$, $OR^g$, $NR^gR^h$, F, or $CF_3$, or X may be a heterocycloalkyl containing one to two of the following optionally substituted heteroatoms: $NR^g$, O, and S; Z may be aryl or heteroaryl; Y may be O, $CH_2$, or cycloalkyl; $R^a$, $R^b$, $R^c$ and $R^d$ may each be H; $R^g$ may be H, alkyl, or $C_{3-7}$ cycloalkyl; and $R^h$ may be H, alkyl, or $C_{3-7}$ cycloalkyl.

In some aspects, in the mitofusin activator of formula (III), o may be 0, 1, 2, or 3; p may be 1; and q may be 0, 1, 2, or 3 with the proviso that the sum of o+p+q is not less than 3 or greater than 5; X may be a cycloalkyl with one to three of the following substituents: $R^g$, $OR^g$, $NR^gR^h$, F, or $CF_3$ or X may be a heterocycloalkyl having one to two of the following optionally substituted heteroatoms: O, $NR^g$, and S; Z may be aryl or heteroaryl; Y may be cyclopropyl or cyclobutyl; $R^a$, $R^b$, $R^c$ and $R^d$ may each be H; $R^g$ and $R^h$ may independently be H, alkyl, or $C_{3-7}$ cycloalkyl, or $R^g$ and $R^h$ taken together may form a $C_{3-7}$ cycloalkyl.

In some aspects, in the mitofusin activator of formula (III), o may be 0, 1, 2, 3, or 4; p may be 1; and q may be 0, 1, 2, 3, or 4 with the provision that the sum of o+p+q is 5; X may be cycloalkyl having one to three of the following substituents: $R^g$, $OR^g$, $NR^gR^h$, F, and $CF_3$, or X may be a heterocycloalkyl containing one to two of the following optionally substituted heteroatoms: O, $NR^g$, and S; Z may be aryl or heteroaryl; Y may be O or $CH_2$; $R^a$, $R^b$, $R^c$, and $R^d$ may each be H; $R^g$ may be selected from H, alkyl, and $C_{3-7}$ cycloalkyl; $R^h$ may be selected from H, alkyl, $COR^g$ and $C_{3-7}$ cycloalkyl, or optionally $R^g$ and $R^h$ taken together may form a $C_{3-7}$ cycloalkyl.

In some aspects, in the mitofusin activator of formula (III), X may be 4-hydroxycyclohexyl, 4-aminocyclohexyl, 4-(N-methyl)aminocyclohexyl, 4-(N,N-dimethyl)aminocyclohexyl, 4-(N-acetylamino)cyclohexyl, 4,4-difluorocyclohexyl, tetrahydropyranyl, tetrahydrothiopyranyl, piperidinyl, N-methyl-piperidinyl, or N-acetyl-piperidinyl; Z may be aryl or heteroaryl; Y may be O or $CH_2$; $R^a$, $R^b$, $R^c$, and $R^d$ may each be H; o may be 0, 1, 2, 3, or 4; p may be 1; and q may be 0, 1, 2, 3, or 4 with the proviso that the sum of o+p+q is 5.

In some aspects, in the mitofusin activator of formula (III), X is cycloalkyl, heterocycloalkyl, aryl, or heteroaryl, each containing one to four of the following heteroatoms: N, O, and S and having from zero to four of the following substituents: $R^g$, $OR^g$, $C_1$, F, CN, $CF_3$, —$NR^gR^h$, $SO_2NR^gR^h$, $NR^gSO_2R^1$, $SO_2R^1$, $CONR^gR^h$, $NR^hCOR^i$, $C_{3-7}$ cycloalkyl, and heterocycloalkyl; Z is phenyl or heteroaryl, wherein the heteroaryl may contain from one to four atoms independently selected from N, O, and S, and wherein the phenyl or heteroaryl has zero to four of the following substituents independently selected from $R^g$, $OR^g$, Cl, F, CN, $CF_3$, $NR^gR^h$, $SO_2NR^gR^h$, $NR^gSO_2R^1$, $SO_2R^1$, $CONR^gR^h$, $NR^hCOR^i$, $C_{3-7}$ cycloalkyl, and/or heterocycloalkyl; Y is O or $CH_2$; $R^a$, $R^b$, $R^c$, and $R^d$ may each be H; $R^g$ is selected from H, alkyl, and $C_{3-7}$ cycloalkyl; $R^h$ is selected from H, alkyl, $COR^g$ and $C_{3-7}$ cycloalkyl, or $R^h$ and $R^h$ taken together may form a $C_{3-7}$ cycloalkyl; $R^i$ is alkyl or $C_{3-7}$ cycloalkyl; o is 0, 1, 2, 3, or 4; p is 1; and q is 0, 1, 2, 3, or 4 with the proviso that the sum of o+p+q is 5.

In some aspects, in the mitofusin activator of formula (III), X may be 4-hydroxycyclohexyl, 4-aminocyclohexyl, 4-(N-methyl)aminocyclohexyl, 4-(N,N-dimethyl)aminocyclohexyl, 4-(N-acetylamino)cyclohexyl, 4,4-difluorocyclohexyl, tetrahydropyranyl, tetrahydrothiopyranyl, piperidinyl, N-methyl-piperidinyl, or N-acetyl-piperidinyl; Z may be phenyl or heteroaryl, wherein the heteroaryl may contain one to three of the following heteroatoms: N, O, and S and wherein the phenyl or heteroaryl may contain zero to three of the following substituents independently selected from $R^g$, $OR^g$, Cl, F, CN, $CF_3$, $NR^gR^h$, $SO_2R^i$, $CONR^gR^h$, $NR^hCOR^i$, $C_{3-7}$ cycloalkyl, and/or heterocycloalkyl; Y may be O or $CH_2$; $R^a$, $R^b$, $R^c$, and $R^d$ may each be H; $R^g$ may be selected from H, alkyl, and $C_{3-7}$ cycloalkyl; $R^h$ may be selected from H, alkyl, $COR^g$ and $C_{3-7}$ cycloalkyl, or $R^g$ and $R^h$ taken together may form a $C_{3-7}$ cycloalkyl; $R^i$ may be selected from alkyl and $C_{3-7}$ cycloalkyl; o may be 0, 1, 2, 3, or 4; p may be 1; and q may be 0, 1, 2, 3, or 4 with the proviso that the sum of o+p+q is 5.

In some aspects, in the mitofusin activator of formula (III), X may be 4-hydroxycyclohexyl, 4-aminocyclohexyl, 4-(N-methyl)aminocyclohexyl, 4-(N,N-dimethyl)aminocyclohexyl, 4-(N-acetylamino)cyclohexyl, 4,4-difluorocyclohexyl, tetrahydropyranyl, tetrahydrothiopyranyl, piperidinyl, 4-N-methyl-piperidinyl, or 4-N-acetyl-piperidinyl; Z may be phenyl, 2-pyridinyl, 3-pyridinyl, 4-pyridinyl, 6-pyrimidinyl, 5-pyrimidinyl, 4-pyrimidinyl, or 2-pyrimidinyl, wherein the phenyl, pyridinyl, and pyrimidinyl moiety may have zero to two of the following substituents independently selected from $R^g$, $OR^g$, Cl, F, CN, $CF_3$, $NR^gR^h$, $SO_2R^i$, $CONR^gR^h$, and/or $NR^gCOR^i$; Y may be O or $CH_2$; $R^a$, $R^b$, $R^c$, and $R^d$ may each be H; $R^g$ may be selected from H, alkyl, and $C_{3-7}$ cycloalkyl; $R^h$ may be selected from H, alkyl, $COR^g$ and $C_{3-7}$ cycloalkyl, or optionally, $R^g$ and $R^h$ taken together may form a $C_{3-7}$ cycloalkyl; $R^i$ may be alkyl or $C_{3-7}$ cycloalkyl; o may be 0, 1, 2, 3, or 4; p may be 1; and q may be 0, 1, 2, 3, or 4 with the proviso that the sum of o+p+q is 5.

In some aspects, in the mitofusin activator of formula (III), X is cycloalkyl or heterocycloalkyl; Y is O, $CR^eR^f$, cycloalkyl, or aryl; y is 1 $R^a$, $R^b$, $R^c$, $R^d$, $R^e$, and $R^f$ are each H or alkyl; and p is 1. In more particular aspects, X is selected from a cycloalkyl having one, two or three substituents independently selected from $R^g$, $OR^g$, $NR^gR^h$, F, and $CF_3$, and a heterocycloalkyl containing one or two optionally substituted heteroatoms independently selected from O, $NR^g$, and S; Y is O, $CH_2$ or cycloalkyl, particularly cyclopropyl or cyclobutyl; $R^a$, $R^b$, $R^c$, and $R^d$ are each H, $R^g$ and $R^h$ are selected as above, or $R^g$ and $R^h$ taken together form a $C_{3-7}$ cycloalkyl, and p is 1.

In some aspects, in the mitofusin activator of formula (III), X may be a cycloalkyl with having one, two, or three substituents independently selected from $R^g$, $OR^g$, $NR^gR^g$, F, and $CF_3$, or a heterocycloalkyl containing one or two optionally substituted heteroatoms independently selected from O, $NR^g$, and S; Z is phenyl, 2-pyridinyl, 3-pyridinyl, 4-pyridinyl, 2-pyrimidinyl; 4-pyrimidinyl, 5-pyrimidinyl, or 6-pyrimidinyl; Y is $NR^g$; $R^c$ and $R^d$ are H; o is 0; p is 1; and q is 4. In more particular aspects, $R^g$ is H. In another particular aspect, $R^g$ is H and Z is phenyl or substituted phenyl.

In some aspects, in the mitofusin activator of formula (III), X may be a cycloalkyl with having one, two, or three substituents independently selected from $R^g$, $OR^g$, $NR^gR^g$, F, and $CF_3$, or a heterocycloalkyl containing one or two optionally substituted heteroatoms independently selected from O, $NR^g$, and S; Z is phenyl, 2-pyridinyl, 3-pyridinyl, 4-pyridinyl, 2-pyrimidinyl; 4-pyrimidinyl, 5-pyrimidinyl, or 6-pyrimidinyl; $R^c$ and $R^d$ are H; o is 0; p is 0; and q is 5. In more particular aspects, Z is phenyl or substituted phenyl.

In some aspects, in the mitofusin activator of formula (III), X may be a cycloalkyl with having one, two, or three substituents independently selected from $R^g$, $OR^g$, $NR^gR^g$, F, and $CF_3$, or a heterocycloalkyl containing one or two optionally substituted heteroatoms independently selected from O, $NR^g$, and S; Z is phenyl, 2-pyridinyl, 3-pyridinyl, 4-pyridinyl, 2-pyrimidinyl; 4-pyrimidinyl, 5-pyrimidinyl, or 6-pyrimidinyl; Y is cyclopropyl or cyclobutyl; $R^c$ and $R^d$ are H; o is 0 or 1; p is 1; and q is 1, 2 or 3. In more particular aspects, Z is phenyl or substituted phenyl. In some or other particular aspects, Y is cyclopropyl, particularly 1,2-cyclopropyl, and q is 2 or 3; or Y is cyclobutyl, particularly 1,3-cyclobutyl, and q is 1 or 2.

In some aspects, in the mitofusin activator of formula (III), X may be a cycloalkyl with having one, two, or three substituents independently selected from $R^g$, $OR^g$, $NR^gR^g$, F, and $CF_3$, or a heterocycloalkyl containing one or two optionally substituted heteroatoms independently selected from O, $NR^g$, and S; Z is phenyl, 2-pyridinyl, 3-pyridinyl, 4-pyridinyl, 2-pyrimidinyl; 4-pyrimidinyl, 5-pyrimidinyl, or 6-pyrimidinyl; Y is cyclopropyl or cyclobutyl; $R^a$, $R^b$, $R^c$ and $R^d$ are H; o is 0 or 1; p is 1; and q is 1, 2 or 3. In more particular aspects, Z is phenyl or substituted phenyl. In some or other particular aspects, Y is cyclopropyl, particularly 1,2-cyclopropyl, and q is 2 or 3; or Y is cyclobutyl, particularly 1,3-cyclobutyl, and q is 1 or 2. In some or other more particular aspects, Y is cyclobutyl, particularly 1,3-cyclobutyl, o is 1 and q is 1.

In another aspect of the present disclosure, a method of treating a disease for which a mitofusin activator is indicated may comprise administering to a mammal in need thereof a therapeutically effective amount of a compound of Formula (III)

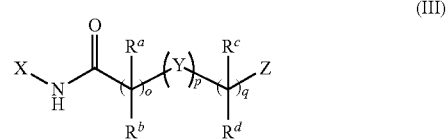

or a pharmaceutically salt thereof. In Formula (III), o is 0, 1, 2, 3, 4, or 5; p is 0 or 1; and q is 0, 1, 2, 3, 4, or 5 with the proviso that the sum of o+p+q is not less than 3 or greater than 7; X may be cycloalkyl, heterocycloalkyl, aryl, or heteroaryl; Z may be cycloalkyl, heterocycloalkyl, aryl, or heteroaryl; $R^a$ and $R^a$ may independently be H, F, alkyl, or $C_{3-7}$ cycloalkyl, or $R^1$ and $R^2$ taken together may form a $C_{3-7}$ cycloalkyl or heterocycloalkyl; $R^c$ and $R^d$ may independently be H, F, alkyl, $COR^g$, and/or $C_{3-7}$ cycloalkyl, or $R^c$ and $R^d$ may be taken together to form a $C_{3-7}$ cycloalkyl or heterocycloalkyl; Y is O, $CR^eR^f$, $CR^g$=$CR^h$, C≡C, cycloalkyl, heterocycloalkyl, aryl, heteroaryl, $NR^g$, S, $SO_2$, $SONR^h$, $NR^hSO_2$, $NR^gCO$, $CONR^g$, or $NR^gCONR^h$; $R^e$ and $R^f$ may independently be H, F, alkyl, and/or cycloalkyl, or $R^e$ and $R^f$ taken together may form a $C_{3-7}$ cycloalkyl or heterocycloalkyl; and $R^g$ and $R^h$ may independently be H, alkyl, and/or $C_{3-7}$ cycloalkyl.

In some aspects, in the method of treating a disease for which a mitofusin activator is indicated, the PNS or CNS disorder may be selected from any one or a combination of: a chronic neurodegenerative condition wherein mitochondrial fusion, fitness, or trafficking are impaired; a disease or disorder associated with mitofusin 1 (MFN1) or mitofusin 2 (MFN2) dysfunction; a disease associated with mitochondrial fragmentation, dysfunction, or dysmotility; a degenerative neuromuscular condition such as Charcot-Marie-Tooth disease, amyotrophic lateral sclerosis (ALS), Huntington's disease, Alzheimer's disease, Parkinson's disease, hereditary motor and sensory neuropathy, autism, autosomal dominant optic atrophy (ADOA), muscular dystrophy, Lou Gehrig's disease, cancer, mitochondrial myopathy, diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), mtDNA depletion, mitochondrial neurogastrointestinal encephalomyopathy (MNGIE), dysautonomic mitochondrial myopathy, mitochondrial channelopathy, or pyruvate dehydrogenase complex deficiency (PDCD/PDH), diabetic neuropathy, chemotherapy-induced peripheral neuropathy, crush injury, SCI, traumatic brain injury (TBI), stroke, optic nerve injury, and/or related conditions that involve axonal disconnection.

In some aspects of the disclosure, in the method of treating a disease for which a mitofusin activator is indicated, the composition may further comprise a pharmaceutically acceptable excipient.

In some aspects of the disclosure, in the method of treating a CNS and/or PNS genetic and/or non-genetic neurodegenerative condition, injury, damage, and/or trauma comprising administering to the subject a therapeutically effective amount of a mitofusin activator according to the present disclosure.

In some aspects of the disclosure, in the method of treating a CNS or PNS genetic or non-genetic neurodegenerative condition, injury, damage, or trauma, the subject may be diagnosed with or is suspected of having one or more of the following: a chronic neurodegenerative condition wherein mitochondrial fusion, fitness, or trafficking are impaired; a disease or disorder associated with MFN1 or MFN2 dysfunction; a disease associated with mitochondrial fragmentation, dysfunction, or dysmotility; a degenerative neuromuscular condition (such as Charcot-Marie-Tooth disease, ALS, Huntington's disease, Alzheimer's disease, Parkinson's disease); hereditary motor and sensory neuropathy, autism, ADOA, muscular dystrophy, Lou Gehrig's disease, cancer, mitochondrial myopathy, DAD, LHON, Leigh syndrome, subacute sclerosing encephalopathy, NARP, MNGIE, MERRF, MELAS, mtDNA depletion, MNGIE, dysautonomic mitochondrial myopathy, mitochondrial Channelopathy, PDCD/PDH, diabetic neuropathy, chemotherapy-induced peripheral neuropathy, crush injury, SCI, TBI, stroke, optic nerve injury, and/or related conditions that involve axonal disconnection.

In some aspects, a method of screening one or more candidate molecules for mitochondrial fusion modulatory activity may comprise one or more of the following: (i) constitutively expressing a mitochondrial-targeted photoswitchable fluorophore in cells expressing different combinations of MFN1 or MFN2 in a genetically-defined manner; (ii) photoswitching mitochondrial-targeted fluorophores in a micro-matrix pattern in cells transiently or constitutively expressing a mitochondrial-targeted photoswitchable fluorophore; and (iii) measuring merged/overlay fluorescence in photoswitched mitochondria.

In some aspects, a method of screening one or more candidate molecules for mitochondrial fusion modulatory activity may further comprise comparing the merged/overlay fluorescence of the test mixture with the merged/overlay fluorescence of the control mixture, wherein when the merged/overlay fluorescence of the test mixture is greater than the merged/overlay fluorescence of the control mixture, the one or more candidate molecules in the test mixtures is identified as an activator of mitochondrial fusion.

In some aspects, a method of screening one or more candidate molecules for mitochondrial fusion modulatory activity may further comprise comparing the merged/overlay fluorescence of the test mixture of a candidate agent in wild-type, MFN1, or MFN2 expressing cells with the merged/overlay fluorescence of that candidate agent in cells lacking both MFN1 and MFN2 (MFN null cells), wherein the merged/overlay fluorescence of the mixture in MFN expressing cells is greater than the merged/overlay fluorescence of the mixture in MFN null cells, the one or more candidate molecules in the test mixtures is identified as a mitofusin activator.

The terms "imine" or "imino," as used herein, unless otherwise indicated, include a functional group or chemical compound containing a carbon-nitrogen double bond. The expression "imino compound," as used herein, unless otherwise indicated, refers to a compound that includes an "imine" or an "imino" group as defined herein. The "imine" or "imino" group may be optionally substituted.

The term "hydroxy," as used herein, unless otherwise indicated, includes —OH. The "hydroxy" may be optionally substituted (e.g., incorporated in an alkoxide, phenoxide, or carboxylic acid ester).

The terms "halogen" and "halo", as used herein, unless otherwise indicated, include a chlorine, chloro, Cl; fluorine, fluoro, F; bromine, bromo, Br; and iodine, iodo, or I.

The term "acetamide," as used herein, is an organic compound with the formula $CH_3CONH_2$. The "acetamide" may be optionally substituted.

The term "aryl," as used herein, unless otherwise indicated, includes a carbocyclic aromatic group. Examples of aryl groups include, but are not limited to, phenyl, benzyl, naphthyl, and anthracenyl. The "aryl" may be optionally substituted.

The terms "amine" and "amino", as used herein, unless otherwise indicated, include a functional group that contains a nitrogen atom with a lone pair of electrons and wherein one or more hydrogen atoms have been replaced by a substituent such as, but not limited to, an alkyl group or an aryl group. The "amine" or "amino" group may be optionally substituted.

The term "alkyl," as used herein, unless otherwise indicated, includes saturated monovalent hydrocarbon radicals having straight or branched moieties, such as but not limited to, methyl, ethyl, propyl, butyl, pentyl, hexyl, and octyl groups. Representative straight-chain lower alkyl groups include, but are not limited to, methyl, ethyl, n-propyl, n-butyl, n-pentyl, n-hexyl, n-heptyl and n-octyl. Branched lower alkyl groups include, but are not limited to, isopropyl, sec-butyl, isobutyl, tert-butyl, isopentyl, 2-methylbutyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 1-hexyl, 2-hexyl, 3-hexyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, and 3-methylheptyl. Unsaturated alkyl groups may be referred to as alkenyl (at least one carbon-carbon double bond) or alkynyl (at least one carbon-carbon triple bond) groups, which may include, but are not limited to, vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, acetylenyl, propynyl, 1-butynyl, 2-butynyl, 1-pentynyl, 2-pentynyl, or 3-methyl-1 butynyl. E and Z isomers may be present in any alkenyl group. The "alkyl," "alkenyl," or "alkynyl" may be optionally substituted.

The term "carboxyl," as used herein, unless otherwise indicated, includes a functional group containing a carbon atom double bonded to an oxygen atom and single bonded to a hydroxyl group (—COOH). The "carboxyl" may be optionally substituted.

The term "acyl," as used herein, unless otherwise indicated, includes a functional group derived from an aliphatic carboxylic acid by removal of the hydroxy (—OH) group. The "acyl" may be optionally substituted.

The term "alkoxy," as used herein, unless otherwise indicated, includes O-alkyl groups wherein alkyl is as defined above and O represents oxygen. Representative alkoxy groups include, but are not limited to, —O-methyl, —O-ethyl, —O-n-propyl, —O-n-butyl, —O-n-pentyl, —O-n-hexyl, —O-n-heptyl, —O-n-octyl, —O-isopropyl, —O-sec-butyl, —O-isobutyl, —O-tert-butyl, —O-isopentyl, —O-2-methylbutyl, —O-2-methylpentyl, —O-3-methylpentyl, —O-2,2-dimethylbutyl, —O-2,3-dimethylbutyl, —O-2,2-dimethylpentyl, —O-2,3-dimethylpentyl, —O-3,3-dimethylpentyl, —O-2,3,4-trimethylpentyl, —O-3-methylhexyl, —O-2,2-dimethylhexyl, —O-2,4-dimethylhexyl, —O-2,5-dimethylhexyl, —O-3,5-dimethylhexyl, —O-2,4-dimethylpentyl, —O-2-methylheptyl, —O-3-methylheptyl, —O-vinyl, —O-allyl, —O-1-butenyl, —O-2-butenyl, —O— isobutylenyl, —O-1-pentenyl, —O-2-pentenyl, —O-3-methyl-1-butenyl, —O-2-methyl-2-butenyl, —O-2,3-dimethyl-2-butenyl, —O-1-hexyl, —O-2-hexyl, —O-3-hexyl, —O-acetylenyl, —O-propynyl, —O-1-butynyl, —O-2-butynyl, —O-1-pentynyl, —O-2-pentynyl, —O-3-methyl-1-butynyl, —O— cyclopropyl, —O-cyclobutyl, —O-cyclopentyl, —O-cyclohexyl, —O-cycloheptyl, —O-cyclooctyl, —O-cyclononyl, —O-cyclodecyl, —O—CH$_2$-cyclopropyl, —O—CH$_2$-cyclobutyl, —O—CH$_2$-cyclopentyl, —O—CH$_2$-cyclohexyl, —O—CH$_2$-cycloheptyl, —O—CH$_2$-cyclooctyl, —O—CH$_2$-cyclononyl, —O—CH$_2$-cyclodecyl, —O—(CH$_2$)$_n$-cyclopropyl, —O—(CH$_2$)$_n$-cyclobutyl, —O—(CH$_2$)$_n$-cyclopentyl, —O—(CH$_2$)$_n$-cyclohexyl, —O—(CH$_2$)$_n$-cycloheptyl, —O—(CH$_2$)$_n$-cyclooctyl, —O—(CH$_2$)$_n$-cyclononyl, and/or —O—(CH$_2$)$_n$-cyclodecyl. The alkoxy may be saturated, partially saturated, or unsaturated. The "alkoxy" may be optionally substituted. In any example above, n may be from one to about twenty.

The term "cycloalkyl," as used herein, unless otherwise indicated, includes a non-aromatic, saturated, partially saturated, or unsaturated, monocyclic or fused, spiro or unfused bicyclic or tricyclic hydrocarbon referred to herein containing a total of from 3 to 10 carbon atoms. Examples of cycloalkyls include, but are not limited to, C$_{3-10}$ cycloalkyl groups including cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl. The term "cycloalkyl" also includes lower alkyl-cycloalkyl, wherein lower alkyl and cycloalkyl are as defined herein. Examples of lower alkyl-cycloalkyl groups include, but are not limited to, —CH$_2$-cyclopropyl, —CH$_2$-cyclobutyl, —CH$_2$-cyclopentyl, —CH$_2$— cyclopentadienyl, —CH$_2$-cyclohexyl, —CH$_2$-cycloheptyl, and/or —CH$_2$-cyclooctyl. The "cycloalkyl" may be optionally substituted.

The term "heterocyclic", as used herein, unless otherwise indicated, includes an aromatic group or a non-aromatic cycloalkyl group in which one to four of the ring carbon atoms are independently replaced with one or more of O, S, and N. Aromatic heterocyclic groups are referred to as "heteroaryl" groups. Non-aromatic heterocyclic groups are referred to as "heterocyclyl" groups. Representative examples of heterocyclic groups include, but are not limited to, benzofuranyl, benzothiophene, indolyl, benzopyrazolyl, coumarinyl, isoquinolinyl, pyrrolyl, pyrrolidinyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl, (1,4)-dioxane, (1,3)-dioxolane, 4,5-dihydro-1H-imidazolyl, and/or tetrazolyl. Heterocyclic groups may be substituted or unsubstituted. Heterocyclic groups may also be bonded at any ring atom (i.e., at any carbon atom or heteroatom of the heterocyclic ring). The heterocyclic group may be saturated, partially saturated, or unsaturated.

The term "indole," as used herein, is an aromatic heterocyclic organic compound with formula $C_8H_7N$. It has a bicyclic structure containing a six-membered benzene ring fused to a five-membered nitrogen-containing pyrrole ring. The "indole" may be optionally substituted.

The term "cyano," as used herein, unless otherwise indicated, includes a CN group.

The term "alcohol," as used herein, unless otherwise indicated, includes a compound in which a hydroxy functional group (—OH) is bound to a carbon atom. In particular, this carbon atom may be saturated, having single bonds to three other atoms. The "alcohol" may be optionally substituted. The "alcohol" may be a primary, secondary, or tertiary alcohol.

The term "solvate" is intended to mean a solvated form of a specified compound that retains the effectiveness of such compound. Examples of solvates include compounds of the invention in combination with, but not limited to, one or more of: water, isopropanol, ethanol, methanol, dimethylsulfoxide (DMSO), ethyl acetate, acetic acid, or ethanolamine.

The term "mmol," as used herein, is intended to mean millimole. The term "equiv" and "eq.," as used herein, are intended to mean equivalent. The term "ml_," as used herein, is intended to mean milliliter. The term "g," as used herein, is intended to mean gram. The term "kg," as used herein, is intended to mean kilogram. The term "μg," as used herein, is intended to mean micrograms. The term "h," as used herein, is intended to mean hour. The term "min," as used herein, is intended to mean minute. The term "M," as used herein, is intended to mean molar. The term "μL," as used herein, is intended to mean microliter. The term "μM," as used herein, is intended to mean micromolar. The term "nM," as used herein, is intended to mean nanomolar. The term "N," as used herein, is intended to mean normal. The term "amu," as used herein, is intended to mean atomic mass unit. The term "° C.," as used herein, is intended to mean degree Celsius. The term "wt/wt," as used herein, is intended to mean weight/weight. The term "v/v," as used herein, is intended to mean volume/volume. The term "MS," as used herein, is intended to mean mass spectrometry. The term "HPLC," as used herein, is intended to mean high performance liquid chromatography. The term "RT," as used herein, is intended to mean room temperature or retention time, depending on context. The term "e.g.," as used herein, is intended to mean for example. The term "N/A," as used herein, is intended to mean not tested or not applicable.

As used herein, the expression "pharmaceutically acceptable salt" refers to pharmaceutically acceptable organic or inorganic salts of a compound of the invention. Suitable salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and/or pamoate (i.e., 1,1'-methylene-bis-(2-hydroxy-3-naphthoate)) salts. A pharmaceutically acceptable salt may involve the inclusion of another molecule such as an acetate ion, a succinate ion, or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt may have multiple counterions. Hence, a pharmaceutically acceptable salt may have one or more charged atoms and/or one or more counterion. As used herein, the expression "pharmaceutically acceptable solvate" refers to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and/or ethanolamine. As used herein, the expression "pharmaceutically acceptable hydrate" refers to a compound of the invention, or a salt thereof, that further includes a stoichiometric or non-stoichiometric amount of water bound by non-covalent intermolecular forces.

Each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Mitofusin 1 and Mitofusin 2

Mitochondria generate adenosine triphosphate (ATP) that fuels neuronal activity. Mitochondria must fuse in order to exchange genomes and promote mutual repair. The initial stages of mitochondrial fusion proceed through the physiochemical actions of two functionally redundant and structurally related dynamin family GTPases, MFN1 and MFN 2. The obligatory first step leading to mitochondrial fusion is molecular tethering of two mitochondria via homo- or hetero-oligomerization (in trans) of extended MFN1 or MFN2 carboxyl termini. Subsequently, GTP binding to and hydrolysis by MFN1 or MFN2 promotes irreversible physical fusion of the organellar outer membranes.

Mitofusins belong to a class of highly conserved GTPases that are located on the outer membrane of mitochondria in mammals, flies, the worm, and budding yeast. Each of MFN1 and MFN2, the mitofusins present in mammals, are anchored to the outer membrane by two transmembrane domains such that their N-terminus and C-terminus are exposed to the cytoplasm. Mitofusins on different organelles undergo transdimerization through anti-parallel binding of their extended carboxy terminal α-helical domains to form mitochondria-mitochondria tethers—the obligate initial step in mitochondrial fusion (Koshiba et al., 2004, Science, 305:858-861). Conventional wisdom is that mitofusins exist constitutively in this "active" extended molecular conformation, which supports mitochondrial tethering, although other possible conformations and the likelihood of functionally relevant molecular plasticity have not been rigorously tested. The components involved in mitochondrial tethering involve intermolecular and possibly intramolecular interactions of particular MFN1 and MFN2 domains. These interactions were further studied and exploited in the design and testing of compositions which affect the interactions and the resultant mitochondrial function.

MFN1 and MFN2 share a common domain structure. The amino terminal globular GTPase domain is followed by a coiled-coiled heptad repeat region (HR1), two adjacent small transmembrane domains, and a carboxyl terminal coiled heptad repeat region (HR2). Amino acid conservation between MFN1 and MFN2 varies by domain, being most highly conserved in the GTPase, transmembrane, and HR2 domains. HR2 domains extending from MFN1 molecules located on different mitochondria may bind to each other, forming inter-molecular HR2-HR2 interactions that link the molecules and tether the organelles (Koshiba et al., ibid). HR2 may also bind to HR1 (Huang et al., 2011, PLoS One, 6:e20655; Franco et al Nature 2016.), The crystal structure of bacterial dynamin-like protein (DLP) (Low and Lowe, 2006, Nature, 444:766-769; Protein Data Bank (PDB) ID No. 2J69) was used to model MFN2 structure. The alignment and modeling of MFN2 based on the DLP structure provided a template for the expansion and refining of the identities of HR2 amino acids that mediate inter-molecular HR2-HR2 tethering (Koshiba et al., 2004, Science, 305:858-861). This analysis led to the conception that these same amino acids mediate, via peptide-peptide interactions, intra-molecular antiparallel binding of HR2 to HR1.

Mitochondria-Associated Diseases, Disorders, or Conditions

The present disclosure provides for compositions and methods of treatment for treating mitochondria-related diseases, disorders, or conditions, including diseases or disorders associated with MFN1 and/or MFN2 and mitochondrial dysfunction. A mitochondria-associated disease, disorder, or condition may be a disease primarily caused by or secondarily associated with mitochondrial dysfunction, fragmentation, or loss-of-fusion, or associated with dysfunction in MFN1 or MFN2 catalytic activity or conformational unfolding. Mitochondrial dysfunction may be caused by genetic mutations of mitofusins or other (nuclear or mitochondrial encoded) genes, or may be caused by physical, chemical, or environmental injury to the CNS or PNS.

Mitochondria transit within cells and undergo fusion to exchange genomes and promote mutual repair. Mitochondrial fusion and subcellular trafficking are mediated in part by MFN1 and MFN2. Genetic mutations in MFN2 that suppress mitochondrial fusion and motility cause Charcot-Marie-Tooth Disease, type 2A (CMT2A), the most common heritable axonal neuropathy. Mitochondrial fragmentation, dysfunction, and dysmotility are also central features of other genetic neurodegenerative syndromes, such as amyotrophic lateral sclerosis, Huntington's disease, Parkinson's disease, and Alzheimer's disease. Because no therapeutics exist that directly enhance mitochondrial fusion or trafficking, these diseases are unrelenting and considered irreversible.

Examples of mitochondria-associated diseases, disorders, and conditions include, but are not limited to, Alzheimer's disease, Parkinson's disease, Huntington's disease, Charcot-Marie-Tooth Disease (type 2A) (CMT), hereditary motor and sensory neuropathy, autism, ADOA, muscular dystrophy, Lou Gehrig's disease, cancer, mitochondrial myopathy, DAD, LHON, Leigh syndrome, subacute sclerosing encephalopathy, NARP, MNGIE, MERRF, MELAS, mtDNA depletion, MNGIE, dysautonomic mitochondrial myopathy, mitochondrial channelopathy, and/or PDCD/PDH.

Symptoms that may be treated with the methods as described herein include, but are not limited to, poor growth, loss of muscle coordination, muscle paralysis and atrophy, visual problems, hearing problems, learning disabilities, heart disease, liver disease, kidney disease, gastrointestinal disorders, respiratory disorders, neurological problems, autonomic dysfunction, and dementia.

Neurodegenerative Disease

As described herein, mitofusin activators rapidly reverse mitochondrial dysmotility in sciatic nerve axons of a mouse model of Charcot-Marie-Tooth disease, type 2A. Because impaired mitochondrial fusion, fitness, and/or trafficking also contribute to neuronal degeneration in various neurodegenerative diseases (e.g., in Charcot-Marie-Tooth disease (CMT2A), Huntington's disease, Parkinson's disease, and Alzheimer's disease, and especially in ALS), the present disclosure provides for compositions (e.g., compositions containing mitofusin activators) and methods to treat such neurodegenerative diseases, disorders, and/or conditions.

Examples of neurodegenerative diseases, disorders and conditions include a disease of impaired neuronal mitochondrial dynamism or trafficking, such as, but not limited to, a hereditary motor and sensory neuropathy (HMSN) (e.g., CMT1 (a dominantly inherited, hypertrophic, predominantly demyelinating form), CMT2 (a dominantly inherited predominantly axonal form), Dejerine-Sottas (severe form with onset in infancy), CMTX (inherited in an X-linked manner), and CMT4 (includes the various demyelinating autosomal recessive forms of Charcot-Marie-Tooth disease); hereditary sensory and autonomic neuropathy type IE, hereditary sensory and autonomic neuropathy type II, hereditary sensory and autonomic neuropathy type V, HMSN types 1A and 1B (e.g., dominantly inherited hypertrophic demyelinating neuropathies), HMSN type 2 (e.g., dominantly inherited neuronal neuropathies), HMSN type 3 (e.g., hypertrophic neuropathy of infancy [Dejerine-Sottas]), HMSN type 4 (e.g., hypertrophic neuropathy [Refsum] associated with phytanic acid excess), HMSN type 5 (associated with spastic paraplegia), and/or HMSN type 6 (e.g., with optic atrophy)).

Other examples of neurodegenerative diseases, disorders, and conditions include, but are not limited to, Alzheimer's disease, ALS, Alexander disease, Alpers' disease, Alpers-Huttenlocher syndrome, alpha-methylacyl-CoA racemase deficiency, Andermann syndrome, Arts syndrome, ataxia neuropathy spectrum, ataxia (e.g., with oculomotor apraxia, autosomal dominant cerebellar ataxia, deafness, and narcolepsy), autosomal recessive spastic ataxia of Charlevoix-Saguenay, Batten disease, beta-propeller protein-associated neurodegeneration, cerebro-oculo-facio-skeletal syndrome (COFS), corticobasal degeneration, CLN1 disease, CLN10 disease, CLN2 disease, CLN3 disease, CLN4 disease, CLN6 disease, CLN7 disease, CLN8 disease, cognitive dysfunction, congenital insensitivity to pain with anhidrosis, dementia, familial encephalopathy with neuroserpin inclusion bodies, familial British dementia, familial Danish dementia, fatty acid hydroxylase-associated neurodegeneration, Friedreich's Ataxia, Gerstmann-Straussler-Scheinker Disease, GM2-gangliosidosis (e.g., AB variant), HMSN type 7 (e.g., with retinitis pigmentosa), Huntington's disease, infantile neuroaxonal dystrophy, infantile-onset ascending hereditary spastic paralysis, infantile-onset spinocerebellar ataxia, juvenile primary lateral sclerosis, Kennedy's disease, Kuru, Leigh's Disease, Marinesco-Sjögren syndrome, mild cognitive impairment (MCI), mitochondrial membrane protein-associated neurodegeneration, motor neuron disease, monomelic amyotrophy, motor neuron diseases (MND), multiple system atrophy, multiple system atrophy with orthostatic hypotension (Shy-Drager Syndrome), multiple sclerosis, multiple system atrophy, neurodegeneration in down's syndrome (NDS), neurodegeneration of aging, neurodegeneration with brain iron accumulation, neuromyelitis optica, pantothenate kinase-associated neurodegeneration, opsoclonus myoclonus, prion disease, progressive multifocal leukoencephalopathy, Parkinson's disease, Parkinson's disease-related disorders, polycystic lipomembranous osteodysplasia with sclerosing leukoencephalopathy, prion disease, progressive external ophthalmoplegia, riboflavin transporter deficiency neuronopathy, Sandhoff disease, spinal muscular atrophy (SMA), spinocerebellar ataxia (SCA), striatonigral degeneration, transmissible spongiform encephalopathies (prion diseases), and/or Wallerian-like degeneration.

Charcot-Marie-Tooth (CMT) Disease Type 2A.

Charcot-Marie-Tooth type 2A (CMT2A) disease is an example of a non-curable neurodegenerative disease/axonal neuropathy, disorder, or condition caused by mutations of MFN2 and for which there are currently no disease-modifying treatments. As described herein, it was discovered that severely impaired mitochondrial transport from neuron cell body in the spinal cord to distal neuronal synapse in the lower leg or hand (in addition to smaller mitochondria size as is widely recognized) is a central factor in CMT2A disease onset and progression. CMT2A is a progressive neuromuscular disease that typically causes muscle weakness and wasting in the distal legs/feet in children of ages 1-8 years, then upper limbs, ultimately producing severe muscle wasting, skeletal deformities, and permanent disability. The present disclosure provides for the correction of impaired neuronal mitochondria transport as a therapeutic target in this disease. Data showed that administration of a mitofusin activator promoted the mitochondria to move along neuronal axons in mouse models where mitochondria were not previously moving, which is applicable in any neuropathy (e.g., Huntington's disease, ALS, ALS-like sclerosis, and/or Alzheimer's disease).

Neurological Disease as Described in Franco et al. Nature 2016 and Rocha et al. Science 2018

As described herein, mitofusin activators rapidly reverse mitochondrial dysmotility in sciatic nerve axons of a mouse model of Charcot-Marie-Tooth disease type 2A. It is currently believed that impaired mitochondrial trafficking also contribute to neuronal degeneration in various neurological diseases (e.g., in Huntington's disease, Parkinson's disease, and Alzheimer's disease, and especially in ALS). As such, the present disclosure provides for methods and compositions to treat neurological diseases, disorders, or conditions. For example, a neurological disease, disorder, or condition may be, but is not limited to, abulia; agraphia; alcoholism; alexia; alien hand syndrome; Allan-Herndon-Dudley syndrome; alternating hemiplegia of childhood; Alzheimer's disease; amaurosis fugax; amnesia; ALS; aneurysm; angelman syndrome; anosognosia; aphasia; apraxia; arachnoiditis; Arnold-Chiari malformation; asomatognosia; Asperger syndrome; ataxia; attention deficit hyperactivity disorder; atr-16 syndrome; auditory processing disorder; autism spectrum; Behcets disease; bipolar disorder; Bell's palsy; brachial plexus injury; brain damage; brain injury; brain tumor; Brody myopathy; Canavan disease; capgras delusion; carpal tunnel syndrome; causalgia; central pain syndrome; central pontine myelinolysis; centronuclear myopathy; cephalic disorder; cerebral aneurysm; cerebral arteriosclerosis; cerebral atrophy; cerebral autosomal dominant arteriopathy with subcortical infarcts and leukoencephalopathy (CADASIL); cerebral dysgenesis-neuropathy-ichthyosis-keratoderma syndrome (CEDNIK syndrome); cerebral gigantism; cerebral palsy; cerebral vasculitis; cervical spinal stenosis; Charcot-Marie-Tooth disease; chiari malformation; chorea; chronic fatigue syndrome; chronic inflammatory demyelinating polyneuropathy (CIDP); chronic pain; Cockayne syndrome; C off in-Lowry syndrome; coma; complex regional pain syndrome; compression neuropathy; congenital facial diplegia; corticobasal degeneration; cranial arteritis; craniosynostosis; Creutzfeldt-Jakob disease; cumulative trauma disorders; Cushing's syndrome; cyclothymic disorder; cyclic vomiting syndrome (CVS); cytomegalic inclusion body disease (CIBD); cytomegalovirus infection; Dandy-Walker syndrome; Dawson disease; de Morsier's syndrome; Dejerine-Klumpke palsy; Dejerine-Sottas disease; delayed sleep phase syndrome; dementia; dermatomyositis; developmental coordination disorder; diabetic neuropathy; diffuse sclerosis; diplopia; disorders of consciousness; down syndrome; Dravet syndrome; duchenne muscular dystrophy; dysarthria; dysautonomia; dyscalculia; dysgraphia; dyskinesia; dyslexia; dystonia; empty sella syndrome; encephalitis; encephalocele; encephalotrigeminal angiomatosis; encopresis; enuresis; epilepsy; epilepsy-intellectual disability in females; erb's palsy; erythromelalgia; essential tremor; exploding head syndrome; Fabry's disease; Fahr's syndrome; fainting; familial spastic paralysis; febrile seizures; Fisher syndrome; Friedreich's ataxia; fibromyalgia; Foville's syndrome; fetal alcohol syndrome; fragile x syndrome; fragile x-associated tremor/ataxia syndrome (FX-TAS); Gaucher's disease; generalized epilepsy with febrile seizures plus; Gerstmann's syndrome; giant cell arteritis; giant cell inclusion disease; globoid cell leukodystrophy; gray matter heterotopia; Guillain-Barré syndrome; generalized anxiety disorder; HTLV-1 associated myelopathy; Hallervorden-Spatz syndrome; head injury; headache; hemifacial spasm; hereditary spastic paraplegia; heredopathia atactica polyneuritiformis; herpes zoster oticus; herpes zoster; Hirayama syndrome; Hirschsprung's disease; Holmes-Adie syndrome; holoprosencephaly; Huntington's disease; hydranencephaly; hydrocephalus; hypercortisolism; hypoxia; immune-mediated encephalomyelitis; inclusion body myositis; incontinentia pigmenti; infantile refs urn disease; infantile spasms; inflammatory myopathy; intracranial cyst; intracranial hypertension; isodicentric 15; Joubert syndrome; Karak syndrome; Kearns-Sayre syndrome; Kinsbourne syndrome; Kleine-Levin syndrome; Klippel Fell syndrome; Krabbe disease; Kufor-Rakeb syndrome; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; leukoencephalopathy with vanishing white matter; lewy body dementia; lissencephaly; locked-in syndrome; Lou Gehrig's disease (amyotrophic lateral sclerosis (ALS)); lumbar disc disease; lumbar spinal stenosis; lyme diseas—neurological sequelae; Machado-Joseph disease (spinocerebellar ataxia type 3); macrencephaly; macropsia; mal de debarquement; megalencephalic leukoencephalopathy with subcortical cysts; megalencephaly; Melkersson-Rosenthal syndrome; menieres disease; meningitis; Menkes disease; metachromatic leukodystrophy; microcephaly; micropsia; migraine; Miller Fisher syndrome; mini-stroke (transient ischemic attack); misophonia; mitochondrial myopathy; mobius syndrome; monomelic amyotrophy; Morvan syndrome; motor neurone disease—see ALS; motor skills disorder; moyamoya disease; mucopolysaccharidoses; multi-infarct dementia; multifocal motor neuropathy; multiple sclerosis; multiple system atrophy; muscular dystrophy; myalgic encephalomyelitis; myasthenia gravis; myelinoclastic diffuse sclerosis; myoclonic encephalopathy of infants; myoclonus; myopathy; myotubular myopathy; myotonia congenita; narcolepsy; neuro-Behcet's disease; neurofibromatosis; neuroleptic malignant syndrome; neurological manifestations of aids; neurological sequelae of lupus; neuromyotonia; neuronal ceroid lipofuscinosis; neuronal migration disorders; neuropathy; neurosis; Niemann-Pick disease; non-24-hour sleep-wake disorder; nonverbal learning disorder; O'Sullivan-McLeod syndrome; occipital neuralgia; occult spinal dysraphism sequence; Ohtahara syndrome; olivopontocerebellar atrophy; opsoclonus myoclonus syndrome; optic neuritis; orthostatic hypotension; otosclerosis; overuse syndrome; palinopsia; paresthesia; Parkinson's disease; paramyotonia congenita; paraneoplastic diseases; paroxysmal attacks; Parry-Romberg syndrome; pediatric autoimmune neuropsychiatric disorders associated with streptococcoal infections (PANDAS); Pelizaeus-Merzbacher disease; periodic paralyses; peripheral neuropathy; pervasive developmental disorders; phantom limb/phantom pain; photic sneeze reflex; phytanic acid storage disease; Pick's disease; pinched nerve; pituitary tumors; pmg; polyneuropathy; polio; polymicrogyria; polymyositis; porencephaly; post-polio syndrome; postherpetic neuralgia (phn); postural hypotension; Prader-Willi syndrome; primary lateral sclerosis; prion diseases; progressive hemifacial atrophy; progressive multifocal leukoencephalopathy; progressive supranuclear palsy; prosopagnosia; pseudotumor cerebri; quadrantanopia; quadriplegia; rabies; radiculopathy; Ramsay Hunt syndrome type 1; Ramsay Hunt syndrome type 2; Ramsay Hunt syndrome type 3—see Ramsay-Hunt syndrome; Rasmussen encephalitis; reflex neurovascular dystrophy; refsum disease; REM sleep behavior disorder; repetitive stress injury; restless legs syndrome; retrovirus-associated myelopathy; Rett syndrome; Reye's syndrome; rhythmic movement disorder; Romberg syndrome; Saint Vitus' dance; Sandhoff disease; Schilder's disease (two distinct conditions); schizencephaly; sensory processing disorder; septo-optic dysplasia; shaken baby syndrome; shingles; Shy-Drager syndrome; Sjögren's syndrome; sleep apnea; sleeping sickness; snatiation; Sotos syndrome; spasticity; spina bifida; spinal cord injury; spinal cord tumors; spinal muscular atrophy; spinal and bulbar muscular atrophy; spinocerebellar ataxia; split-brain; Steele-Richardson-Olszewski syndrome; stiff-person syndrome; stroke; Sturge-Weber syndrome; stuttering; subacute sclerosing panencephalitis; subcortical arteriosclerotic encephalopathy; superficial siderosis; Sydenham's chorea; syncope; synesthesia; syringomyelia; tarsal tunnel syndrome; tardive dyskinesia; tardive dysphrenia; Tarlov cyst; Tay-Sachs disease; temporal arteritis; temporal lobe epilepsy; tetanus; tethered spinal cord syndrome; Thomsen disease; thoracic outlet syndrome; tic douloureux; Todd's Paralysis; tourette syndrome; toxic encephalopathy; transient ischemic attack; transmissible spongiform encephalopathies; transverse myelitis; traumatic brain injury; tremor; trichotillomania;

trigeminal neuralgia; tropical spastic paraparesis; trypanosomiasis; tuberous sclerosis; 22q13 deletion syndrome; Unverricht-Lundborg disease; vestibular schwannoma (acoustic neuroma); Von Hippel-Lindau disease (VHL); viliuisk encephalomyelitis (VE); Wallenberg's syndrome; west syndrome; whiplash; Williams syndrome; Wilson's disease; y-linked hearing impairment; and/or Zellweger syndrome.

CNS or PNS Injury or Trauma

Injury in the CNS or PNS (e.g., trauma to the CNS or PNS, crush injury, SCI, TBI, stroke, optic nerve injury, or related conditions that involve axonal disconnection) may be treated with the compositions and methods as described herein. The CNS includes the brain and the spinal cord and the PNS is composed of cranial, spinal, and autonomic nerves that connect to the CNS.

Damage to the nervous system caused by mechanical, thermal, chemical, or ischemic factors may impair various nervous system functions such as memory, cognition, language, and voluntary movement. Most often, this is through accidental crush or transection of nerve tracts, or as an unintended consequence of medical therapy for cancer using chemotherapy. This results in the interruption of communication between nerve cell bodies and their targets. Other types of injuries may include disruption of the interrelations between neurons and their supporting cells or the destruction of the blood-brain barrier.

As described herein, mitofusin activators rapidly reverse mitochondrial dysmotility in neurons from mice with various genetic neurodegenerative diseases and in axons injured or severed by physical injury. For this reason, it is believed that enhancing mitochondrial trafficking with mitofusin activators may enhance regeneration/repair of physically damaged nerves, as in vehicular and sports injuries, penetration trauma from military or criminal actions, and inatrogenic injury during invasive medical procedures. Further testing of the injury-regeneration hypothesis will be further developed with the small molecule mitofusin activators for evaluation of their in vivo effectiveness. As such, the present disclosure provides for compositions and methods to treat physical nerve injury.

As disclosed herein, mitochondria motility was implicated in neuropathy. It is believed that mitochondrial motility is also implicated in nerve injuries, especially in nerves that have not severed, such as a crush injury. After an accident or crush injury, nerves will regenerate or die. Small molecule mitofusin activators, as described herein, may increase mitochondrial trafficking, enabling the nerve to regenerate after a crush injury.

Formulation

The agents and compositions described herein may be formulated by any conventional manner using one or more pharmaceutically acceptable carriers or excipients as described previously (e.g., Remington's Pharmaceutical Sciences (A. R. Gennaro, Ed.), 21st edition, ISBN: 0781746736 (2005), which is incorporated herein by reference with respect to its disclosure of pharmaceutically acceptable carriers). Such formulations will contain a therapeutically effective amount of a biologically active agent described herein, which may be in purified form, together with a suitable amount of carrier to provide the form for proper administration to a subject.

The term "formulation" refers to a preparation of a drug in a form suitable for administration to a subject such as a human. Thus, a "formulation" may include pharmaceutically acceptable excipients, including diluents or carriers.

The term "pharmaceutically acceptable," as used herein, describes substances or components that do not cause unacceptable losses of pharmacological activity or unacceptable adverse side effects. One of skill in the art will be familiar with suitable pharmaceutically acceptable substances. Examples of pharmaceutically acceptable ingredients include those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF may also be used.

The term "pharmaceutically acceptable excipient," as used herein, includes solvents, dispersion media, coatings, antibacterial agents, antifungal agents, isotonic, and absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients may also be incorporated into the compositions.

A "stable" formulation or composition refers to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

A formulation should suit the desired mode of administration. The agents of use with the current disclosure may be formulated by known methods for administration to a subject using several routes including, but not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations may also be used to affect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period. In order to maintain a near-constant level of an agent in the body, the agent may be released from the dosage form at a rate that will replace the amount of agent being metabolized or excreted from the body. The controlled-release of an agent may be stimulated by various inducers (e.g., change in pH, change in temperature, enzymes, water, or other physiological conditions or molecules).

Agents or compositions described herein may also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided herein is a process of treating a mitochondria-associated disease, disorder, or condition in a subject in need of administration of a therapeutically effective amount of mitofusin activator to prevent or treat a mitochondria-associated disease, disorder, or condition.

For example, the compositions and methods described herein may be used as a primary therapy for Charcot-Marie-Tooth or as an adjunctive therapy for Huntington's disease, Parkinson's disease, Alzheimer's disease, or ALS to retard or reverse disease progression.

As another example, the compositions and methods described herein may be used for the treatment of a physical injury. For example, as a primary therapy for any contusive injury involving the spine or peripheral nerves (perhaps even the brain, i.e., concussion), such as motor vehicle or sports injuries. This therapy may help restore normal motor function by augmenting regeneration and repair of injured neurons.

Methods described herein are generally performed on a subject in need thereof. A subject in need of the therapeutic methods described herein may be a subject having, diagnosed with, suspected of having, or at risk for developing a mitochondria-associated disease, disorder, or condition. A determination of the need for treatment will typically be assessed by a history and physical exam consistent with the disease or condition at issue. Diagnosis of the various conditions treatable by the methods described herein is within the skill of the art. The subject may be an animal subject, including a mammal, such as horses, cows, dogs, cats, sheep, pigs, mice, rats, monkeys, hamsters, guinea pigs, chickens, and humans. For example, the subject may be a human subject.

Generally, a safe and effective amount of a mitofusin activator is, for example, that amount that would cause the desired therapeutic effect in a subject while minimizing undesired side effects. In various aspects, an effective amount of a mitofusin activator described herein may substantially inhibit mitochondria-associated disease, disorder, or condition, slow the progress of mitochondria-associated disease, disorder, or condition, or limit the development of mitochondria-associated disease, disorder, or condition. For example, a desired therapeutic effect may be a delay in peripheral neuropathy (e.g., over the course of three years) compared to placebo assessed by slower increase in modified composite CMT neuropathy score. As another example, a desired therapeutic effect may be reversal or absence of progression of peripheral neuropathy compared to placebo, as indicated by lower or stable modified composite CMT neuropathy score. As yet another example, a desired therapeutic effect may be reversal or absence of progression of dysregulated motor function or increased regeneration and repair of injured neurons.

According to the methods described herein, administration may be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a mitofusin activator may be employed in pure form or, where such forms exist, in pharmaceutically acceptable salt form and with or without a pharmaceutically acceptable excipient. For example, the compounds of the present disclosure may be administered, at a reasonable benefit/risk ratio applicable to any medical treatment, in a sufficient amount to treat, prevent, or slow the progression of mitochondria-associated disease, disorder, or condition.

The amount of a composition described herein that may be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein may be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that may be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, may benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating may also include inhibiting the state, disease, disorder, or condition (e.g., arresting or reducing the development of the disease or at least one clinical or subclinical symptom thereof). Furthermore, treating may include relieving the disease (e.g., causing regression of the state, disease, disorder, or condition or at least one of its clinical or subclinical symptoms). A benefit to a subject to be treated may be either statistically significant or at least perceptible to the subject or to a physician.

Administration of a mitofusin activator may occur as a single event or over a time course of treatment. For example, a mitofusin activator may be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For chronic conditions, treatment could extend from several weeks to several months or even years.

Treatment in accord with the methods described herein may be performed prior to, concurrent with, or after conventional treatment modalities for treating, preventing, or slowing the progression of mitochondria-associated disease, disorder, or condition.

A mitofusin activator may be administered simultaneously or sequentially with another agent, such as an antibiotic, an anti-inflammatory, or another neuroregenerative agent. For example, a mitofusin activator may be administered simultaneously with another agent, such as an antibiotic or an anti-inflammatory. Simultaneous administration may occur through administration of separate compositions, each containing one or more of a mitofusin activator, an antibiotic, an anti-inflammatory, or another agent. Simultaneous administration may occur through administration of one composition containing two or more of mitofusin activator, an antibiotic, an anti-inflammatory, or another agent. A mitofusin activator may be administered sequentially with an antibiotic, an anti-inflammatory, or another agent. For example, a mitofusin activator may be administered before or after administration of an antibiotic, an anti-inflammatory, or another agent.

Administration

Agents and compositions described herein may be administered according to methods described herein in a variety of means known to the art. The agents and composition may be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration may be parenteral, pulmonary, oral, topical, transdermal (e.g., a transdermal patch) intradermal, intramuscular, intraperitoneal, intravenous, subcutaneous, intranasal, epidural, ophthalmic, buccal, or rectal administration.

Agents and compositions described herein may be administered in a variety of methods well known in the arts. Administration methods may include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump that may be used to administer the agent or composition in a manner similar to that used for delivering insulin or chemotherapy to specific organs or tumors. Typically, using such a system, an agent or composition may be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system may be placed in proximity of a therapeutic target, thus requiring only a fraction of a systemic dosage.

Agents may be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Screening

Also provided are methods for screening. As described herein, an imaging method for screening and evaluating small molecular or other regulators of mitochondrial fusion is provided.

The term "mitochondrial fusion," as used herein, refers to the physical merging and transfer of components between two or more previously distinct mitochondria.

Mitochondrial fusion is distinct from an increase in mitochondrial "aspect ratio" (the ratio of the mitochondrial long/short axis, or mitochondrial length/width) because it is impossible to discriminate between increases in mitochondrial aspect ratio that occur due to increased mitochondrial fusion versus, for example, decreased mitochondrial fission.

With the mitofusin activators that have been shown to activate mitochondrial fusion, assays may be designed and performed to screen candidate agents or molecules for specific compositions that may activate mitochondrial fusion per se. For example, identification of small molecule mitofusin activators provides an alternate modulating composition that may be more efficient to synthesize and use. Candidate agents encompass numerous chemical classes, typically synthetic, semi-synthetic, or naturally-occurring inorganic or organic molecules. Candidate agents include those found in large libraries of synthetic or natural compounds. Alternatively, libraries of natural compounds in the form of bacterial, fungal, plant and animal extracts are available from commercial resources or are readily producible. In some aspects, mitofusin activators or other small molecule activators of mitochondrial fusion identified through these screening assays may become promising therapeutic agents for treating diseases or disorders associated with defects in mitochondrial fusion.

A screening assay for mitochondrial fusion may use a mitochondrial-targeted photoswitchable fluorophore genetically introduced into cultured cells expressing any complement of mammalian mitofusins (e.g., both MFN1 and MFN2 [wild-type], MFN1 alone [MFN2 null], MFN2 alone [MFN1 null], or neither MFN1 nor MFN2 [MFN1/MFN2 double null]). In this assay, cells constitutively expressing the photoswitchable mitochondrial fluorophore are cultured on microscope slides or on the well surfaces of a high throughput screen plate. Patterned laser illumination of the cells promotes photo switching in a matrix pattern, which converts half of the mitochondria in each cell from green to red fluorescence. Photo switched cells are then incubated with vehicle (negative control), mitofusin activators (positive control), or unknown compounds for increasing periods of time (e.g., a fraction of an hour, 1 hour, 2 hours, 3 hours, or multiples thereof). A candidate agent is assessed for its ability to stimulate co-localization of red and green fluorescence within the same mitochondria, visually assessed via microscopy or automated imaging as the presence of yellow (green+red) mitochondria in the same cell. An agent that stimulates mitochondrial fusion will increase red/green colocalization at a given time point after treatment. A candidate agent able to promote red/green mitochondrial colocalization 30%, 50%, or >70% greater than vehicle, or comparable (within 50% at similar doses) to a validated mitofusin activator, may activate mitochondrial fusion.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 1000 Da) organic molecules or inorganic molecules including, but not limited to, salts or metals.

Candidate molecules encompass numerous chemical classes, for example, organic molecules, such as small organic compounds having a molecular weight of more than 50 Da and less than about 2,500 Da. Candidate molecules may comprise functional groups necessary for structural interaction with proteins, particularly hydrogen bonding, and typically include at least an amine, carbonyl, hydroxyl or carboxyl group, and usually at least two of the functional chemical groups. The candidate molecules may comprise cyclical carbon or heterocyclic structures and/or aromatic or polyaromatic structures substituted with one or more of the above functional groups.

A candidate molecule may be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character xlogP of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 KDa to about 500 kDa) with relatively more numerous features (e.g., less than about ten hydrogen acceptors and/or less than about eight rotatable bonds; hydrophobicity character xlogP of less than about 5) (see e.g., Lipinski (2000) J. Pharm. Tox. Methods 44, 235-249). Initial screening may be performed with lead-like compounds.

When designing a lead from spatial orientation data, it may be useful to understand that certain molecular structures are characterized as being "drug-like." Such characterization may be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical success if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they may serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Da; (ii) a log of P less than 5; (iii) no more than five hydrogen bond donors (expressed as the sum of —OH and —NH groups); and (iv) no more than ten hydrogen bond acceptors (the sum of N and O atoms). In addition, drug-like molecules typically have a span (breadth) of between about 8 Å to about 15 Å.

Fragment-based lead discovery (FBLD) also known as fragment-based drug discovery (FBDD) is a method that may be used for finding lead compounds as part of the drug discovery process. It is based on identifying small chemical fragments, which may bind only weakly to the biological target, and then growing them or combining them to produce a lead with a higher affinity. FBLD may be compared with high-throughput screening (HTS). In HTS, libraries with up to millions of compounds, with molecular weights of around 500 Da, are screened, and nanomolar-binding affinities are sought. In contrast, in the early phase of FBLD, libraries with a few thousand compounds with molecular weights of around 200 Da may be screened, and millimolar affinities may be considered useful.

In analogy to the rule of five, it has been proposed that ideal fragments could follow the 'rule of three' (molecular weight <300 Da, ClogP <3, the number of hydrogen bond donors and acceptors each should be less than three and the number of rotatable bonds should be less than three). Since the fragments have relatively low affinity for their targets, they should have high water solubility so that they may be screened at higher concentrations.

In fragment-based drug discovery, the low binding affinities of the fragments may pose significant challenges for screening. Many biophysical techniques have been applied to address this issue. In particular, ligand-observe nuclear magnetic resonance (NMR) methods such as water-ligand observed via gradient spectroscopy (waterLOGSY), saturation transfer difference spectroscopy (STD-NMR), $19^F$ NMR spectroscopy and inter-ligand Overhauser effect (ILOE) spectroscopy, protein-observe NMR methods such as $^1H/^{15}N$ heteronuclear single quantum coherence (HSQC) that utilizes isotopically-labelled proteins, surface plasmon resonance (SPR) and isothermal titration calorimetry (ITC) are routinely-used for ligand screening and for the quantification of fragment binding affinity to the target protein.

Once a fragment (or a combination of fragments) have been identified, protein X-ray crystallography may be used to obtain structural models of the protein-fragments) complexes. Such information may then be used to guide organic synthesis for high-affinity protein ligands and enzyme inhibitors.

Advantages of screening low molecular weight fragment based libraries over traditional higher molecular weight chemical libraries may include:

(i) More hydrophilic hits in which hydrogen bonding is more likely to contribute to affinity (enthalpically driven binding). It is generally much easier to increase affinity by adding hydrophobic groups (entropically driven binding); starting with a hydrophilic ligand increases the chances that the final optimized ligand will not be too hydrophobic (log P<5).

(ii) Higher ligand efficiency so that the final optimized ligand will more likely be relatively low in molecular weight (MW<500 Da).

(iii) Since two to three fragments in theory may be combined to form an optimized ligand, screening a fragment library of N compounds is equivalent to screening N2-N3 compounds in a traditional library.

Fragments may be less likely to contain sterically blocking groups that interfere with an otherwise favorable ligand-protein interaction, increasing the combinatorial advantage of a fragment library even further.

Kits

Also provided herein are kits. Such kits may include an agent or composition described herein and, in certain aspects, instructions for administration. Such kits may facilitate performance of the methods described herein. When supplied as a kit, the different components of the composition may be packaged in separate containers and admixed immediately before use. Components include, but are not limited to MFN1, MFN2, antactivator target peptides, activator target peptides, or mitofusin activators. Such packaging of the components separately can, if desired, be presented in a pack or dispenser device, which may contain one or more unit dosage forms containing the composition. The pack may, for example, comprise metal or plastic foil such as a blister pack. Such packaging of the components separately may also, in certain instances, permit long-term storage without losing activity of the components.

Kits may also include reagents in separate containers (e.g., sterile water or saline) to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that may be pierced by a hypodermic injection needle. Other containers may have two compartments that are separated by a readily removable membrane that upon removal permits the components to mix. Removable membranes may be glass, plastic, rubber, and the like.

In certain aspects, kits may be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols may be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some aspects, numbers expressing quantities of ingredients, properties such as molecular weight, reaction conditions, and so forth, used to describe and claim certain aspects of the present disclosure are to be understood as being modified in some instances by the term "about." In some features, the term "about" is used to indicate that a value includes the standard deviation of the mean for the device or method being employed to determine the value. In some features, the numerical parameters set forth in the written description and attached claims are approximations that may vary depending upon the desired properties sought to be obtained by a particular feature. In some aspects, the numerical parameters should be construed in light of the number of reported significant digits and by applying ordinary rounding techniques. Notwithstanding that the numerical ranges and parameters setting forth the broad scope of some aspects of the present disclosure are approximations, the numerical values set forth in the specific examples are reported as precisely as practicable. The numerical values presented in some aspects of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some aspects, the terms "a" and "an" and "the" and similar references used in the context of describing a particular aspect (especially in the context of certain of the following claims) may be construed to cover both the singular and the plural, unless specifically noted otherwise. In some aspects, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are open-ended. For example, any method that "comprises," "has" or "includes" one or more steps is not limited to possessing only those one or more steps and may cover other unlisted steps. Similarly, any composition or device that "comprises," "has" or "includes" one or more features is not limited to possessing only those one or more features and may cover other unlisted features.

All methods described herein may be performed in any suitable order unless otherwise indicated herein or otherwise clearly contradicted by context. The use of any and all examples, or exemplary language (e.g., "such as") provided with respect to certain aspects herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements, embodiments, aspects, or features of the present disclosure disclosed herein are not to be construed as limitations. Each group member may be referred to and claimed individually or in any combination with other members of the group or other elements found herein. One or more members of a group may be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments, features, or aspects are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus may be considered to constitute examples of modes for its practice. However, those of skill in the art should, in light of the present disclosure, appreciate that many changes may be made in the specific features that are disclosed and still obtain a like or similar result without departing from the spirit and scope of the present disclosure.

Example 1: Identification of Amino Acid Residues in the HR1 MFN1 and MFN2 Domain that Influence Conformation The following example shows that MFN1 and MFN2 conformation is influenced by a plurality of amino acid residues in the first heptad repeat (HR1) domain.

Mitochondria generate ATP that fuels neuronal activity. Mitochondrial dysfunction is implicated in chronic degenerative neurological conditions such as Alzheimer's, Parkinson's, and Huntington's diseases. Mitochondria fuse in order to exchange genomes and promote mutual repair. The initial stages of mitochondrial fusion proceed through the physio-chemical actions of two closely related dynamin family GTPases, mitofusins (MFN) 1 and 2. The obligatory first step leading to mitochondrial fusion is molecular tethering of two mitochondria via homo- or hetero-oligomerization (in trans) of extended MFN1 or MFN2 carboxyl termini. Subsequently, GTP binding to and hydrolysis by MFN1 or MFN2 promotes irreversible physical fusion of the organellar outer membranes. The genetic neurodegenerative condition, Charcot-Marie-Tooth Disease (type 2A) (CMT2A) or hereditary motor and sensory neuropathy, is caused by any of over 50 loss-of-function mutations of MFN2. The underlying mechanism that causes this debilitating neuropathy is impaired mitochondrial fusion and trafficking due to dominant inhibition of normal MFN1 and MFN2 by the mutant protein. Currently, there is no disease-altering treatment for CMT2A.

MFN1 and MFN2 share a common domain structure, which was modeled using I-TASSER and structural homology with bacterial dynamin-like protein (closed conformation), and OPA-1 (open conformation; see e.g., FIG. 1). As shown in the structural modeling of MFN2 in FIG. 1, MFN2 may be in its putative closed (left, inactive) and open (right, active) conformations. Critical peptide-peptide interactions between alpha-helices in MFN2 heptad repeat region 1 (HR1) and MFN2 heptad repeat region 2 (HR2) are expanded in red balloon inset. HR1 367-384 (inset) is agonist peptide MP-1 (Franco et al Nature 2016), which competes with endogenous peptide-peptide interactions at HR2 to force MFN1 and MFN2 opening and activation. The model shows how the first heptad repeat domain (HR1) interacts in an anti-parallel manner with the carboxyl terminal second heptad repeat (HR2) domain to restrain protein unfolding and extension into the cytosol, which is a prerequisite for mitochondrial fusion and trafficking (see e.g., FIG. 1). The amino acids necessary for the HR1-HR2 interaction were identified as Met376, His380, and Met 381 by first defining a minimal HR1-derived peptide that competes with endogenous HR1-HR2 binding, followed by functional analyses of a complete series of alanine substituted peptides (Rocha et al 2018 Science 360:336). Based on these results, a pharmacophore model was developed to screen and identify chemical peptidomimetics that mimic the 3-dimensional spatial and charge characteristics of these critical amino acid side chains. Phosphorylation of Ser378 on the HR1 domain regulates the orientation of Met376, His380, and Met 381, regulating the peptide-peptide interaction that maintains the closed protein conformation.

Example 2: Chemical Peptidomimetics of the Minimal MFN2 HR1 Peptide May Be Mitofusin Activators. Screening of commercially available compounds that conformed to the mini-peptide pharmacophore model identified compounds A and B. compound A (EC50 about 30 nM) was markedly less effective and potent as a mitofusin activator than compound B (EC50 about 10 nM) (Rocha et al 2018 Science 360:336).

The efficacy and synergy of the prototype mitofusin activators were enhanced (EC50 about 3 nM) by engineering chimeric compounds incorporating features of the parental compound A and B molecules (see e.g., TABLES 1, 2, and 3 in the reference). However, suboptimal pharmacokinetic characteristics of this series of compounds (e.g., rapid degradation by liver microsomes and/or impermeability to blood brain barrier/blood nerve barrier) precluded their use as clinical therapeutics.

Figure 2:
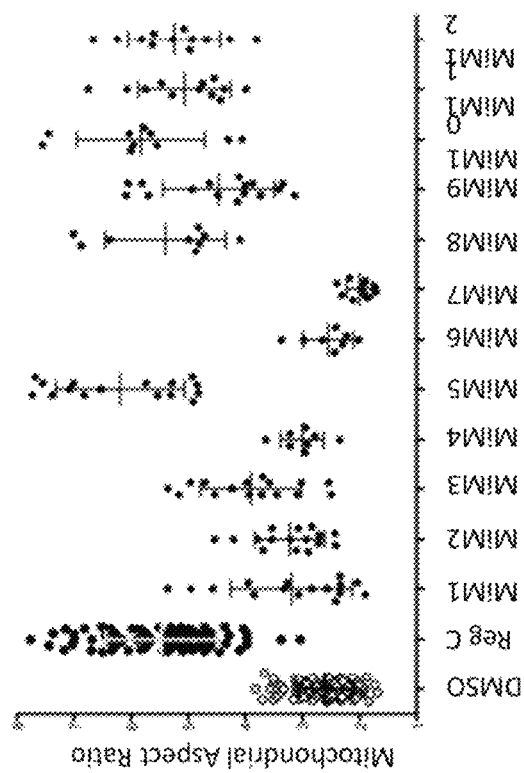
FIG. 2 depicts a series of chemical structures for a new class of urea-based mitofusin activators and a dot plot graph that shows the function of each new compound expressed as the mitofusin-dependent mitochondrial elongation provoked by each in comparison with the prototype of the previously described class of small molecule mitofusin activators, Reg C.
Figure 2:
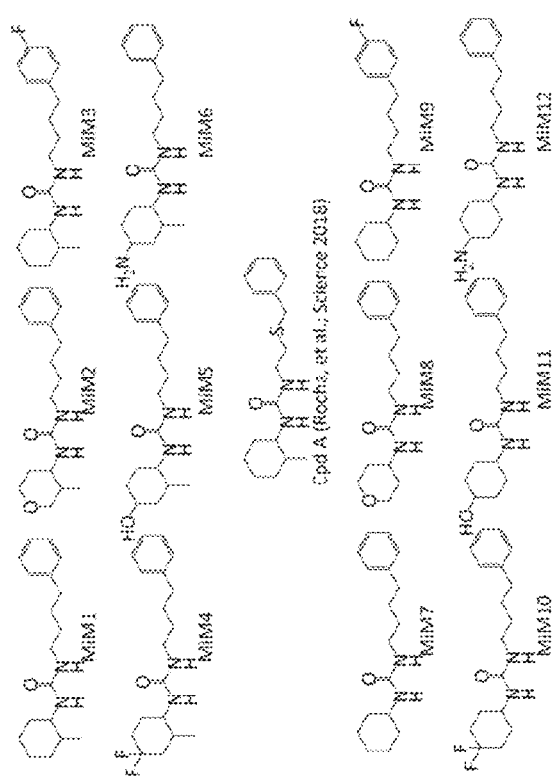
Figure 3:
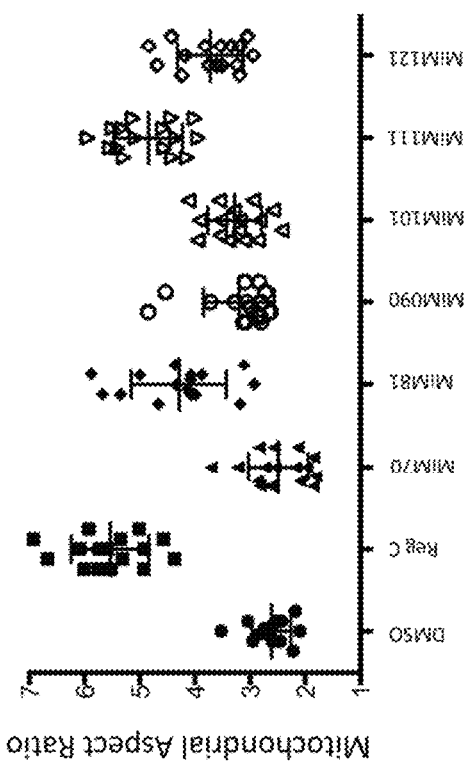
FIG. 3 depicts a series of chemical structures for yet another new class of amide-based mitofusin activators and a dot plot graph that shows the function of each new compound expressed as the mitofusin-dependent mitochondrial elongation provoked by each in comparison with the prototype of the previously described class of small molecule mitofusin activators, Reg C.
Figure 3:
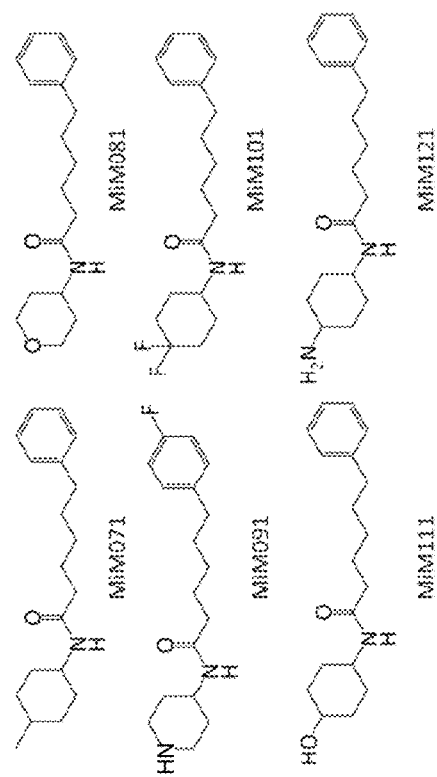
Figure 4:
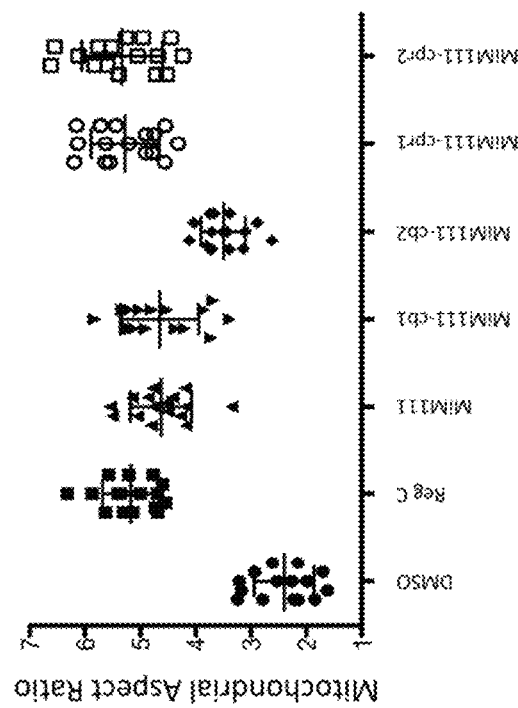
FIG. 4 depicts a series of chemical structures for yet another new class of amide-based cyclic backbone mitofusin activators and a dot plot graph that shows the function of each new compound expressed as the mitofusin-dependent mitochondrial elongation provoked by each in comparison with the prototype of the previously described class of small molecule mitofusin activators, Reg C.
Figure 4:
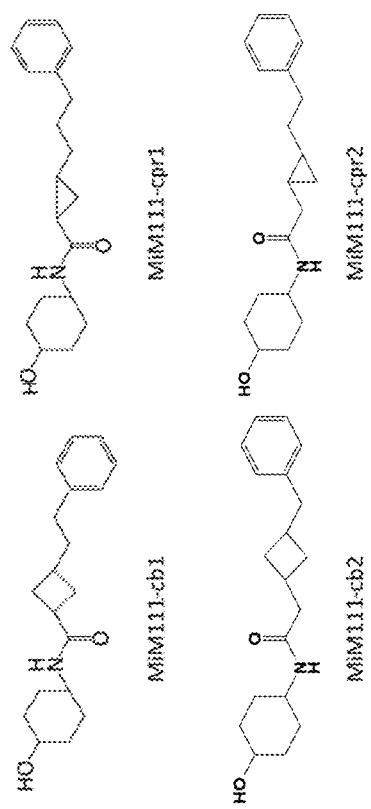
Figure 5:
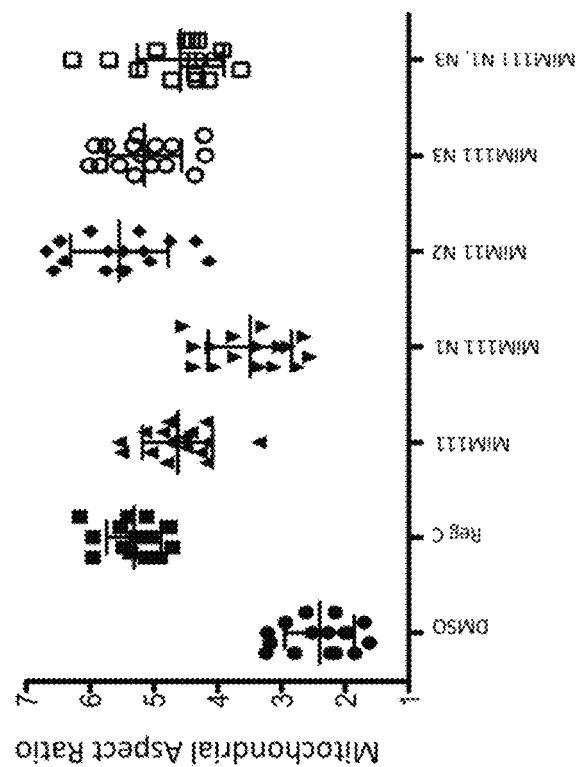
FIG. 5 depicts a series of chemical structures for yet another new class of amide-based mitofusin activators containing a heteroaromatic group and a dot plot graph that shows the function of each new compound expressed as the mitofusin-dependent mitochondrial elongation provoked by each in comparison with the prototype of the previously described class of small molecule mitofusin activators, Reg C.
Figure 5:
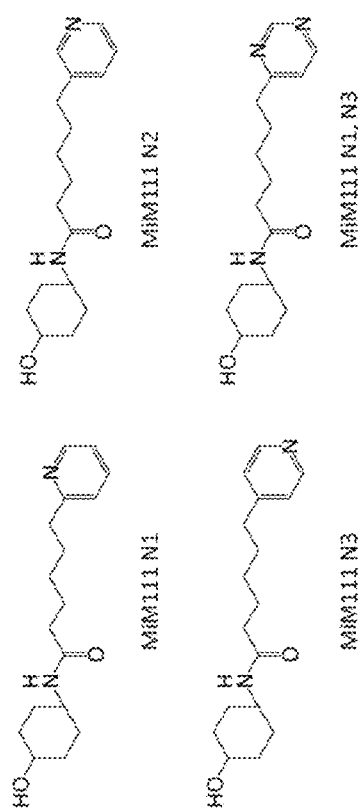

Example 3: Chemical Modifications of Compound A Provide for Mitofusin Activators with Enhanced Potency and Superior Pharmacokinetic Properties. Compound A was re-engineered to enhance its pharmacophore characteristics, resulting in a novel class of agents having potent fusogenic properties (EC50 about 3 nM), with an improved combination of stability in the liver microsome assay and passive permeability, which correlates with blood brain barrier permeability (see e.g., FIGS. 2-5). FIG. 2 shows improved novel mitofusin agonists modified from parent compound A (Rocha *Science* 2018) with urea containing backbones, the right panel shows results of functional screening; DMSO is vehicle and Reg C is positive control mitofusin agonist. MiM5 and MiM8-MiM12 are highly active. MiM10, MiM11, and MiM12 exhibited average EC50 values of 5 nm, 40.84 nM, and 5 nm, respectively. Urea backbone compounds were generally synthesized according to Scheme 1 below. FIG. 3 shows improved mitofusin activators modified from parent compound A (Rocha Science 2018) having amide backbones, the right panel shows results of functional screening; DMSO is vehicle and Reg C is positive control mitofusin agonist. MiM81, MiM101 and MiM111 exhibited average EC50 values of 19.41, 46.93 and 8.18 nM, respectively. MiM121 exhibited an average EC50 of 6.3 nm. Amide backbone compounds were generally synthesized by Scheme 2 below. FIG. 4 shows improved amide mitofusin activators modified from parent compound A (Rocha Science 2018) having cyclic backbone structures, the right panel shows results of functional screening; DMSO is vehicle and Reg C is positive control mitofusin agonist. All compounds except MiM111 cb2 were highly active. Cyclic backbone compounds containing an amide were synthesized by a modification of Scheme 2 below, after obtaining an appropriate phenyl-substituted cycloalkyl carboxylic acid. MiM111cpr1, MiM111cpr2, and MiM111cb1 exhibited average EC50 values of 5.1, 5.9 and 18 nM, respectively. FIG. 5 shows improved amide mitofusin activators modified from parent compound A (Rocha Science 2018) having pyridine or pyridimine substitutions, the right panel shows results of functional screening; DMSO is vehicle and Reg C is positive control mitofusin agonist. All compounds except MiM111 N1 were highly active. MiM111 N2, MiM111 N3, MiM111 N4, and MiM111 N1, N3 exhibited average EC50 values of 23.15, 4.14, 1.27 and 4.58 nM, respectively. Pyridine backbone compounds containing an amide were likewise synthesized by a modification of Scheme 2 below, optionally after synthesizing an appropriate pyridinehexanoic acid or pyrimidinehexanoic acid (Scheme 3). In addition, Table 1 below shows MiM111 reversal of neuromuscular degeneration in a mouse model of neurodegenerative Charcot-Marie-Tooth disease type 2A as measured by Rotarod testing.

TABLE 1

|  | Benchmark | MiM111 |
|---|---|---|
| Calculated Properties | | |
| Molecular Weight (g/mol) | <400 | 289.4 |
| Calculated log P | <3 | 3.22 |
| TPSA (A) | <100 | 49.33 |
| LE | >0.4 | 0.52 |
| LLE | >5 | 4.82 |
| Rotatable Bond # | <10 | 7 |
| HBD | <5 | 4 |
| HBD + HBA | <10 | 2 |
| Fsp3 | >45% | 61% |
| Functional Properties | | |
| EC50 Mito Elongation (nM) | <30 | 9 |
| Selectivity | >10 ∞M; 30-fold | 100-fold |
| In Vivo PK/PD | | |
| CNS Elimination $t_{1/2}$ (hours) | >3 | 3.4 (ss) |
| Plasma $t_{1/2}$ (hours) | >1 | 2.22 (oral) |
| Oral Bioactivity | >50% | 75.50% |
| In Vitro DPMK | | |
| Plasma Stability (120 min.) H | >90% | 87% |
| M | >90% | 100% |
| Plasma Protein % Bound H | <90% | 91% |
| M | <90% | 96.30% |
| Solubility | >40 ∞M | 175 ∞M |
| Liver Microsomes $t_{1/2}$ (minutes) H | >100 | >145 |
| M | >100 | 92.4 |
| PAMPA (Pe, nm/s) | >10 | 26.277 |
| P-gp eflux Ratio | >3 | 1.74 |
| In Vitro Toxicology | | |
| Cyp450 IC50 ∞M | >30 | >50, all 5 |
| hERG VC (% inhib. 10∞M) | <25 | 1.56% |
| Ames Test | negative | negative |

TABLE 1-continued

| | Benchmark | MiM111 |
|---|---|---|
| In Vivo Toxicology | | |
| MTD (48 hours, mg/kg) | >100 | |
| MTD (4 weeks) | no liver, renal, CNS | no 30 mg/kg/day |
| MTD (2 months) | no liver, renal, CNS | |
| MTD (6 months) | no liver, renal, CNS | |

This class of mitofusin activators has characteristics making it superior as an in vivo treatment for CMT2A, ALS, other neurodegenerative conditions, and nerve injury.

Figure 6C:
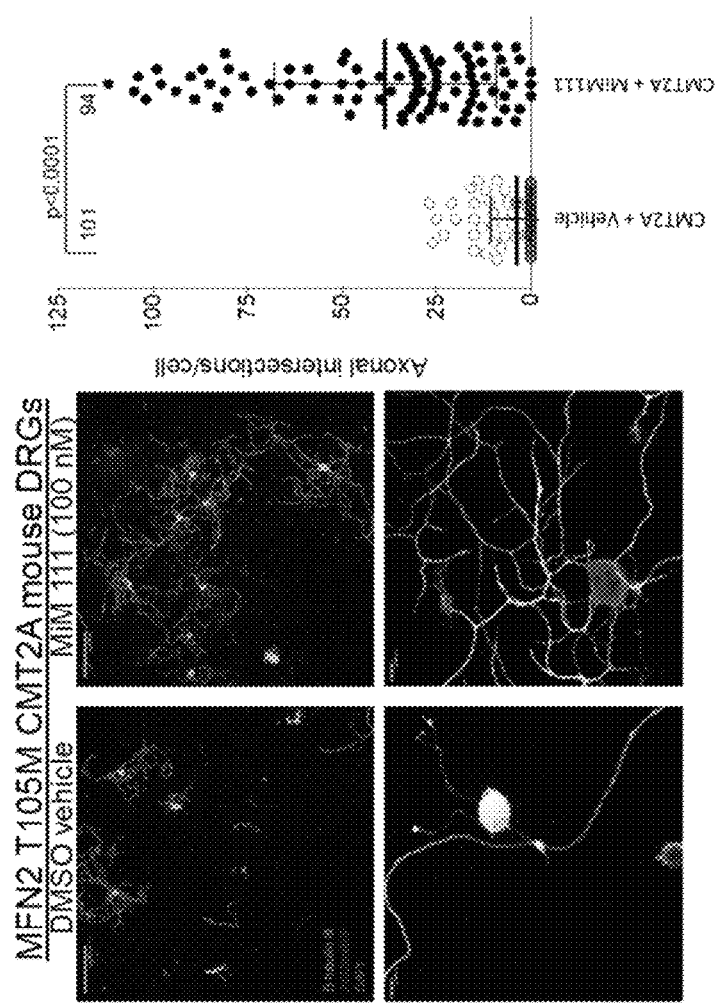
FIG. 6C shows that MiM111 promotes regrowth of mouse Charcot-Marie-Tooth 2A dorsal root ganglion neurons in culture and may reverse disease in mouse model of Charcot-Marie-Tooth disease type 2A.
Figure 7B:
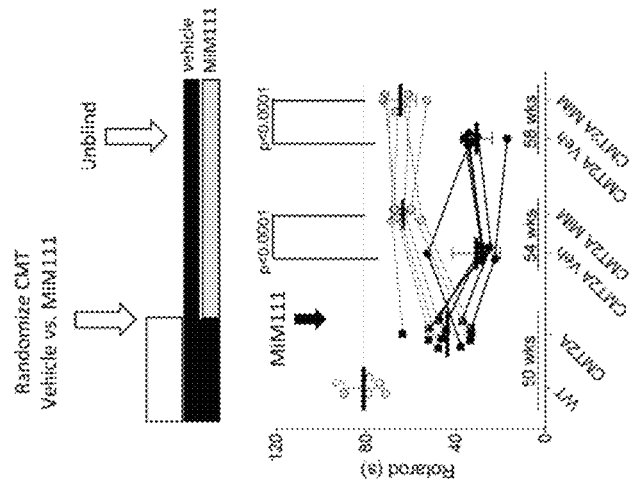
FIG. 7B shows the results, in which MiM111 reversed a Rotarod defect in all treated mice within 8 weeks of treatment (statistics used 2-way ANOVA).
Figure 7A:
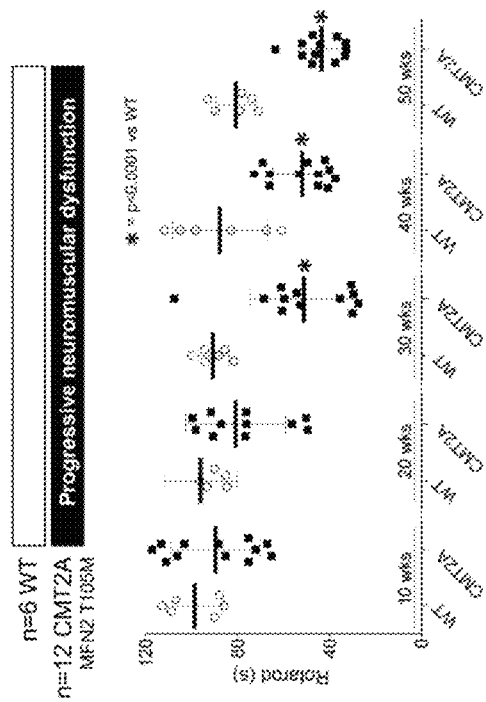
FIG. 7A illustrates an example of MiM111 reversing defects in experimental CMT2A in a graph where the schematics at top show experimental design and the dot blots at bottom show results.

Example 4: The Mitofusin Activator MiM111 Corrects Mitochondrial Defects and Neuromuscular Dysfunction in Experimental Models of CMT2A. MiM111 is a pharmaceutically acceptable cyclohexanol/amide derivative of Compound A (see e.g., FIGS. 2-5 and Table 1). In particular, Table 1 above shows representative biological and physiochemical assays of MiM111 activity on mitofusin 2 and on CMT2A neurons. Like structurally dissimilar Chimera C, MiM111 is potent (EC50 about 9 nM), induces an open conformation of its target MFN2, and promotes neuronal regrowth/regeneration in vitro (see e.g., FIGS. 6A-6C). FIGS. 6A-6C illustrate how MiM111 is a potent mitofusin activator and promotes neuronal regeneration. FIG. 6A shows the dose-response relations of MiM5, MiM11, and MiM111 compared to prototype Chimera compound described in Rocha et al *Science* 2018. FIG. 6B shows the MiM111 conformational opening of mitofusin 2 mimics that of agonist peptide described in Franco et al *Nature* 2016. FIG. 6C shows how MiM111 promotes regrowth of mouse Charcot-Marie-Tooth 2A dorsal root ganglion neurons in culture. In a humanized mouse model of CMT2A wherein human mutant MFN2 T105M is expressed in motor neurons, MiM111 acutely corrected characteristic sciatic nerve mitochondrial immobility and, when administered chronically, reversed neuromuscular dysfunction (see e.g., FIGS. 7A-7B). FIGS. 7A-7B show an example of MiM111 reversing defects in experimental CMT2A. In FIG. 7A, the schematics at top show experimental design; dot blots at bottom show results. The CMT2A MFN2 T105M mouse recapitulates human CMT2A with progressive neuromuscular dysfunction, shown here by Rotarod latency (time to falling off). After murine CMT2A was fully developed at 50 weeks of age, mice were randomized to treatment with MiM111 or vehicle. FIG. 7B shows the results of MiM111 having reversed Rotarod defect in all treated mice within 8 weeks of treatment (the statistics used 2-way ANOVA).

Syntheses of Phenylbutyl Urea Backbone Compounds. Phenylbutyl urea compounds were generally synthesized by Scheme 1 below. Examples 5-8 are illustrative of the syntheses of these types of backbone compounds.

Scheme 1

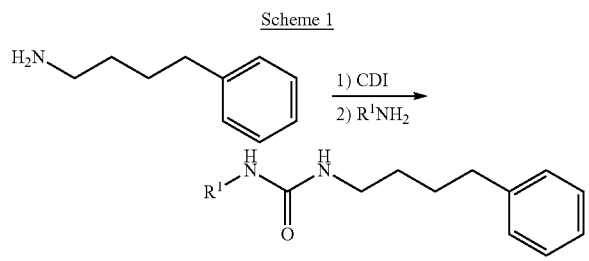

Example 5: 1-(2-Methylcyclohexyl)-3-(4-phenylbutyl) urea (MiM1). To a solution of 2-methylcyclohexan-1-amine (0.759 g, 6.70 mmol) and DIPEA (0.866 g, 6.70 mmol) in THF (10 mL) was added CDI (1.09 g, 6.70 mmol), and the mixture was stirred at 25° C. for 10 min. To the mixture was added 4-phenylbutan-1-amine (1.00 g, 6.70 mmol), and the mixture was stirred at 25° C. for 16 h. The crude product was purified by reverse-phase HPLC, the eluent was concentrated under reduced pressure, the mixture was filtered, and then the filter cake was washed with a saturated solution of NaHCO$_3$ (20 mL×2) and washed with H$_2$O (20 mL×2) to give the title compound (110.12 mg, 379.50 μmol, 5.72% yield, 99.4% purity) as a white solid. HPLC: RT=2.273 min, purity: 99.4%. LC-MS: RT=0.823 min, m/z=289.0 (M+1)$^+$. $^1$H NMR: 400 MHz MeOD δ 7.26-7.22 (m, 2H), 7.18-7.13 (m, 3H), 3.14 (t, J=3.60 Hz, 3H), 2.63 (t, J=7.6 Hz, 2H), 1.89-1.86 (m, 1H), 1.78-1.53 (m, 5H), 1.53-1.46 (m, 2H), 1.35-1.01 (m, 5H), 1.07-0.91 (m, 3H). $^{13}$C NMR: MeOD δ 161.222, 143.825, 129.509, 126.884, 56.169-48.164, 40.875, 40.093, 36.717, 35.935, 35.625, 31.149, 30.106, 27.122, 26.975, 19.809.

Example 6: 1-(4-Hydroxy-2-methylcyclohexyl)-3-(4-phenylbutyl)urea (MiM5). To a solution of 4-amino-3-methylcyclohexan-1-ol (1.50 g, 11.6 mmol) and DIPEA (1.00 g, 7.74 mmol, 1.35 mL) in THF (10 mL) was added CDI (1.26 g, 7.74 mmol), and the reaction mixture was stirred at 25° C. for 10 min. Then, 4-phenylbutan-1-amine (1.16 g, 7.74 mmol, 1.22 mL) was added to the reaction mixture and stirred at 25° C. for 16 h. The reaction mixture was poured into H$_2$O (10 mL) and extracted with EtOAc (5 mL×3), and the organic layers were dried over Na$_2$SO$_4$, filtered, and concentrated under reduced pressure to give a residue, which was purified by reverse-phase HPLC to obtain the title compound (1.63 g, 5.16 mmol, 66.6% yield) as a light yellow solid. HPLC: RT=2.22 min, purity: 96.3%. LC-MS: RT=1.988 min, m/z=305.2 (M+H)$^+$. $^1$H NMR: 400 MHz CDCl$_3$ δ 7.20-7.06 (m, 5H), 5.34 (s, 1H), 3.94-3.73 (m, 1H), 3.65-3.50 (m, 1H), 3.10 (t, J=7.2 Hz, 2H), 2.55 (t, J=7.2 Hz, 2H), 1.74-1.09 (m, 10H), 0.83 (d, J=6.8 Hz, 3H). $^{13}$C NMR: CDCl$_3$ δ 142.13, 142.06, 128.37, 125.80, 77.45-76.61, 69.85, 48.46, 40.46, 38.44, 35.53, 33.79, 29.75, 28.67, 18.41, 18.37.

Example 7; (4-Hydroxycyclohexyl)-3-(4-phenylbutyl) urea To a solution of 4-phenylbutan-1-amine (1.0 g, 6.70 mmol 1.06 mL) and DIPEA (866 mg, 6.70 mmol, 1.17 mL) in THF (10 mL) was added CDI (1.09 g, 6.70 mmol, 1.0 equiv), and the mixture stirred at 25° C. for 15 min. To the reaction mixture was added 4-aminocyclohexan-1-ol (772 mg, 6.70 mmol) and stirred at 25° C. for 23.5 h. The reaction mixture was concentrated and purified by reverse-phase HPLC (column: Phenomenex luna C$_{18}$ 250×50 mm×10 μm; mobile phase: [water (0.05% HCl)-ACN]; B %: 25-55%, 25 min) twice. The mixture was concentrated under reduced pressure and filtered, and the filter cake was washed with NaHCO$_3$ to give the title compound (620 mg, 1.62 mmol, 69.0% yield) as white solid. HPLC: RT=1.73 min, purity:

99.8%. LC-MS: RT=0.842 min, m/z=291.1 (M+1)⁺. ¹H NMR: 400 MHz MeOD δ 7.26-7.22 (m, 2H), 7.18-7.13 (m, 2H), 3.53-3.42 (m, 2H), 3.12 (t, J=7.0 Hz, 2H), 2.61 (d, J=7.6 Hz, 2H), 1.91 (d, J=10.0 Hz, 3H), 1.65-1.61 (m, 2H), 1.50-1.46 (m, 2H), 1.35-1.33 (m, 2H), 1.25-1.20 (m, 2H). ¹³C NMR: MeOD δ 160.800, 143.788, 129.554, 129.430, 126.875, 70.654, 40.842, 36.688, 34.998, 32.558, 31.083, 30.069.

Syntheses of Phenylhexanamide Backbone Compounds. Phenylhexanamide compounds were generally synthesized by Scheme 2 below. Examples 8-11 are illustrative of the syntheses of these types of backbone compounds.

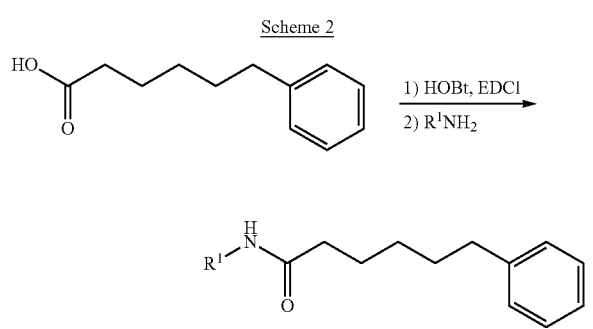

Scheme 2

Example 8: N-(Tetrahydro-2H-pyran-4-yl)-6-phenylhexanamide (MiM081)

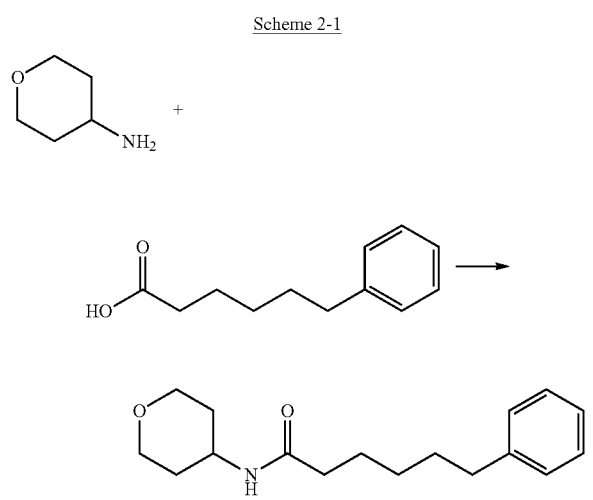

Scheme 2-1

Hydroxybenzotriazole (HOBt, 253 mg, 1.87 mmol, 1.20 eq.), 1-(3-dimethylaminopropyl)-3-ethylcarbodiimide (EDCI, 448 mg, 2.34 mmol, 1.50 eq.), and N,N-diisopropylethylamine (DIEA, 403 mg, 3.12 mmol, 543 μL, 2.00 eq.) were added to a solution of 6-phenylhexanoic acid (0.30 g, 1.56 mmol, 294 μL, 1.00 eq.) in DMF (3.0 mL). Then, tetrahydro-2H-pyran-4-amine (173 mg, 1.72 mmol, 1.10 eq.) was added to the reaction mixture. The reaction mixture was stirred at 25° C. for 3 h. The reaction mixture was concentrated under reduced pressure to give a residue. The residue was purified by preparative HPLC. The title compound (169.36 mg; 38% yield) was obtained as a white solid. MS: m/z=276.0 (M+H)⁺. ¹H NMR (400 MHz): DMSO-d₆ δ 7.72 (d, J=7.58 Hz, 1H) 7.08-7.33 (m, 5H) 3.65-3.86 (m, 3H) 3.31-3.36 (m, 2H) 2.55 (t, J=7.64 Hz, 2H) 2.03 (t, J=7.40 Hz, 2H) 1.64 (m, 2H) 1.53 (m, 4H) 1.20-1.40 (m, 4H). ¹³C NMR: DMSO δ 171.713, 142.682, 128.725-128.651, 126.043, 66.383, 45.129, 35.811-35.526, 33.039, 31.213, 28.661, 25.629.

Example 9: N-(Piperidin-4-yl)-6-phenylhexanamide (MiM091)

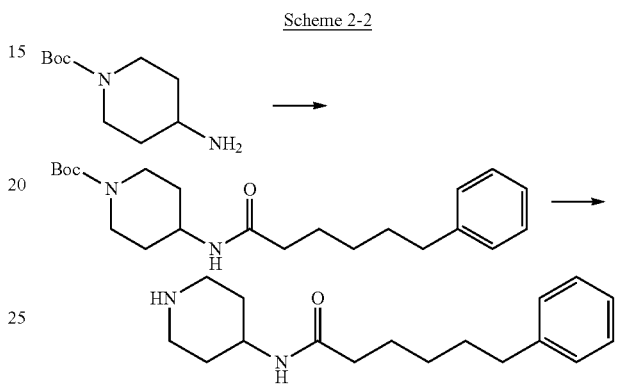

Scheme 2-2

HOBt (422 mg, 3.12 mmol, 1.20 eq.), EDCI (748 mg, 3.90 mmol, 1.50 eq.), and DIEA (672 mg, 5.20 mmol, 906 uL, 2.00 eq.) were added at 25° C. to a solution of tert-butyl 4-aminopiperidine-1-carboxylate (500 mg, 2.60 mmol, 490 μL, 1.00 eq.) and 6-phenylhexanoic acid (573 mg, 2.86 mmol, 1.10 eq.) in DMF (3.00 mL). The mixture was stirred at 25° C. for 12 h. The reaction mixture was diluted with H₂O (10.0 mL) and extracted with EtOAc (10.0 mL×2). The organic phase was adjusted to a pH of 4 with 1 M HCl and extracted with EtOAc (20.0 mL). The combined organic layers were adjusted to a pH of 8 with aqueous NaHCO₃. The combined organic layers were washed with brine (20.0 mL), dried over Na₂SO₄, filtered, and concentrated under reduced pressure to give a residue. The BOC-protected amide (740 mg; 76% yield) was obtained as a yellow solid. MS: m/z=319.3 (M+H)⁺. ¹H NMR (400 MHz): DMSO-d₆ δ 7.71 (d, J=7.8 Hz, 1H), 7.30-7.21 (m, 2H), 7.20-7.11 (m, 3H), 3.81 (br d, J=12.4 Hz, 2H), 3.73-3.62 (m, 1H), 2.90-2.71 (m, 2H), 2.54 (t, J=7.6 Hz, 3H), 2.02 (t, J=7.4 Hz, 2H), 1.69-1.60 (m, 2H), 1.59-1.46 (m, 4H), 1.39 (s, 9H), 1.28-1.11 (m, 3H).

HCl/MeOH (4 M, 12 mL, 24.3 eq.) was added to a solution of the BOC-protected amide (740 mg, 1.98 mmol, 1.00 eq. in MeOH (3 mL). The mixture was stirred at 25° C. for 16 h. The mixture was concentrated under reduced pressure to give a residue. The residue was purified by prepative HPLC. The title compound (418.27 mg; 73% yield) was obtained as a white solid. MS: m/z=275.1 (M+H)⁺. ¹H NMR (400 MHz): MeOD δ 7.25-7.22 (m, 2H), 7.17-7.13 (m, 3H), 3.81-3.76 (m, 1H), 3.14-3.11 (m, 2H), 2.79-2.78 (m, 2H), 2.76-2.75 (m, 2H), 2.60 (t, J=7.2 Hz, 2H), 2.16 (t, J=7.2 Hz, 2H), 1.88-1.85 (m, 2H), 1.65-1.61 (m, 2H), 1.61-1.46 (m, 4H), 1.46-1.35 (m, 2H), 1.35-1.33 (m, 2H). ¹³C NMR: MeOD δ 175.676, 143.873, 129.713, 129.582, 129.419, 126.827, 47.291, 45.424, 37.125, 36.856, 32.519, 32.274, 29.829, 27.040.

Example 10: N-(4,4-Difluorocyclohexyl)-6-phenylhexanamide (MiM101)

Scheme 2-3

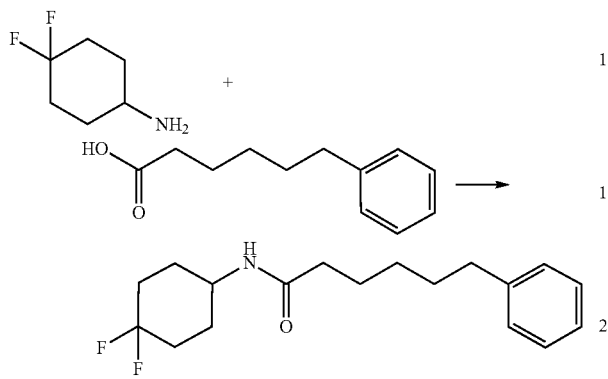

HOBt (253 mg, 1.87 mmol, 1.20 eq.), EDCI (448 mg, 2.34 mmol, 1.50 eq.), and DIEA (403 mg, 3.12 mmol, 543 µL, 2.00 eq.) were added to a solution of 4,4-difluorocyclohexylamine (300 mg, 1.56 mmol, 294 µL, 1.00 eq.) in DMF (3.0 mL). Then, 6-phenylhexanoic acid (232 mg, 1.72 mmol, 1.10 eq.) was added to the mixture. The mixture was stirred at 25° C. for 3 h. The mixture was concentrated under reduced pressure to give a residue. The residue was purified by preparative HPLC. The title compound (98.23 mg; 20% yield) was obtained as a white solid. MS: m/z=310.1 (M+H)$^+$. $^1$H NMR (400 MHz): DMSO-d$_6$ δ 7.72 (d, J=7.58 Hz, 1H), 7.13-7.28 (m, 5H), 3.72 (d, J=7.58 Hz, 1H), 2.55 (t, J=7.58 Hz, 2H), 2.01-2.06 (m, 2H), 1.68-2.00 (m, 6H), 1.48-1.61 (m, 4H), 1.39-1.48 (m, 2H), 1.24 (m, 2H). $^{13}$C NMR: DMSO-de δ 171.949, 142.682, 128.733-128.659, 126.059, 45.072, 35.778, 35.518, 31.727, 31.197, 28.621, 28.482, 28.384, 25.620.

Example 11: N-(4-hydroxycyclohexyl)-6-phenylhexanamide (MiM111). The chemical synthesis of an advanced lead, designated MiM111, is described here and illustrated in Scheme 2-4 and Scheme 2-5 below.

Scheme 2-4

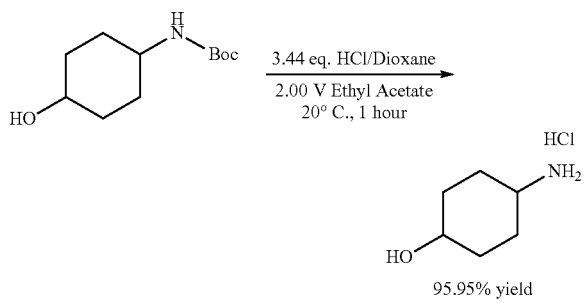

95.95% yield

To a solution of 4-(t-butoxycarbonylamino)cyclohexanol (9.00 g, 41.8 mmol, 1.00 eq.) in ethyl acetate (18.0 mL) was added HCl/dioxane (4 M, 36.0 mL, 3.44 eq.). The mixture was stirred at 20° C. for 1 h. Thin layer chromatography (TLC, petroleum ether/ethyl acetate=1/2) showed complete consumption of the starting material (R$_f$=0.50), and a new main spot (R$_f$=0.02) was formed. The mixture was filtered and the resulting filter cake was washed with ethyl acetate (10.0 mL×3), filtered, and concentrated under reduced pressure to obtain a residue, which was used in the next step without further purification. 4-aminocyclohexanol hydrochloride (6.08 g, 40.1 mmol, 95.9% yield, HCl salt) was obtained as off-white solid.

Scheme 2-5

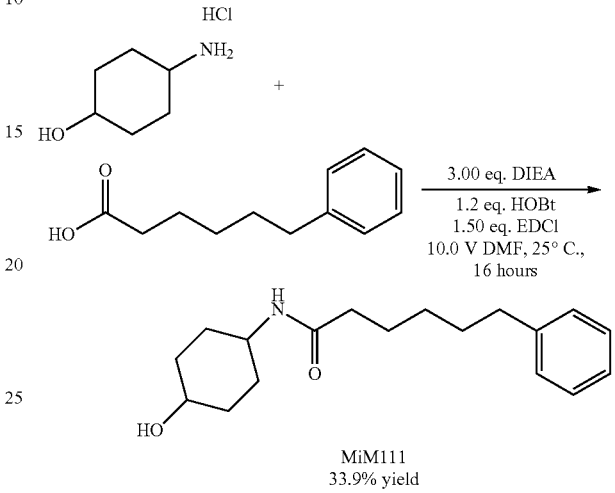

MiM111
33.9% yield

Phenylhexanoic acid (6.92 g, 36.0 mmol, 6.78 ml, 1.00 eq.), HOBt (5.83 g, 43.2 mmol, 1.20 eq.) and EDCI (10.3 g, 54.0 mmol, 1.50 eq.) were added to a solution of 4-aminocyclohexanol hydrochloride (6.00 g, 39.6 mmol, 1.10 eq., HCl salt) and DIEA (14.0 g, 108 mmol, 18.8 ml, 3.00 eq.) in N,N-dimethylformamide (DMF, 60.0 mL). The mixture was stirred at 25° C. for 16 h. Liquid chromatography with mass spectrometric detection (LCMS, EW18054-2-P1A3) showed complete consumption of the phenylhexanoic acid and the desired MS(R$_t$=0.684 min, 0.709 min) was detected. The reaction mixture was diluted with ethyl acetate (300 mL) and washed with saturated brine (150 mL×5). The combined organic layer was washed with 1N HCl (48.0 mL), dried over anhydrous Na$_2$SO$_4$, filtered, and the filtrate was concentrated under reduced pressure to obtain a residue. The residue was purified by preparative HPLC (column: Phenomenex LUNA® C18 250×80 mm×10 µm; mobile phase: [water (10 mM NH$_4$HCO$_3$)-ACN]; B %: 38% ACN-68% ACN, 8.5 min) to obtain a residue following solvent removal. The residue was triturated with a 5:1 mixture of petroleum ether:ethyl acetate (240 mL) at 25° C. for 5 minutes to obtain MiM111 (3.53 g, 12.0 mmol, 33.9% yield, 99.93% purity) as an off-white solid.

After drying, products were characterized by LCMS, $^1$H NMR, and $^{13}$C NMR. HPLC: EW18054-2-P1A, product: R$_t$=10.792 min, purity: 99.93% under 210 nm.

High-resolution mass spectrometry (HRMS): RT=1.884 min, m/z=290.2128 (M+H)$^+$. $^1$H NMR: 400 MHz MeOD δ 7.25-7.22 (m, 2H), 7.16-7.11 (m, 3H), 3.59-3.48 (m, 2H), 2.60 (t, J=7.6 Hz, 2H), 2.13 (t, J=7.4 Hz, 2H), 1.92-1.65 (m, 4H), 1.65-1.59 (m, 4H), 1.35-1.29 (m, 6H), $^{13}$C NMR: MeOD δ 175.669, 143.887, 129.595, 126.817, 70.605, 37.240, 36.869, 34.973, 32.517, 31.668, 29.814, 27.102.

Syntheses of Pyridylhexanamide or Pyrimidinylhexanamide Backbone Compounds. Pyridylhexanamide or pyrimidinylhexanamide compounds were generally synthesized by a modification of Scheme 2 above. Pyrimidinylhexanoic acid was generally synthesized by Scheme 3 below. Examples 12-15 are illustrative of the syntheses of these types of backbone compounds.

Scheme 3

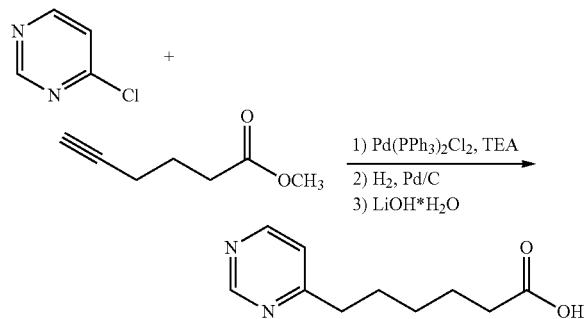

Example 12: (4-Hydroxycyclohexyl)-6-(pyridin-2-yl)hexanamide (MiM111 N1). To a solution of 6-(pyridin-2-yl)hexanoic acid (1.09 g, 5.64 mmol) in DMF (10 mL) were added HOBt (914 mg, 6.77 mmol), EDCI (1.62 g, 8.46 mmol), and DIEA (2.19 g, 16.9 mmol, 2.95 mL). Then, 4-aminocyclohexan-1-ol (940 mg, 6.20 mmol, 1.10 equiv, HCl) was added to the mixture and stirred at 25° C. for 16 h, and the residue was purified by reverse-phase HPLC (column: Waters Xbridge C18 150×50 mm×10 μm; mobile phase: [water (10 mM NH4HCO3)-ACN]; B %: 7-37%, 10 min) to obtain the title compound (106.1 mg, 355 μmol, 6.30% yield) as an off-white solid. HPLC: RT=1.78 min, purity: 97.2%. LC-MS: RT=0.752 min, m/z=291.0 (M+H)$^+$. $^1$H NMR: 400 MHz MeOD, δ 8.42 (d, J=4.00 Hz, 1H), 7.77-7.73 (m, 1H), 7.31-7.30 (m, 1H), 7.25-7.23 (m, 1H), 3.61-3.48 (m, 2H), 2.80-2.76 (m, 2H), 2.16-2.12 (m, 2H), 1.91-1.91 (m, 2H), 1.72-1.70 (m, 2H), 1.65-1.63 (m, 2H), 1.61-1.61 (m, 2H), 1.37-1.33 (m, 4H), 1.32-1.26 (m, 2H). $^{13}$C NMR: MeOD. δ 175.538, 163.333, 149.597, 138.868, 124.829, 122.881, 70.591, 38.666, 37.133, 34.973, 31.671, 30.954, 29.861, 27.016.

Example 13: (4-Hydroxycyclohexyl)-6-(pyridin-3-yl)hexanamide (MiM111 N2). To a solution of 6-(pyridin-3-yl)hexanoic acid (594 mg, 3.07 mmol) in DMF (10 mL) were added HOBt (498 mg, 3.69 mmol), EDCI (883 mg, 4.61 mmol), and DIEA (1.19 g, 9.22 mmol, 1.61 mL). Then, 4-aminocyclohexan-1-ol (512 mg, 3.38 mmol, HCl) was added to the mixture, and the mixture was stirred at 25° C. for 16 h. LC-MS showed consumption of the starting material and formation of the desired product. The reaction was diluted with H$_2$O (20 mL) and extracted with ethyl acetate (10 mL×3). The combined organic layers were washed with brine (10 mL×3), dried over Na$_2$SO$_4$, filtered, and concentrated under reduced pressure to give a residue. The residue was purified by reverse-phase HPLC (column: Waters Xbridge C18 150×50 mm×10 μm; mobile phase: [water (10 mM NH$_4$HCO$_3$)-ACN]; B %: 7-37%, 10 min) to afford the title compound (100.5 mg, 346 μmol, 11.2% yield) as an off-white solid. HPLC: RT=1.53 min, purity: 99.9%. LC-MS: product: RT=0.763 min, m/z=291.0 (M+H)$^+$. $^1$H NMR: 400 MHz MeOD, δ 8.38-8.37 (m, 1H), 8.35-8.34 (m, 1H), 7.70 (d, J=8.0 Hz, 1H), 7.36-7.33 (m, 1H), 3.59-3.49 (m, 2H), 2.68-2.65 (m, 2H), 2.16-2.12 (m, 2H), 1.92-1.92 (m, 2H), 1.68-1.65 (m, 2H), 1.65-1.61 (m, 4H), 1.36-1.35 (m, 4H), 1.32-1.26 (m, 2H). $^{13}$C NMR: MeOD δ 175.513, 150.200, 147.599, 140.262, 138.436, 125.286, 70.575, 37.109, 34.973, 33.734, 32.038, 31.671, 29.690, 26.926.

Example 14: (4-Hydroxycyclohexyl)-6-(pyridin-4-yl)hexanamide (MiM111 N3). To a solution of 6-(pyridin-4-yl)hexanoic acid (100 mg, 517 μmol) in DMF (1.00 mL) were added EDCI (149 mg, 776 μmol), HOBt (83.9 mg, 621 μmol), and DIEA (201 mg, 1.55 mmol, 270 μL). Then, 4-aminocyclohexan-1-ol (86.3 mg, 569 μmol, HCl) was added to the mixture and stirred at 25° C. for 16 h. LC-MS showed consumption of the starting material and formation of the desired product. The mixture was purified by reverse-phase HPLC (column: Waters Xbridge C18 150×25 mm×5 μm; mobile phase: [water (10 mM NH4HCO3)-ACN]; B %: 8-38%, 10 min), and the title compound (43.73 mg, 149 μmol, 28.9% yield) was obtained as a white solid. HPLC: RT=1.50 min, purity: 99.7%. LC-MS: RT=0.748 min, m/z=291.1 (M+H)$^+$. $^1$H NMR: 400 MHz MeOD, δ 8.40-8.38 (m, 2H), 7.29-7.27 (m, 2H), 3.61-3.48 (m, 2H), 2.67 (t, J=7.6 Hz, 2H), 2.14 (t, J=7.2 Hz, 2H), 1.95-1.91 (m, 2H), 1.87-1.84 (m, 2H), 1.68-1.61 (m, 4H), 1.36-1.35 (m, 2H), 1.35-1.26 (m, 4H). $^{13}$C NMR: MeOD, δ 175.505, 154.685, 149.937, 125.853, 125.853, 70.580, 37.100, 36.045, 34.965, 31.668, 31.182, 29.723, 26.896.

Example 15: (4-Hydroxycyclohexyl)-6-(pyrimidin-4-yl)hexanamide (MiM111 N1,N3). To a solution of 4-chloropyrimidine (1.00 g, 6.62 mmol, HCl), CuI (63.1 mg, 331 μmol), Pd(PPh3)$_2$Cl$_2$ (232 mg, 331 μmol), and TEA (2.01 g, 19.9 mmol, 2.77 mL) in DMF (10.0 mL) was added methyl hex-5-ynoate (835 mg, 6.62 mmol, 1.00 equiv). The mixture was stirred at 20° C. for 16 h, and methyl 6-(pyrimidin-4-yl)hex-5-ynoate (740 mg, 3.33 mmol, 50.3% yield, 91.9% purity) was obtained as a yellow oil.

To a solution of 6-(pyrimidin-4-yl)hex-5-ynoate (740 mg, 3.33 mmol, 1.00 equiv) in MeOH (10.0 mL) was added Pd/C (74.0 mg, 10%) under N$_2$. The mixture was stirred at 25° C. for 16 h under H$_2$ (15 psi), and methyl 6-(pyrimidin-4-yl)hexanoate (734 mg, crude) was obtained as a yellow oil.

To a solution of methyl 6-(pyrimidin-4-yl)hexanoate (734 mg, 3.52 mmol, 1.00 equiv) in THF (3.00 mL), MeOH (3.00 mL), and H$_2$O (3.00 mL) was added LiOH.H$_2$O (296 mg, 7.05 mmol, 2.00 equiv). The mixture was stirred at 25° C. for 16 h, and 6-(pyrimidin-4-yl)hexanoic acid (1.20 g, crude) was obtained as a yellow solid.

To a solution of 6-(pyrimidin-4-yl)hexanoic acid (1.20 g, 6.18 mmol) in DMF (12.0 mL) were added EDCI (1.78 g, 9.27 mmol), HOBt (1.00 g, 7.41 mmol), and DIPEA (2.40 g, 18.5 mmol, 3.23 mL). Then, 4-aminocyclohexan-1-ol (1.03 g, 6.80 mmol, HCl) was added to the mixture, and the mixture was stirred at 25° C. for 16 h. LC-MS showed consumption of the starting material and formation of the desired product. The mixture was diluted with H$_2$O (50 mL) and extracted with EtOAc (50 mL×3). The combined organic layers were dried over Na$_2$SO$_4$, filtered, and concentrated under reduced pressure to give a residue. The residue was purified by reverse-phase HPLC (column: Phenomenex Gemini C18 250×50 mm×10 μm; mobile phase: [water (10 mM NH$_4$HCO$_3$)-ACN]; B %: 10-30%, 15 min), and the title compound (90.98 mg, 312 μmol, 5.05% yield) was obtained as an off-white solid. HPLC: RT=1.14 min, purity: 99.9%. LC-MS: RT=0.657 min, m/z=292.1 (M+H)$^+$. $^1$H NMR: 400 MHz MeOD, δ 9.02 (s, 1H), 8.65 (d, J=5.2 Hz, 1H), 7.43 (d, J=5.2 Hz, 1H), 3.59-3.48 (m, 2H), 2.79 (t, J=7.6 Hz, 2H), 2.15 (t, J=7.6 Hz, 2H), 1.95-1.92 (m, 2H), 1.88-1.84 (m, 2H), 1.80-1.72 (m, 2H), 1.68-1.60 (m, 2H), 1.40-1.35 (m, 2H), 1.33-1.19 (m, 4H). $^{13}$C NMR: MeOD, δ 175.475, 172.851, 159.152, 158.089, 122.490, 70.588, 38.344, 37.050, 34.965, 31.676, 29.781, 29.682, 26.888.

Example 16: A Live Cell Mitochondrial Fusion Assay for High Throughput Screening and Evaluation of Candidate Fusogenic Compounds. The following examples describe a live-cell fusogenicity assay suitable for directly measuring modulated mitochondrial fusion, and the consequences of mitofusin activation on mitochondria, in a high-throughput manner. This assay is superior to previous read-outs for fusogenicity of compounds, such as mitochondrial aspect ratio/elongation measured by confocal imaging, and mitofusin conformation assessed by FRET (Rocha et al 2018 Science 360:336), because it directly measures fusion of mitochondria whereas the conventional assays only infer fusion from indirect measures.

The small molecules described herein enhance mitochondrial fusion by destabilizing the folded conformation of MFN1 or MFN2, thus promoting initial tethering and subsequent membrane fusion between neighboring mitochondria. Mitochondrial fusion is essential for, and actively promotes, exchange of mitochondrial contents including protein, lipids, and DNA. The live cell assay quantifies mitochondrial fusion by measuring the time-dependent rate of mitochondrial protein exchange. This assay was specifically designed to screen for and evaluate the fusogenic properties (the ability of an agent to promote mitochondrial fusion) of candidate agents of any chemical class, or molecules with specific alternate compositions, including large libraries of synthetic or natural compounds.

Mitochondrial elongation, typically reported as the increase in mitochondrial aspect ratio (long axis dimension/short axis dimension), is a standard indirect metric of mitochondrial fusion. The live cell fusion assay simultaneously measures mitochondrial elongation/aspect ratio, permitting concomitant dual read-outs (e.g., mitochondrial content exchange and mitochondrial elongation) of mitochondrial fusion.

Mitochondrial tethering and outer membrane fusion may be evoked by activated MFN1, MFN2, or both. The live cell fusion assay is designed to determine if altered fusion is mediated by mitofusins, and if fusogenic compounds affect MFN1 and MFN2 differently, by measuring mitochondrial content exchange and elongation stimulated by screening compounds in cell with both MFN1 and MFN2, is cell having only one or the other MFN, and in cells totally lacking MFN activity.

Mitochondrial fusion in live cells has been demonstrated by assaying content exchange of cells with adenovirus-promoted expression of either mitochondrial-targeted green fluorescent protein (mito-GFP) or mitochondrial-targeted red fluorescent protein (mito-RFP) after poly-ethylene glycol (PEG) mediated cell fusion (Franco et al Nature 2016, 540:74). This PEG fusion assay system was limited by variable transient expression of the adenoviral mitochondrial targeted fluorescent proteins, highly variable cell fusion in response to PEG, and extremely low throughput (single cell analysis over time using confocal imaging).

These problems were solved by engineering the photoswitchable (green/red) mitochondrial-targeted fluorphore mito-Dendra2 (Pham et al Genesis 2012, 50:833) into a lentiviral expression vector for permanent, constitutive expression. Murine fibroblasts expressing both MFN1 and MFN2, MFN1 only, MFN2 only, or neither MFN1 nor MFN2 were transformed with the mito-Dendra2 lentivirus, propogated for 2 weeks, and selected for high level expression by fluorescence-activated cell sorting (FACS). Individual mito-Dendra-2 expressing cell lines with different mitofusin expression profiles were cloned and propogated for use in the screening assay.

Figure 8:
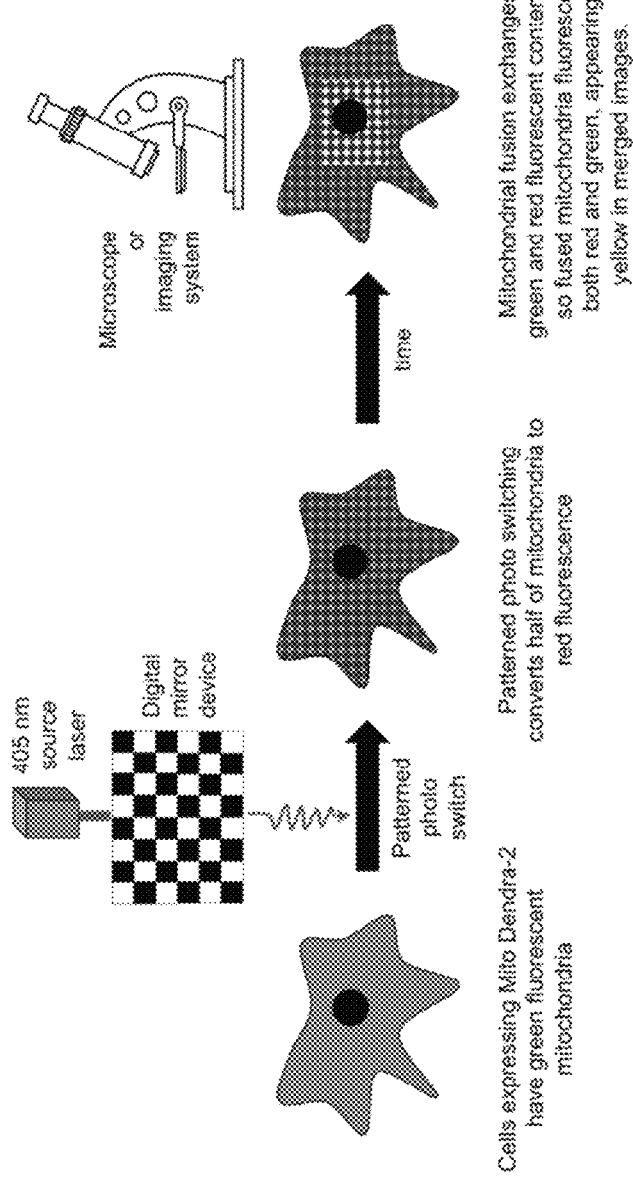
FIG. 8 is a schematic depiction of a method for measuring mitofusin-dependent mitochondrial fusion in a manner suitable for high-throughput screening or detailed quantitative analysis of mitofusin activator activity.
Figure 9:
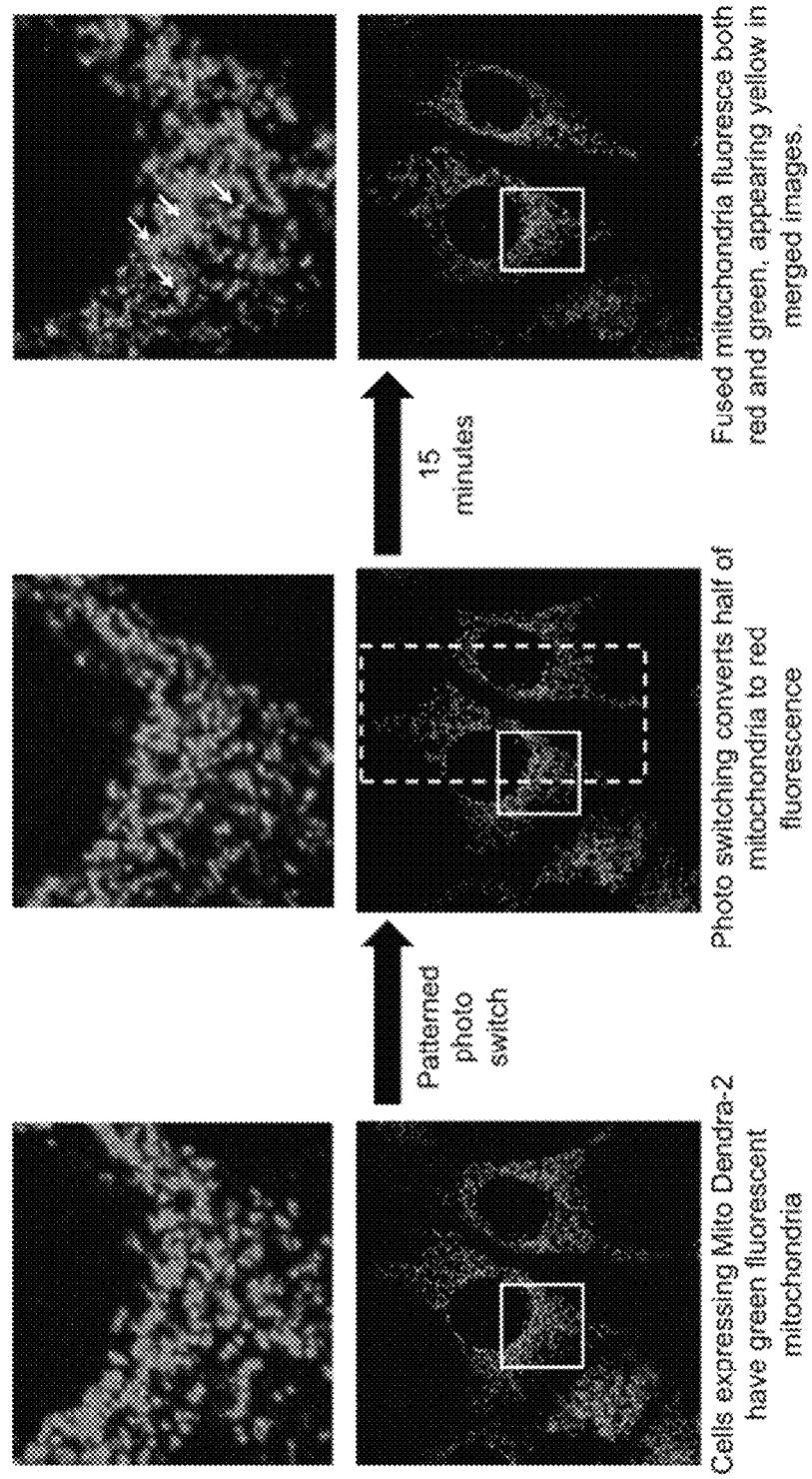
FIG. 9 shows results of mitochondrial fusion screening assay using the methods illustrated in FIG. 8.

The live cell mitochondrial fusion assay is initiated by patterned (e.g., 2×2 micron, 3×3 micron, 4×4 micron, etc) green-to-red mitochondrial photoswitching of cells using 405 nm frequency laser light. FIG. 8 is a schematic depiction of a patterned photo switching method for screening mitofusin-dependent mitochondrial fusion activity of small molecules, peptides, or nucleic acids. Patterned photoswitching is achieved using either a programmable microminiaturized mirror array (e.g., Polygon400 made by MIGHTEX) (see e.g., FIG. 8) for high throughput cell imaging or microscopy platforms, or using pixel scanning on standard confocal microscopes. Immediately after photoswitching, cells are treated with candidate fusogenic agents, vehicle (negative control), or positive control mitofusin activators. Two hours thereafter, or at different time points for time course analyses, cells are imaged for green mitochondrial fluorescence (488 nm excitation/535 nm emission) and red mitochondrial fluorescence (560 nm excitation/645 nm emission) using a high-throughput imaging system or confocal or standard fluorescence microscope. FIG. 9 shows an example of patterned photo switching (interrupted rectangle, middle panel) screen for mitochondrial fusion. Before photoswitching (left, D) cells expressing Mito Dendra-2 have green fluorescence (shown as bright white). Immediately after patterned 405 nm laser illumination (middle, E), the photo switching convers half of mitochondria to red fluorescence (shown as darker grey). Over time (15 minutes; right panel, F), green and red mitochondria will fuse, shown by arrows in merged images (right panel). The top images (A, B, and C) are enlarged from bottom (solid squares). Mitochondrial content exchange (i.e., fusion) is the overlap between red and green mitochondrial signals, which may be visualized as yellow fluorescence in merged images (shown as lighter grey) (see e.g., FIG. 9).

Data are represented as number of red-green overlay pixels (newly fused mitochondria) divided by red-green merged pixels (total mitochondria) at a given time point. Increased rate of fusion (red-green overly over time) in MFN expressing cells, but not MFN null cells, reflects a specific mitofusin activating effect. This system is useful in 12-, 24-, 96-, or 384-well formats for high-throughput screening of mitofusin activators.

Materials and Methods

Cell lines: Wild-type MEFs were prepared from E10.5 c57/bl6 mouse embryos. SV-40 T antigen-immortalized MFN1 null (CRL-2992), MFN2 null (CRL-2993) and MFN1/MFN2 double null MEFs (CRL-2994) were purchased from ATCC. MEFs were subcultured in DMEM (4.5 g/L glucose) plus 10% fetal bovine serum, 1× nonessential amino acids, 2 mM L-glutamine, 100 units/mL penicillin, and 100 µg/mL streptomycin.

Protein and Peptide Modeling: The hypothetical structures of human MFN2 were developed using the I-TASSER Suite package. The putative closed conformation is based on structural homology with bacterial dynamin-like protein (PDB: 2J69), human MFN1 (PDB:5GNS), and *Arabidopsis thaliana* dynamin-related protein (PDB: 3T34). The putative open conformation was based on structural homology with human Opa1, retrieved from the following structures: rat dynamin (PDB: 3ZVR), human dynamin 1-like protein (PDB: 4BEJ), and human myxovirus resistance protein 2 (PDB: 4WHJ). Minipeptide and protein modeling used PEP-FOLD3 (http://bioserv.rpbs.univ-paris-diderot.fr/services/PEP-FOLD3/) and UCSF Chimera, respectively.

Confocal Live Cell Studies of Mitochondria: Confocal imaging used a Nikon Ti Confocal microscope equipped with a 60×1.3NA oil immersion objective. All live cells were grown on cover slips loaded onto a chamber (Warner instrument, RC-40LP) in modified Krebs-Henseleit buffer (138 mM NaCl, 3.7 mM KCl, 1.2 mM $KH_2PO_4$, 15 mM Glucose, 20 mM HEPES and 1 mM $CaCl_2$) at room temperature.

Cells were excited with 408 nm (Hoechst), 561 nm (MitoTracker Green and Calcein AM, GFP), or 637 nm (TMRE, MitoTracker Orange, Ethidium homodimer-1, and AF594-Dextran) laser diodes. For mitochondrial elongation studies, mitochondrial aspect ratio (long axis/short axis) was calculated using automated edge detection and Image J software. Mitochondrial depolarization was calculated as percent of green mitochondria visualized on MitoTracker Green and TMRE merged images, expressed as green/(green+yellow mitochondria)×100.

Analytical Methods

HPLC/HRMS (ESP: LC/MS analysis was carried out using Agilent 1100 Series LC/MSD system with DAD\ELSD and Agilent LC\MSD VL (G1956A), SL (G1956B) mass-spectrometer or Agilent 1200 Series LC/MSD system with DAD\LSD and Agilent LC\MSD SL (G6130A), SL (G6140A) mass-spectrometer. All the LC/MS data were obtained using positive/negative mode switching. The compounds were separated using a Zorbax SB-C18 1.8 µm 4.6×15 mm Rapid Resolution cartridge (PN 821975-932) under a mobile phase (A—acetonitrile, 0.1% formic acid; B—water (0.1% formic acid)). Flow rate: 3 mL/min; Gradient 0 min—100% B; 0.01 min—100% B; 1.5 min—0% B; 1.8 min-0% B; 1.81 min—100% B; Injection volume 1 µL; Ionization mode atmospheric pressure chemical ionization (APCI); Scan range m/z 80-1000.

Statistical Methods

Time-course and dose-response data are calculated for each study using GraphPad Prism (La Jolla, Calif., USA). All data are reported as mean±SEM. Statistical comparisons (two-sided) used one-way ANOVA and Turkey's tests for multiple groups or Student's t-test for paired comparisons. p<0.05 was considered significant. In vitro pharmacokinetic analyses of mitofusin activators was performed at WuXi Apptec Co. Ltd. (Shanghai, China).

Binding to human and CD-1 mouse plasma proteins was measured using equilibrium dialysis. Pooled individual frozen EDTA anticoagulated plasma mouse and human samples were used as test matrix. Warfarin was used as a positive control. The test compounds were spiked into blank matrix at the final concentration of 2 µM. A 150-µL aliquot of matrix sample was added to one side of the chamber in a 96-well equilibrium dialyzer plate (HTD dialysis) and an equal volume of dialysis buffer was added to the other side of the chamber. An aliquot of matrix sample was harvested before the incubation and used as $T_0$ samples for recovery calculation. The incubations were performed in triplicate. The dialyzer plate was placed in a humidified incubator and rotated slowly for four hours at 37° C. After incubation, the samples were taken from the matrix side as well as the buffer side. The plasma sample was matched with equal volume of blank buffer; and buffer samples were matched with equal volume of blank plasma. The matrix-matched samples were quenched with stop solution containing internal standard. All samples were analyzed by LC-MS/MS. All test compound concentrations in matrix and buffer samples are expressed as peak area ratios (PAR) of analyte/internal standard.

Activator in vitro stability was measured in human and mouse liver microsomes. An intermediate solution (100 µM of small molecule) was initially prepared in methanol and subsequently used to prepare the working solution. This was achieved by a 10-fold dilution step of the intermediate solution in 100 mM potassium phosphate buffer. Ten µL of a compound working solution or control working solution was added to all wells of a 96-well plate for the time points (minutes): $T_0$, $T_5$, $T_{10}$, $T_{20}$, $T_{30}$, $T_{60}$, NCF60, except the matrix blank. The microsome solution (680 µL/well) (#452117, Corning; Woburn, Mass., USA; #R1000, Xenotech; Kansas City, Kans., USA and #M1000, Xenotech; Kansas City, Kans., USA) was dispersed to 96-well plate as reservoir according to the plate map. Then, 80 µL/well was added to every plate by ADDA (Apricot Design Dual Arm, Apricot Designs, Inc., Covina, Calif., USA), and the mixture of microsome solution and compound were allowed to incubate at 37° C. for about 10 minutes. Next, 10 µL of 100 mM potassium phosphate buffer/well was added to NCF60 and incubated at 37° C. (timer 1H was started). After pre-warming, 90 µL/well of NADPH (#00616, Sigma, Aldrich, St. Louis, Mo., USA) regenerating system was dispensed to 96-well plate as reservoir according to the plate map. Then 10 µL/well was added to every plate by ADDA to start reaction. To terminate the reaction, 300 µL/well of stop solution (cold in 4° C., including 100 ng/mL tolbutamide and 100 ng/mL labetalol as internal standards) was used, and sampling plates were agitated for approximately 10 min. The samples were next centrifuged at 4000 rpm for 20 minutes at 4° C. supernatants were analyzed by LC-MS/MS.

Parallel Artificial Membrane Permeability Assay (PAMPA).

A 10 µM solution of a small molecule in 5% DMSO (150 µL) was added to each well of the donor plate, whose PVDF membrane was pre-coated with 5 µL of 1% brain polar lipid extract (porcine)/dodecane mixture. Then, 300 µL of PBS was added to each well of the PTFE acceptor plate. The donor plate and acceptor plate were combined together and incubated for 4 hours at room temperature with shaking at 300 rpm. To prepare the $T_0$ sample, 20 µL of a donor solution was transferred to new well, followed by the addition of 250 µL PBS (DF:13.5) and 130 µL of acetonitrile (ACN) (containing internal standard) as the $T_0$ sample. To prepare the acceptor sample, the plate was removed from incubator and 270 µL of the solution was transferred from each acceptor well and mixed with 130 µL ACN (containing internal standard) as an acceptor sample. To prepare the donor sample, 20 µL of the solution was transferred from each donor well and mixed with 250 µL PBS (DF: 13.5), 130 µL ACN (containing internal standard) as a donor sample. The acceptor samples and donor samples were analyzed by LC-MS/MS.

The present invention is also directed to the following clauses.

Clause 1: A method of treating a peripheral nervous system (PNS) or central nervous system (CNS) genetic disorder, physical damage, and/or chemical injury, comprising:

administering to a subject a therapeutically effective amount of a composition comprising one or more of a mitofusin activator or a pharmaceutically acceptable salt thereof, wherein the mitofusin activator stimulates mitochondrial fusion and enhances mitochondrial subcellular transport.

Clause 2. The method of clause 1, wherein the composition comprises one or more mitofusin activators, wherein the mitofusin activator comprises a structure of formula:

(I)

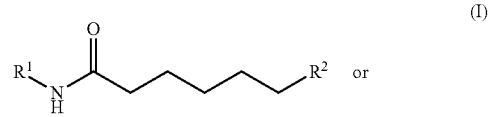

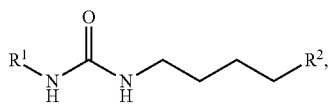

or a pharmaceutically acceptable salt, tautomer, or stereoisomer thereof, wherein $R^1$ is selected from non-, mono-, or poly-substituted $C_{3-8}$ cycloalkyl, $C_{3-8}$ heteroaryl, and $C_{3-8}$ heterocyclyl; and wherein $R^2$ is selected from non-, mono-, or poly-substituted $C_{3-8}$ cycloalkyl, $C_{3-8}$ heteroaryl, and $C_{3-8}$ heterocyclyl.

Clause 3. The method of clauses 1 or 2, wherein the mitofusin activator comprises a structure of formula:

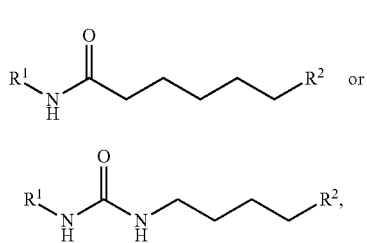

wherein $R^1$ is selected from

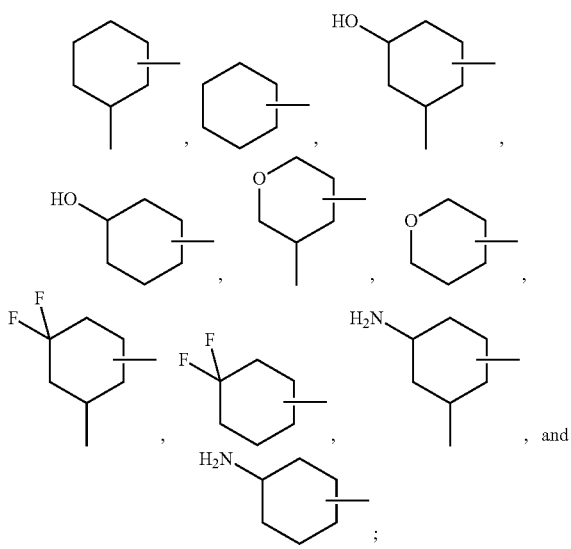

and wherein $R^2$ is selected from

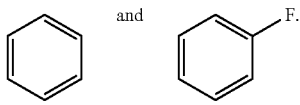 [SMILES: c1ccccc1 ; "and" ; Fc1ccccc1]

Clause 4: The method of clauses 2 or 3, wherein $R^1$ or $R^2$ are independently and optionally substituted by one or more of acetamide, $C_{1-8}$ alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, and/or thiophene;

wherein $R^1$ or $R^2$ are optionally further substituted with one or more acetamide, alkoxy, amino, azo, Br, $C_{1-8}$ alkyl, carbonyl, carboxyl, Cl, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, and/or thiophene; and wherein one or more of the alkyl, cycloalkyl, heteroaryl, heterocyclyl, indole, or phenyl substituent is optionally further substituted with one or more of the following substituents: acetamide, alkoxy, amino, azo, Br, $C_{1-8}$alkyl, carbonyl, carboxyl, $C_1$, cyano, $C_{3-8}$ cycloalkyl, $C_{3-8}$ heteroaryl, $C_{3-8}$ heterocyclyl, hydroxyl, F, halo, indole, N, nitrile, O, phenyl, S, sulfoxide, sulfur dioxide, and thiophene.

Clause 5: The method of any one of clauses 1 to 4, wherein the mitofusin activator is selected from:

-continued

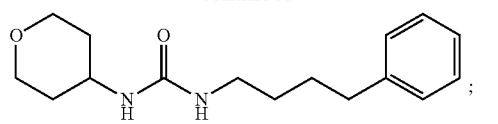

1-(4-phenylbutyl)-3-(tetrahydro-2H-pyran-4-yl)urea

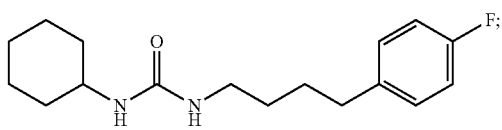

1-cyclohexyl-3-(4-(4-fluorophenyl)butyl)urea

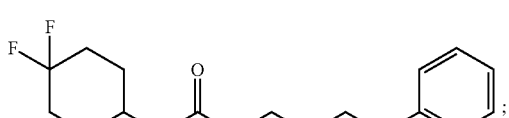

1-(4,4-difluorocyclohexyl)-3-phenylbutyl)urea

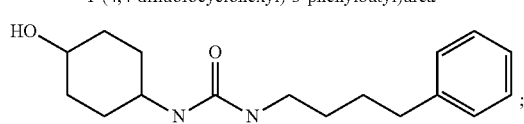

1-(4-hydroxycyclohexyl)-3-(4-phenylbutyl)urea

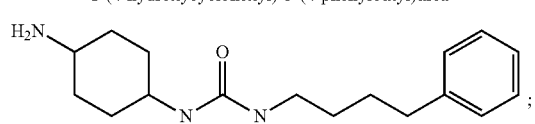

1-(4-aminocyclohexyl)-3-(4-phenylbutyl)urea

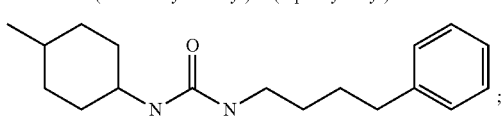

1-(4-methylcyclohexyl)-3-(4-phenylbutyl)urea

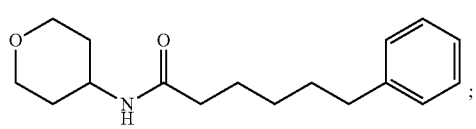

6-phenyl-N-(tetrahydro-2H-pyran-4-yl)hexanamide

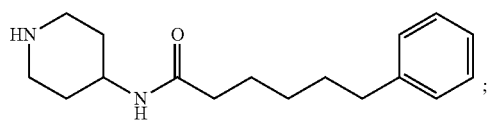

1-(4-phenylbutyl)-3-(piperidin-4-yl)urea

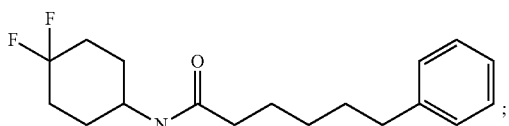

N-(4,4-difluorocyclohexyl)-6-phenylhexanamide

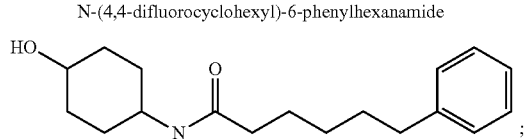

N-(4-hydroxycyclohexyl)-6-phenylhexanamide

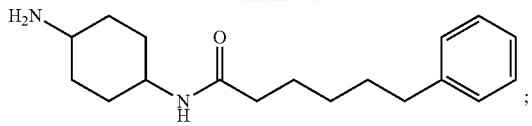

N-(4-aminocyclohexyl)-6-phenylhexanamide

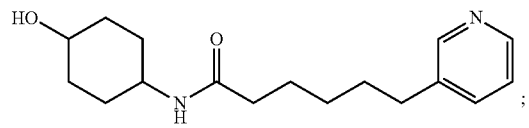

N-(4-hydroxycyclohexyl)-6-(pyridin-2-yl)hexanamide

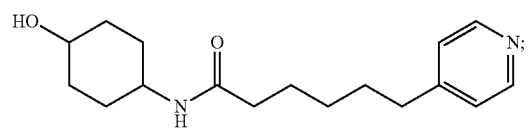

N-(4-hydroxycyclohexyl)-6-(pyridin-2-yl)hexanamide

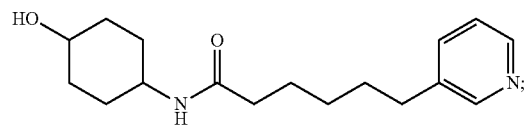

N-(4-hydroxycyclohexyl)-6-(pyridin-4-yl)hexanamide

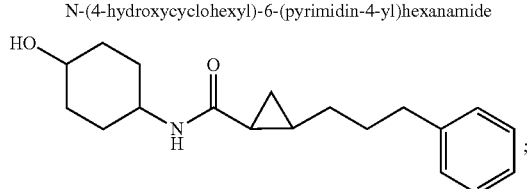

N-(4-hydroxycyclohexyl)-6-(pyrimidin-4-yl)hexanamide

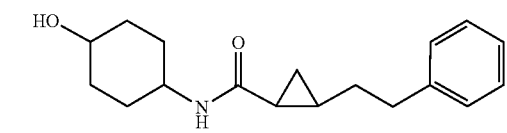

N-(4-hydroxycyclohexyl)-2-(3-phenylpropyl)
cyclyopropane-1-carboxamide

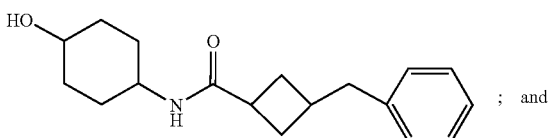

N-(4-hydroxycyclohexyl)-2-
(2-phenylthylcyclopropyl)acetamide

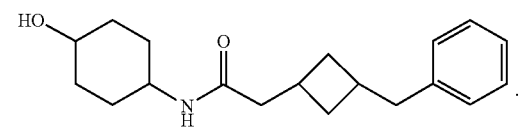

N-(4-hydroxycyclohexyl)-3-phenylthylcyclobutane-1-carboxamide; and

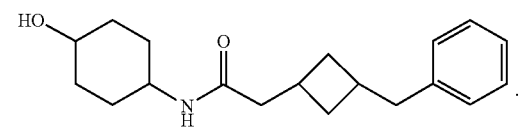

2-(3-benzylcyclobutyl)-N-(4-hydroxycyclohexyl)acetamide

Clause 6: The method of any of clauses 1 to 5, wherein the mitofusin activator is a compound of Formula III

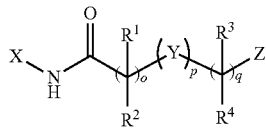

(III)

or a pharmaceutically salt thereof, wherein:

X is selected from cycloalkyl, heterocycloalkyl, aryl, and heteroaryl;

Z is selected from cycloalkyl, heterocycloalkyl, aryl, and heteroaryl;

$R^1$ and $R^2$ are independently selected from H, F, alkyl, and $C_{3-7}$ cycloalkyl; or $R^1$ and $R^2$ are taken together to form a $C_{3-7}$ cycloalkyl or heterocycloalkyl;

$R^3$ and $R^4$ are independently selected from H, F, alkyl, $COR^7$, $C_{3-7}$ cycloalkyl; or $R^3$ and $R^4$ are taken together to form a $C_{3-7}$ cycloalkyl or heterocycloalkyl;

Y is selected from O, $CR^5R^6$, $CR^7$=$CR^8$, a triple bond, cycloalkyl, heterocycloalkyl, aryl, heteroaryl, $NR^7$, S, $SO_2$, $SONR^8$, $-NR^8SO_2-$, $-NR^7CO-$, $-CONR^7-$, and $-NR^7CONR^8-$;

$R^5$ and $R^6$ are independently selected from H, F, alkyl, and cycloalkyl; or $R^5$ and $R^6$ are taken together to form $C_{3-7}$ cycloalkyl or heterocycloalkyl;

$R^7$ is selected from H, alkyl, and $C_{3-7}$ cycloalkyl;

$R^8$ is selected from H, alkyl, $COR^7$, and $C_{3-7}$ cycloalkyl;

o is 0, 1, 2, 3, 4, or 5;

p is 0 or 1; and q is 0, 1, 2, 3, 4, or 5, wherein when o is equal to or greater than 1, then Y=$NR^7$, S, $SO_2$, $SONR^8$, $-NR^8SO_2-$, $-NR^7CO-$, $-CONR^7-$, $-NR^7CONR^8-$, and wherein the sum of o+p+q is not less than 3 or greater than 7.

Clause 7: The mitofusin activator of clause 6 or a pharmaceutically acceptable salt thereof, wherein:

X is selected from cycloalkyl, and heterocycloalkyl;

Z is selected from cycloalkyl, heterocycloalkyl, aryl, and heteroaryl;

Y is selected from O, $CR^5R^6$, cycloalkyl, and aryl;

$R^1$, $R^2$, $R^3$, $R^4$, $R^5$, $R^6$, and $R^7$ are each independently selected from H and alkyl;

o is 0, 1, 2, 3, 4, or 5;

p is 0 or 1; and q is 0, 1, 2, 3, 4, or 5; and, wherein when o is equal to or greater than 1, then Y is S or $SO_2$; and wherein the sum of o+p+q is not less than 3 or greater than 7.

Clause 8: The mitofusin activator of clauses 6 or 7 or a pharmaceutically acceptable salt thereof, wherein:

X is selected from a cycloalkyl with having one, two, or three substituents independently selected from $R^7$, $OR^7$, $NR^7R^8$, fluorine, and $CF_3$; and a heterocycloalkyl containing one or two optionally substituted heteroatoms independently selected from O, $NR^7$, and S;

Z is selected from aryl and heteroaryl;

Y is selected from O, $CH_2$, and cycloalkyl;

$R^1$, $R^2$, $R^3$, and $R^4$ are each H;

$R^7$ is selected from H, alkyl, and $C_{3-7}$ cycloalkyl;

$R^8$ is selected from H, alkyl, and $C_{3-7}$ cycloalkyl;

o is 0, 1, 2, 3, 4, or 5;

p is 0 or 1; and q is 0, 1, 2, 3, 4, or 5; and, wherein when o is equal to or greater than 1, then Y is S or $SO_2$; and wherein the sum of o+p+q is not less than 3 or greater than 5.

Clause 9: The mitofusin activator of any of clauses 6 to 8, or a pharmaceutically acceptable salt thereof, wherein X is a cycloalkyl with one, two, or three substituents independently selected from the group consisting of $R^7$, $OR^7$, $NR^7R^8$, fluorine, and $CF_3$ or X is a heterocycloalkyl containing one or two optionally substituted heteroatoms independently selected from O, $NR^7$, and S;

Z is selected from aryl and heteroaryl;

Y is selected from cyclopropyl and cyclobutyl;

$R^1$, $R^2$, $R^3$, and $R^4$ are each H;

$R^7$ is selected from H, alkyl, and $C_{3-7}$ cycloalkyl; and $R^8$ is selected from H, alkyl, $COR^7$, and $C_{3-7}$ cycloalkyl; or $R^7$ and $R^8$ are taken together to form $C_{3-7}$ cyclolkyl;

o is 0, 1, 2, or 3;

p is 1; and q is 0, 1, 2, or 3, wherein the sum of o+p+q is not less than 3 or greater than 5.

Clause 10: The mitofusin activator of any of clauses 6 to 9 or a pharmaceutically acceptable salt thereof, wherein:

X is cycloalkyl with one, two, or three substituents independently selected from the group consisting of $R^7$, $OR^7$, $NR^7R^8$, fluorine, and $CF_3$ or X is heterocycloalkyl containing one or two optionally substituted heteroatoms independently selected from O, $NR^7$, and S;

Z is selected from aryl and heteroaryl;

Y is selected from O and $CH_2$;

$R^1$, $R^2$, $R^3$, and $R^4$ are each H;

$R^7$ and $R^8$ are independently selected from H, alkyl, and $C_{3-7}$ cycloalkyl; or $R^7$ and $R^8$ are taken together to form $C_{3-7}$ cyclolkyl;

o is 0, 1, 2, 3, or 4;

p is 1; and q is 0, 1, 2, 3, or 4, wherein the sum of o+p+q is 5.

Clause 11. The mitofusin activator of any of clauses 6 to 10 or a pharmaceutically acceptable salt thereof, wherein X is selected from 4-hydroxylcyclohexyl, 4-aminocyclohexyl, 4-(N-methyl)aminocyclohexyl, 4-(N,N-dimethyl)aminocyclohexyl, 4-(N-acetylamino)cyclohexyl, 4,4-difluorocyclohexyl, tetrahydropyranyl, tetrahydrothiopyranyl, piperidinyl, N-methyl-piperidinyl, and N-acetyl-piperidinyl;

Z is selected from aryl and heteroaryl;

Y is selected from O and $CH_2$;

$R^1$, $R^2$, $R^3$, and $R^4$ are each H;

o is 0, 1, 2, 3, or 4;

p is 1; and q is 0, 1, 2, 3, or 4; and, wherein the sum of o+p+q is 5.

Clause 12: The mitofusin activator of any of clauses 6 to 11 or a pharmaceutically acceptable salt thereof, wherein:

X is selected from cycloalkyl, heterocycloalkyl, aryl, and heteroaryl; each independently having has zero to four substituents independently selected from $R^7$, $OR^7$, Cl, F, $-CN$, $CF_3$, $-NR^7R^8$, $-SO_2NR^7R^8$, $-NR^7SO_2R^g$, $-SO_2R^g$, $-CONR^7R^8$, $-NR^7COR^g$, $C_{3-7}$ cycloalkyl, and heterocycloalkyl, wherein the heterocycloalkyl and heteroaryl independently include one to four heteroatoms selected from the group consisting of nitrogen, oxygen, and sulfur;

Z is selected from phenyl and heteroaryl; each having zero to four substituents independently selected from $R^7$, $OR^7$, Cl, F, $-CN$, $CF_3$, $-NR^7R^8$, $-SO_2NR^7R^8$, $-NR^7SO_2R^9$, $-SO_2R^9$, $-CONR^7R^8$, $-NR^7COR^9$, $C_{3-7}$ cycloalkyl, and heterocycloalkyl and wherein the heteroaryl contains one to four atoms independently selected from nitrogen, oxygen and sulfur, and wherein the phenyl or heterocyclic moiety;

Y is selected from O and CH$_2$;

R$^1$, R$^2$, R$^3$, and R$^4$ are each H;

R$^7$ is selected from H, alkyl, and C$_{3-7}$ cycloalkyl; and R$^8$ is selected from H, alkyl, COR$^7$, and C$_{3-7}$ cycloalkyl; or R$^7$ and R$^8$ are taken together to form C$_{3-7}$ cyclolkyl;

R$^9$ is selected from alkyl and C$_{3-7}$ cycloalkyl;

o is 0, 1, 2, 3, or 4;

p is 1;

q is 0, 1, 2, 3, or 4; and wherein the sum of o+p+q is 5.

Clause 13: The mitofusin activator of any of clauses 6 to 12 or a pharmaceutically acceptable salt thereof, wherein X is selected from 4-hydroxylcyclohexyl, 4-aminocyclohexyl, 4-(N-methyl)aminocyclohexyl, 4-(N,N-dimethyl)aminocyclohexyl, 4-(N-acetylamino)cyclohexyl, 4,4-difluorocyclohexyl, tetrahydropyranyl, tetrahydrothiopyranyl, piperidinyl, N-methyl-piperidinyl, and N-acetyl-piperidinyl;

Z is selected from phenyl and heteroaryl; wherein the heterocyclic moiety contains 1 to 3 atoms independently selected from nitrogen, oxygen and sulfur, and wherein the phenyl or heterocyclic moiety has O to 3 substituents independently selected from R$^7$, OR$^7$, Cl, F, —CN, CF$_3$, —NR$^7$R$^8$, —SO$_2$R$^9$, —CONR$^7$R$^8$, —NR$^7$COR$^9$, C$_{3-7}$ cycloalkyl, and heterocycloalkyl;

Y is selected from O and CH$_2$;

R$^1$, R$^2$, R$^3$, and R$^4$ are each H;

R$^7$ is selected from H, alkyl, and C$_{3-7}$ cycloalkyl; and R$^8$ is selected from H, alkyl, COR$^7$ and C$_{3-7}$ cycloalkyl; or R$^7$ and R$^8$ are taken together to form C$_{3-7}$ cyclolkyl;

R$^9$ is selected from alkyl and C$_{3-7}$ cycloalkyl;

o is 0, 1, 2, 3, or 4;

p is 1; and q is 0, 1, 2, 3, or 4, wherein the sum of o+p+q is 5.

Clause 14: The mitofusin activator of any of clauses 6 to 13 or a pharmaceutically acceptable salt thereof, wherein X is selected from 4-hydroxylcyclohexyl, 4-aminocyclohexyl, 4-(N-methyl)aminocyclohexyl, 4-(N,N-dimethyl)aminocyclohexyl, 4-(N-acetylamino)cyclohexyl, 4,4-difluorocyclohexyl, tetrahydropyranyl, tetrahydrothiopyranyl, piperidinyl, 4-N-methyl-piperidinyl, and 4-N-acetyl-piperidinyl;

Z is selected from phenyl, 2-pyridinyl, 3-pyridinyl, 4-pyridinyl, 6-pyrimidinyl, 5-pyrimidinyl, 4-pyrimidinyl, and 2-pyrimidinyl, wherein the phenyl, pyridinyl, and pyrimidinyl moiety has zero to two substituents independently selected from the group consisting of R$^7$, OR$^7$, Cl, F, —CN, CF$_3$, —NR$^7$R$^8$, —SO$_2$R$^9$, —CONR$^7$R$^8$, and —NR$^7$COR$^9$;

Y is O or CH$_2$;

R$^1$, R$^2$, R$^3$, and R$^4$ are each H;

R$^7$ is selected from H, alkyl, and C$_{3-7}$ cycloalkyl; and R$^8$ is selected from H, alkyl, COR$^7$, and C$_{3-7}$ cycloalkyl; or R$^7$ and R$^8$ are taken together to form C$_{3-7}$ cyclolkyl;

R$^9$ is selected from alkyl and C$_{3-7}$ cycloalkyl;

o is 0, 1, 2, 3, or 4;

p is 1; and q is 0, 1, 2, 3, or 4, wherein the sum of o+p+q is 5.

Clause 15: A method of treating a disease for which a mitofusin activator is indicated, the method comprising administering to a mammal in need thereof a therapeutically effective amount of a compound of Formula III

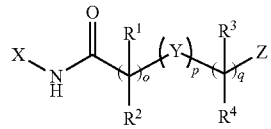

(III)

or a pharmaceutically salt thereof, wherein:

X is selected from cycloalkyl, heterocycloalkyl, aryl, and heteroaryl;

Z is selected from cycloalkyl, heterocycloalkyl, aryl, and heteroaryl;

R$^1$ and R$^2$ are independently selected from H, F, alkyl, and C$_{3-7}$ cycloalkyl; or R$^1$ and R$^2$ are taken together to form a C$_{3-7}$ cycloalkyl or heterocycloalkyl;

R$^3$ and R$^4$ are independently selected from H, F, alkyl, COR$^7$, and C$_{3-7}$ cycloalkyl or R$^3$ and R$^4$ are taken together to form a C$_{3-7}$ cycloalkyl or heterocycloalkyl;

Y is selected from O, CR$^5$R$^6$, CR$^7$=CR$^8$, a triple bond, cycloalkyl, heterocycloalkyl, aryl, heteroaryl, NR$^7$, S, SO$_2$, SONR$^8$, —NR$^8$SO$_2$—, —NR$^7$CO—, —CONR$^7$—, and —NR$^7$CONR$^8$—;

R$^5$ and R$^6$ are independently selected from H, F, alkyl, and cycloalkyl or R$^5$ and R$^6$ are taken together to form C$_{3-7}$ cycloalkyl or heterocycloalkyl;

R$^7$ is selected from H, alkyl, and C$_{3-7}$ cycloalkyl;

R$^8$ is selected from H, alkyl, COR$^7$, and C$_{3-7}$ cycloalkyl;

o is 0, 1, 2, 3, 4, or 5;

p is 0 or 1; and q is 0, 1, 2, 3, 4, or 5, wherein when o is equal to or greater than 1, then Y=NR$^7$, S, SO$_2$, SONR$^8$, —NR$^8$SO$_2$—, —NR$^7$CO—, —CONR$^7$—, —NR$^7$CONR$^8$—, and wherein the sum of o+p+q is not less than 3 or greater than 7.

Clause 16: The method of any of clauses 1 to 15, wherein the PNS or CNS disorder is selected from any one or a combination of:

a chronic neurodegenerative condition wherein mitochondrial fusion, fitness, or trafficking are impaired;

a disease or disorder associated with mitofusin 1 (MFN1) or mitofusin 2 (MFN2) dysfunction;

a disease associated with mitochondrial fragmentation, dysfunction, or dysmotility;

a degenerative neuromuscular condition such as Charcot-Marie-Tooth disease, Amyotrophic Lateral Sclerosis, Huntington's disease, Alzheimer's disease, Parkinson's disease;

hereditary motor and sensory neuropathy, autism, autosomal dominant optic atrophy (ADOA), muscular dystrophy, Lou Gehrig's disease, cancer, mitochondrial myopathy, diabetes mellitus and deafness (DAD), Leber's hereditary optic neuropathy (LHON), Leigh syndrome, subacute sclerosing encephalopathy, Neuropathy, ataxia, retinitis pigmentosa, and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), mtDNA depletion, mitochondrial neurogastrointestinal encephalomyopathy (MNGIE), dysautonomic mitochondrial myopathy, mitochondrial channelopathy, or pyruvate dehydrogenase complex deficiency (PDCD/PDH);

diabetic neuropathy;

chemotherapy-induced peripheral neuropathy; and/or crush injury, spinal cord injury (SCI), traumatic brain injury (TBI), stroke, optic nerve injury, and related conditions that involve axonal disconnection.

Clause 17: The method of any of clauses 1 to 16, with the proviso that the mitofusin activator is not selected from the following compounds:

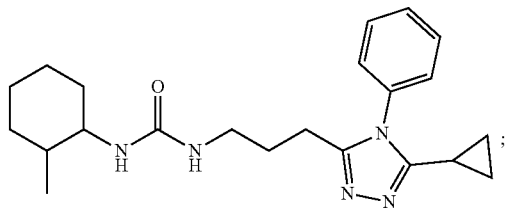

1-(3-(5-cyclopropyl-4-phenyl-4H-1,2,4-triazol-3-yl)propyl)-3-(2-methylcyclohexyl)urea

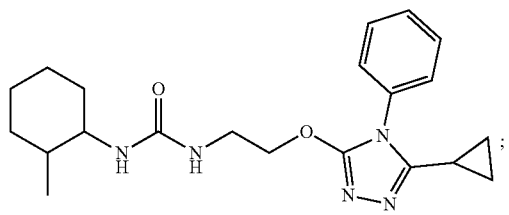

1-(2-((5-cyclopropyl-4-phenyl-4H-1,2,4-triazol-3-yl)oxy)ethyl)-3-(2-methylcyclohexyl)urea

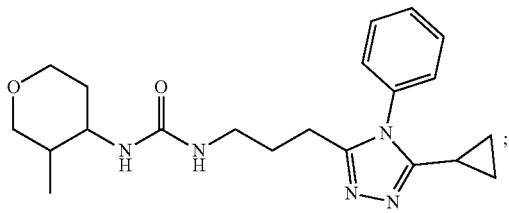

1-(3-(5-cyclopropyl-4-phenyl-4H-1,2,4-triazol-3-yl)propyl)-3-(tetrahydro-2H-pyran-4-yl)urea

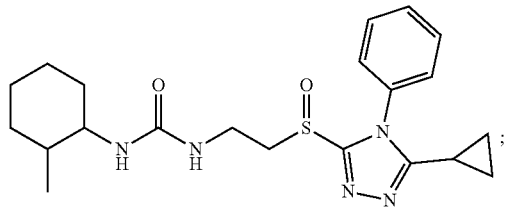

1-(2-((5-cyclopropyl-4-phenyl-4H-1,2,4-triazol-3-yl)sulfinyl)ethyl)-3-(2-methylcyclohexyl)urea

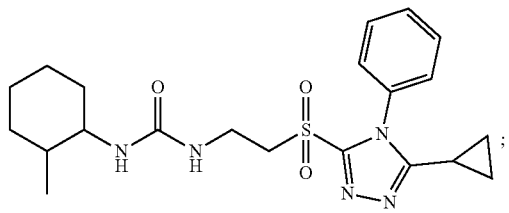

1-(2-(5-cyclopropyl-4-phenyl-4H-1,2,4-triazol-3-yl)sulfonyl)ethyl)-3-(2-methylcyclohexyl)urea

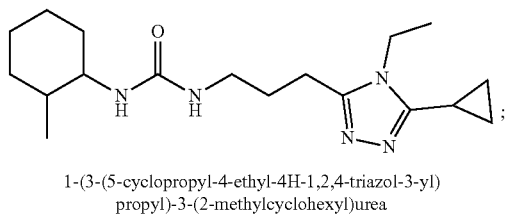

1-(3-(5-cyclopropyl-4-ethyl-4H-1,2,4-triazol-3-yl)propyl)-3-(2-methylcyclohexyl)urea -continued

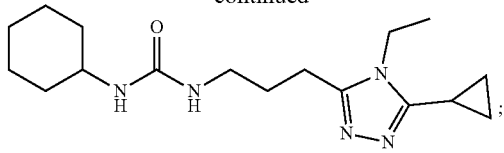

1-cyclohexyl-3-(3-(5-cyclopropyl)-4-ethyl-4H-1,2,4-triazol-3-yl)propyl)urea

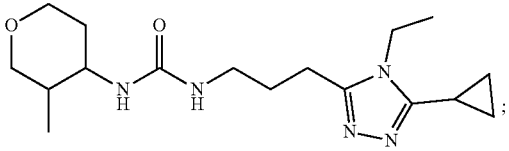

1-(3-(5-cyclopropyl-4-ethyl-4H-1,2,4-triazol-3-yl)propyl)-3-(methyltetrahydro-2H-pyran-4-yl)urea

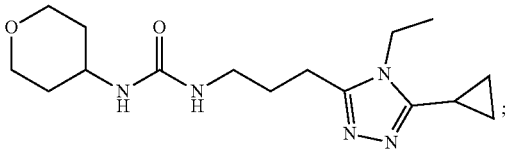

1-(3-(5-cyclopropyl-4-ethyl-4H-1,2,4-triazol-3-yl)propyl)-3-(tetrahydro-2H-pyran-4-yl)urea

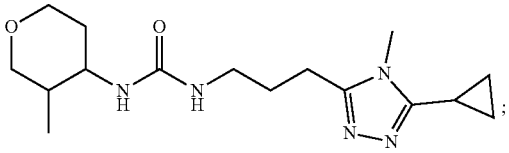

1-(3-(5-cyclopropyl-4-methyl-4H-1,2,4-triazol-3-yl)propyl)-3-(3-methyltetrahydro-2H-pyran-4-yl)urea

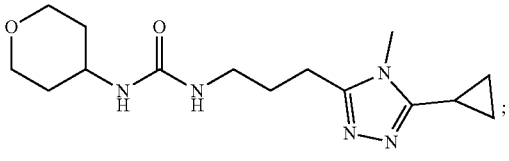

1-(3-(5-cyclopropyl-4-methyl-4H-1,2,4-triazol-3-yl)propyl)-3-(tetrahydro-2H-pyran-4-yl)urea

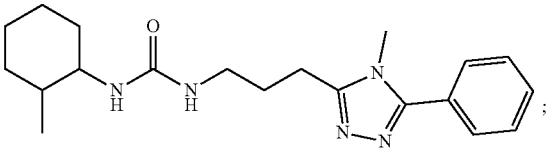

1-(3-(4-methyl-5-phenyl-4H-1,2,4-triazol-3-yl)propyl)-3-(2-methylcyclohexyl)urea

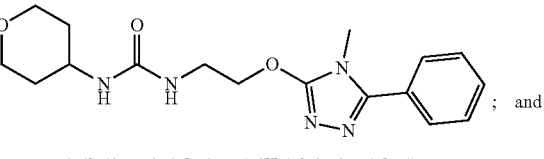

1-(3-(4-methyl-5-phenyl-4H-1,2,4-triazol-3-yl)propyl)-3-(tetrahydro-2H-pyran-4-yl)urea ; and

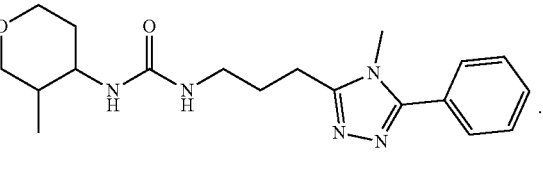

1-(3-(4-methyl-5-phenyl-4H-1,2,4-triazol-3-yl)propyl)-3-(3-methyltetrahydro-2H-pyran-4-yl)urea Clause 18: The method according to any of clauses 1 to 17, wherein the composition further comprises a pharmaceutically acceptable excipient.

Clause 19: A method of treating a CNS or PNS genetic or non-genetic neurodegenerative condition, injury, damage, or trauma comprising administering to the subject a therapeutically effective amount of a mitofusin activator of any one of clauses 2 to 18.

Clause 20: The method of clause 19, wherein the subject is diagnosed with or is suspected of having:

a chronic neurodegenerative condition wherein mitochondrial fusion, fitness, or trafficking are impaired;

a disease or disorder associated with mitofusin 1 (MFN1) or mitofusin 2 (MFN2) dysfunction;

a disease associated with mitochondrial fragmentation, dysfunction, or dysmotility;

a degenerative neuromuscular condition such as Charcot-Marie-Tooth disease, Amyotrophic Lateral Sclerosis, Huntington's disease, Alzheimer's disease, Parkinson's disease;

hereditary motor and sensory neuropathy, autism, autosomal dominant optic atrophy (ADOA), muscular dystrophy, Lou Gehrig's disease, cancer, mitochondrial myopathy, diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), mtDNA depletion, mitochondrial neurogastrointestinal encephalomyopathy (MNGIE), dysautonomic mitochondrial myopathy, mitochondrial channelopathy, or pyruvate dehydrogenase complex deficiency (PDCD/PDH);

diabetic neuropathy;

chemotherapy-induced peripheral neuropathy; and/or crush injury, spinal cord injury (SCI), traumatic brain injury (TBI), stroke, optic nerve injury, and related conditions that involve axonal disconnection.

Clause 21: A method of screening one or more candidate molecules for mitochondrial fusion modulatory activity comprising:

(i) constitutively expressing a mitochondrial-targeted photoswitchable fluorophore in cells expressing different combinations of MFN1 or MFN2 in a genetically defined manner;

(ii) photoswitching mitochondrial-targeted fluorophores in a micro-matrix pattern in cells transiently or constitutively expressing a mitochondrial-targeted photoswitchable fluorophore; and (iii) measuring merged/overlay fluorescence in photoswitched mitochondria.

Clause 22: The method of clause 21, further comprising comparing the merged/overlay fluorescence of the test mixture with the merged/overlay fluorescence of the control mixture, wherein when the merged/overlay fluorescence of the test mixture is greater than the merged/overlay fluorescence of the control mixture, the one or more candidate molecules in the test mixtures is identified as an activator of mitochondrial fusion.

Clause 23: The method of clause 21 or clause 22, further comprising comparing the merged/overlay fluorescence of the test mixture of a candidate agent in wild-type, MFN1, or MFN2 expressing cells with the merged/overlay fluorescence of that candidate agent in cells lacking both MFN1 and MFN2 (MFN null cells), wherein the merged/overlay fluorescence of the mixture in MFN expressing cells is greater than the merged/overlay fluorescence of the mixture in MFN null cells, the one or more candidate molecules in the test mixtures is identified as a mitofusin activator.

The present disclosure also relates to the following embodiments:

A. Methods for treating a mitochondria-associated disease, disorder or condition. The methods comprise: administering a therapeutically effective amount of a composition comprising one or more of a mitofusin activator or a pharmaceutically acceptable salt thereof to a subject having or suspected of having a mitochondria-associated disease, disorder or condition, the mitofusin activator having a formula of

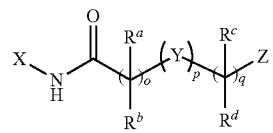

wherein:

X is selected from cycloalkyl and heterocycloalkyl,

Z is aryl;

$R^a$ and $R^b$ are independently selected from H, F, alkyl, and $C_{3-7}$ cycloalkyl, or $R^a$ and $R^b$ taken together form a $C_{3-7}$ cycloalkyl or heterocycloalkyl;

$R^c$ and $R^d$ are independently selected from H, F, alkyl, $COR^g$, and $C_{3-7}$ cycloalkyl, or $R^c$ and $R^d$ taken together form a $C_{3-7}$ cycloalkyl or heterocycloalkyl;

Y is selected from O, $CR^eR^f$, $CR^e=CR^f$, $C\equiv C$, cycloalkyl, heterocycloalkyl, aryl, heteroaryl, $NR^g$, S, $SO_2$, $SONR^h$, $NR^gSO_2$, $NR^gCO$, $CONR^g$, and $NR^gCONR^h$;

$R^e$ and $R^f$ are independently selected from H, F, alkyl, and cycloalkyl, or $R^e$ and $R^f$ taken together form $C_{3-7}$ cycloalkyl or heterocycloalkyl;

$R^g$ is selected from H, alkyl, and $C_{3-7}$ cycloalkyl;

$R^h$ is selected from H, alkyl, $COR^g$, and $C_{3-7}$ cycloalkyl;

o is 0, 1, 2, 3, 4, or 5;

p is 0 or 1; and q is 0, 1, 2, 3, 4, or 5, provided that if Y is cycloalkyl and p is 1, the sum of o+p+q is not less than 3 or greater than 5 and otherwise the sum of o+p+q is 5.

B. Compositions comprising a mitofusin activator or a pharmaceutically acceptable salt thereof. The compositions comprise: one or more of a mitofusin activator or a pharmaceutically acceptable salt thereof, the mitofusin activator having a formula of

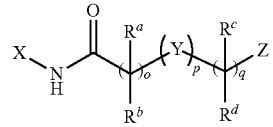

wherein:

X is selected from cycloalkyl and heterocycloalkyl,

Z is aryl;

$R^a$ and $R^b$ are independently selected from H, F, alkyl, and $C_{3-7}$ cycloalkyl, or $R^a$ and $R^b$ taken together form a $C_{3-7}$ cycloalkyl or heterocycloalkyl;

$R^c$ and $R^d$ are independently selected from H, F, alkyl, $COR^g$, and $C_{3-7}$ cycloalkyl, or $R^c$ and $R^d$ taken together form a $C_{3-7}$ cycloalkyl or heterocycloalkyl;

Y is selected from O, $CR^eR^f$, $CR^e=CR^f$, $C\equiv C$, cycloalkyl, heterocycloalkyl, aryl, heteroaryl, $NR^g$, S, $SO_2$, $SONR^h$, $NR^gSO_2$, $NR^gCO$, $CONR^g$, and $NR^gCONR^h$;

$R^e$ and $R^f$ are independently selected from H, F, alkyl, and cycloalkyl, or $R^e$ and $R^f$ taken together form $C_{3-7}$ cycloalkyl or heterocycloalkyl;

$R^g$ is selected from H, alkyl, and $C_{3-7}$ cycloalkyl;

$R^h$ is selected from H, alkyl, $COR^g$, and $C_{3-7}$ cycloalkyl;

o is 0, 1, 2, 3, 4, or 5;

p is 0 or 1; and q is 0, 1, 2, 3, 4, or 5, provided that if Y is cycloalkyl and p is 1, the sum of o+p+q is not less than 3 or greater than 5 and otherwise the sum of o+p+q is 5.

Embodiments A and B may include one or more of the following elements in any combination:

Element 1: wherein:
Y is selected from O, $CR^eR^f$, cycloalkyl, and aryl;
$R^a$, $R^b$, $R^c$, $R^d$, $R^e$, and $R^f$ are each independently selected from H and alkyl; and
p is 1.

Element 2: wherein:
X is selected from a cycloalkyl having one, two, or three substituents independently selected from the group consisting of $R^g$, $OR^g$, $NR^gR^h$, F, and $CF_3$, and a heterocycloalkyl containing one or two optionally substituted heteroatoms independently selected from O, $NR^g$, and S;
Y is selected from O, $CH_2$, and cycloalkyl;
$R^a$, $R^b$, $R^c$, and $R^d$ are each H;
$R^g$ is selected from H, alkyl, and $C_{3-7}$ cycloalkyl;
$R^h$ is selected from H, alkyl, and $C_{3-7}$ cycloalkyl; and p is 1.

Element 3: wherein:
X is selected from a cycloalkyl with one, two, or three substituents independently selected from the group consisting of $R^g$, $OR^g$, $NR^gR^h$, F, and $CF_3$, and a heterocycloalkyl containing one or two optionally substituted heteroatoms independently selected from O, $NR^g$, and S;
Y is selected from cyclopropyl and cyclobutyl;
$R^a$, $R^b$, $R^c$, and $R^d$ are each H;
$R^g$ is selected from H, alkyl, and $C_{3-7}$ cycloalkyl;
$R^h$ is selected from H, alkyl, $COR^g$, and $C_{3-7}$ cycloalkyl, or $R^g$ and $R^h$ taken together form a $C_{3-7}$ cycloalkyl;
o is 0, 1, 2, or 3;
p is 1; and
q is 0, 1, 2, or 3.

Element 4: wherein:
X is a cycloalkyl having one, two, or three substituents independently selected from the group consisting of $R^g$, $OR^g$, $NR^gR^h$, F, and $CF_3$, or X is a heterocycloalkyl containing one or two optionally substituted heteroatoms independently selected from O, $NR^g$, and S;
Y is selected from O and $CH_2$;
$R^a$, $R^b$, $R^c$, and $R^d$ are each H;
$R^g$ and $R^h$ are independently selected from H, alkyl, and $C_{3-7}$ cycloalkyl, or $R^g$ and $R^h$ taken together form $C_{3-7}$ cycloalkyl;
o is 0, 1, 2, 3, or 4;
p is 1; and
q is 0, 1, 2, 3, or 4.

Element 5: wherein X is selected from 4-hydroxycyclohexyl, 4-aminocyclohexyl, 4-(N-methyl)aminocyclohexyl, 4-(N,N-dimethyl)aminocyclohexyl, 4-(N-acetylamino)cyclohexyl, 4,4-difluorocyclohexyl, tetrahydropyranyl, tetrahydrothiopyranyl, piperidinyl, N-methyl-piperidinyl, and N-acetyl-piperidinyl.

Element 6: wherein x has zero to four substituents independently selected from $R^g$, $OR^g$, Cl, F, CN, $CF_3$, $NR^gR^h$, $SO_2NR^gR^h$, $NR^gSO_2R^i$, $SO_2R^i$, $CONR^gR^h$, $NR^gCOR^i$, $C_{3-7}$ cycloalkyl, and heterocycloalkyl, wherein the heterocycloalkyl includes one to four heteroatoms selected from the group consisting of nitrogen, oxygen, and sulfur;

Z is selected from phenyl having zero to four substituents independently selected from $R^g$, $OR^g$, Cl, F, CN, $CF_3$, $NR^gR^h$, $SO_2NR^gR^h$, $NR^gSO_2R^i$, $SO_2R^i$, $CONR^gR^h$, $NR^g$-$COR^i$, $C_{3-7}$ cycloalkyl, and heterocycloalkyl;

Y is selected from O and $CH_2$;

$R^a$, $R^b$, $R^c$, and $R^d$ are each H;

$R^g$ is selected from H, alkyl, and $C_{3-7}$ cycloalkyl, and $R^h$ is selected from H, alkyl, $COR^g$, and $C_{3-7}$ cycloalkyl, or $R^g$ and $R^h$ taken together form a $C_{3-7}$ cycloalkyl;

$R^i$ is selected from alkyl and $C_{3-7}$ cycloalkyl;

o is 0, 1, 2, 3, or 4;

p is 1; and q is 0, 1, 2, 3, or 4.

Element 7: wherein the mitofusin activator has a structure of

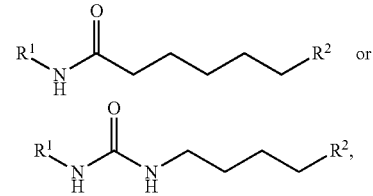

or a pharmaceutically acceptable salt, tautomer, or stereoisomer thereof, wherein $R^1$ is selected from unsubstituted, mono-substituted, or poly-substituted $C_{3-8}$ cycloalkyl and $C_{3-8}$ heterocycloalkyl; and wherein $R^2$ is aryl.

Element 8: wherein $R^1$ is selected from:

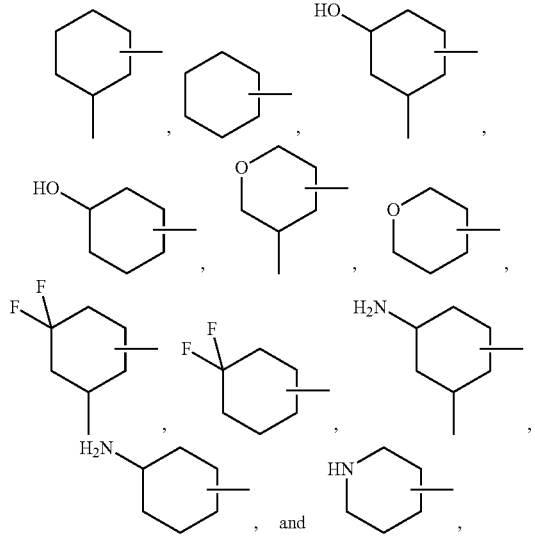

and wherein $R^2$ is selected from:

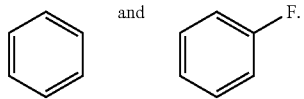 [SMILES: c1ccccc1 ; "and" ; Fc1ccccc1]

Element 9: wherein the mitofusin activator is selected from

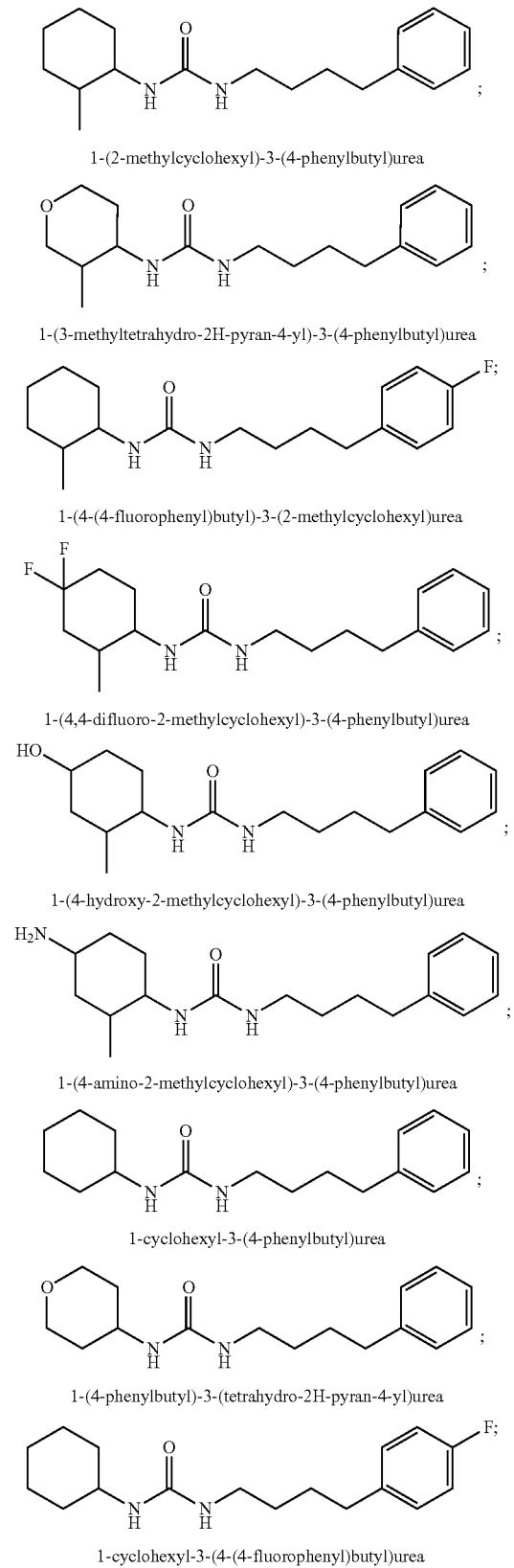

1-(2-methylcyclohexyl)-3-(4-phenylbutyl)urea 1-(3-methyltetrahydro-2H-pyran-4-yl)-3-(4-phenylbutyl)urea 1-(4-(4-fluorophenyl)butyl)-3-(2-methylcyclohexyl)urea 1-(4,4-difluoro-2-methylcyclohexyl)-3-(4-phenylbutyl)urea 1-(4-hydroxy-2-methylcyclohexyl)-3-(4-phenylbutyl)urea 1-(4-amino-2-methylcyclohexyl)-3-(4-phenylbutyl)urea 1-cyclohexyl-3-(4-phenylbutyl)urea 1-(4-phenylbutyl)-3-(tetrahydro-2H-pyran-4-yl)urea 1-cyclohexyl-3-(4-(4-fluorophenyl)butyl)urea

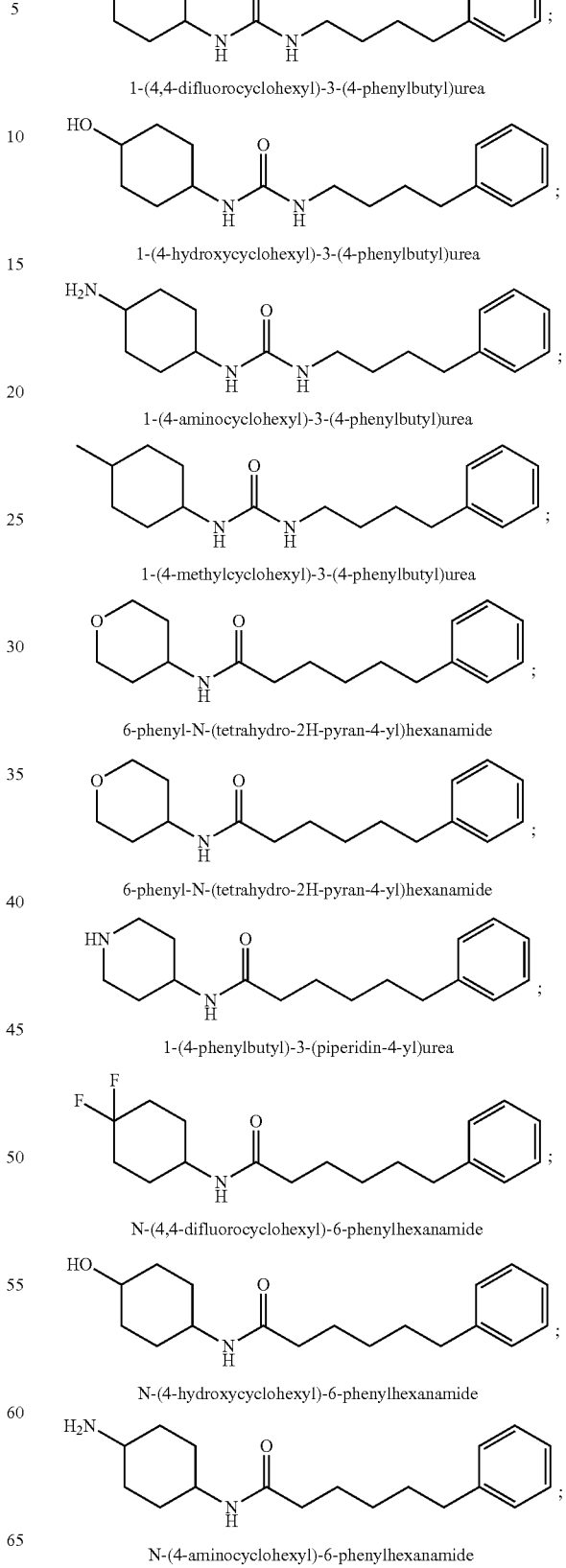

1-(4,4-difluorocyclohexyl)-3-(4-phenylbutyl)urea 1-(4-hydroxycyclohexyl)-3-(4-phenylbutyl)urea 1-(4-aminocyclohexyl)-3-(4-phenylbutyl)urea 1-(4-methylcyclohexyl)-3-(4-phenylbutyl)urea 6-phenyl-N-(tetrahydro-2H-pyran-4-yl)hexanamide 6-phenyl-N-(tetrahydro-2H-pyran-4-yl)hexanamide 1-(4-phenylbutyl)-3-(piperidin-4-yl)urea N-(4,4-difluorocyclohexyl)-6-phenylhexanamide N-(4-hydroxycyclohexyl)-6-phenylhexanamide N-(4-aminocyclohexyl)-6-phenylhexanamide

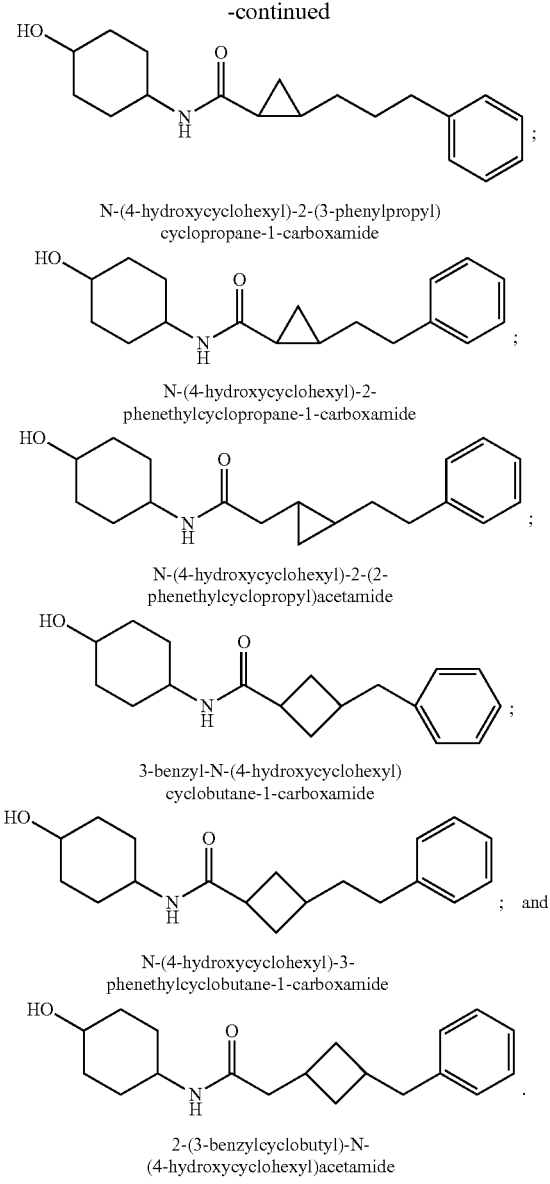

N-(4-hydroxycyclohexyl)-2-(3-phenylpropyl)cyclopropane-1-carboxamide

N-(4-hydroxycyclohexyl)-2-phenethylcyclopropane-1-carboxamide

N-(4-hydroxycyclohexyl)-2-(2-phenethylcyclopropyl)acetamide 3-benzyl-N-(4-hydroxycyclohexyl)cyclobutane-1-carboxamide N-(4-hydroxycyclohexyl)-3-phenethylcyclobutane-1-carboxamide 2-(3-benzylcyclobutyl)-N-(4-hydroxycyclohexyl)acetamide Element 10: wherein the mitochondria-associated disease, disorder or condition is a peripheral nervous system (PNS) or central nervous system (CNS) genetic or non-generic disorder, physical damage, and/or chemical injury.

Element 11: wherein the PNS or CNS disorder is selected from any one or a combination of:
a chronic neurodegenerative condition wherein mitochondrial fusion, fitness, or trafficking are impaired;
a disease or disorder associated with mitofusin 1 (MFN1) or mitofusin 2 (MFN2) dysfunction;
a disease associated with mitochondrial fragmentation, dysfunction, or dysmotility;
a degenerative neuromuscular condition such as Charcot-Marie-Tooth disease, Amyotrophic Lateral Sclerosis, Huntington's disease, Alzheimer's disease, Parkinson's disease;
hereditary motor and sensory neuropathy, autism, autosomal dominant optic atrophy (ADOA), muscular dystrophy, Lou Gehrig's disease, cancer, mitochondrial myopathy, diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (ME LAS), mtDNA depletion, mitochondrial neurogastrointestinal encephalomyopathy (MNGIE), dysautonomic mitochondrial myopathy, mitochondrial channelopathy, or pyruvate dehydrogenase complex deficiency (PDCD/PDH);
diabetic neuropathy;
chemotherapy-induced peripheral neuropathy; and
crush injury, spinal cord injury (SCI), traumatic brain injury, stroke, optic nerve injury, and related conditions that involve axonal disconnection.

Element 12: wherein the composition further comprises a pharmaceutically acceptable excipient.

Various changes could be made in the above methods without departing from the scope of the invention as defined in the claims below. It is intended that all matter contained in the above description, as shown in the accompanying drawings, shall be interpreted as illustrative and not as a limitation.

What is claimed is:
1. A method comprising:
administering a therapeutically effective amount of a composition comprising one or more of a mitofusin activator or a pharmaceutically acceptable salt thereof to a subject having or suspected of having a mitochondria-associated disease, disorder or condition, the mitofusin activator having a formula of

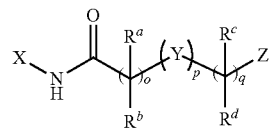

wherein:
X is

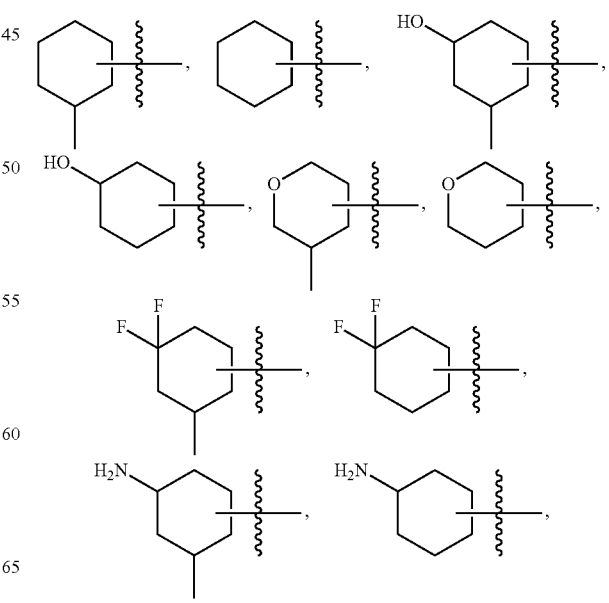

-continued

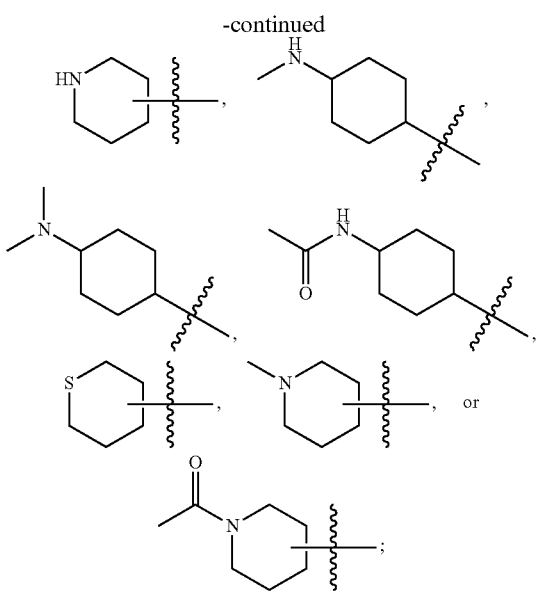

Z is optionally substituted phenyl;
$R^a$ and $R^b$ are independently H, F, alkyl, or $C_{3-7}$ cycloalkyl, or $R^a$ and $R^b$ taken together form a $C_{3-7}$ cycloalkyl or heterocycloalkyl;
$R^c$ and $R^d$ are independently H, F, alkyl, $COR^g$, or $C_{3-7}$ cycloalkyl, or $R^c$ and $R^d$ taken together form a $C_{3-7}$ cycloalkyl or heterocycloalkyl;
Y is O, $CH_2$, cyclopropyl, or cyclobutyl;
$R^g$ is H, alkyl, or $C_{3-7}$ cycloalkyl;
o is 0 or 1;
p is 1; and
q is 1, 2, 3, or 4, provided that if Y is cyclopropyl or cyclobutyl, the sum of o+p+q is not less than 3 or greater than 5 and otherwise the sum of o+p+q is 5.

2. The method of claim 1, wherein $R^a$, $R^b$, $R^c$, and $R^d$ are each independently H or alkyl.

3. The method of claim 2, wherein Y is $CH_2$, cyclopropyl or cyclobutyl.

4. The method of claim 2, wherein $R^a$, $R^b$, $R^c$, and $R^d$ are each H.

5. The method of claim 2, wherein X is

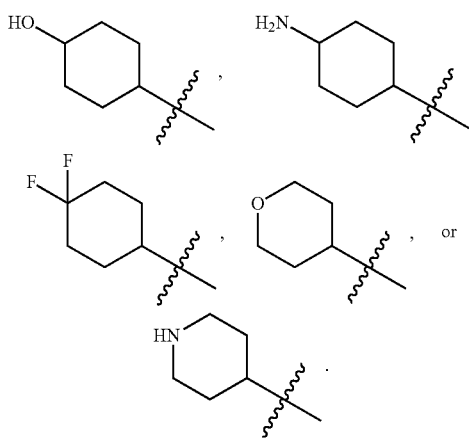

6. The method of claim 2, wherein Z is phenyl having zero to four substituents independently selected from the group consisting of $R^g$, $OR^g$, Cl, F, CN, $CF_3$, $NR^gR^h$, $SO_2NR^gR^h$, $NR^gSO_2R^i$, $SO_2R^i$, $CONR^gR^h$, $NR^gCOR^i$, $C_{3-7}$ cycloalkyl, and heterocycloalkyl;
$R^a$, $R^b$, $R^c$, and $R^d$ are each H;
$R^h$ is H, alkyl, $COR^g$, or $C_{3-7}$ cycloalkyl, or $R^g$ and $R^h$ taken together form a $C_{3-7}$ cycloalkyl; and
$R^i$ is from alkyl or $C_{3-7}$ cycloalkyl.

7. The method of claim 2, wherein the mitofusin activator has a structure of

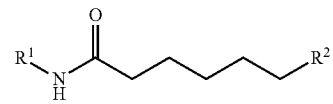

or a pharmaceutically acceptable salt, tautomer, or stereoisomer thereof,
wherein $R^1$ is X and $R^2$ is Z.

8. The method of claim 7, wherein $R^2$ is

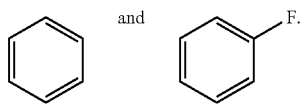

9. The method of claim 2, wherein the mitofusin activator is selected from the group consisting of

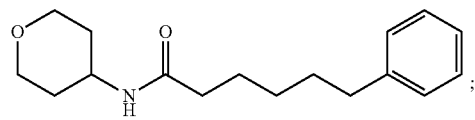
6-phenyl-N-(tetrahydro-2H-pyran-4-yl)hexanamide

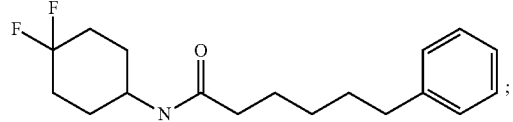
N-(4,4-difluorocyclohexyl)-6-phenylhexanamide

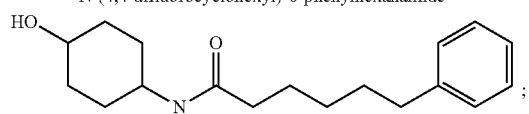
N-(4-hydroxycyclohexyl)-6-phenylhexanamide

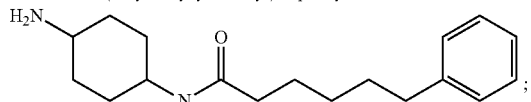
N-(4-aminocyclohexyl)-6-phenylhexanamide

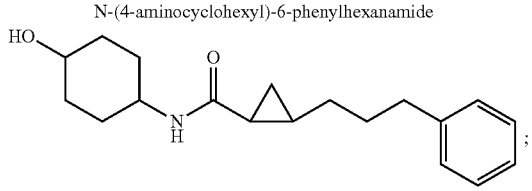
N-(4-hydroxycyclohexyl)-2-(3-phenylpropyl)cyclopropane-1-carboxamide

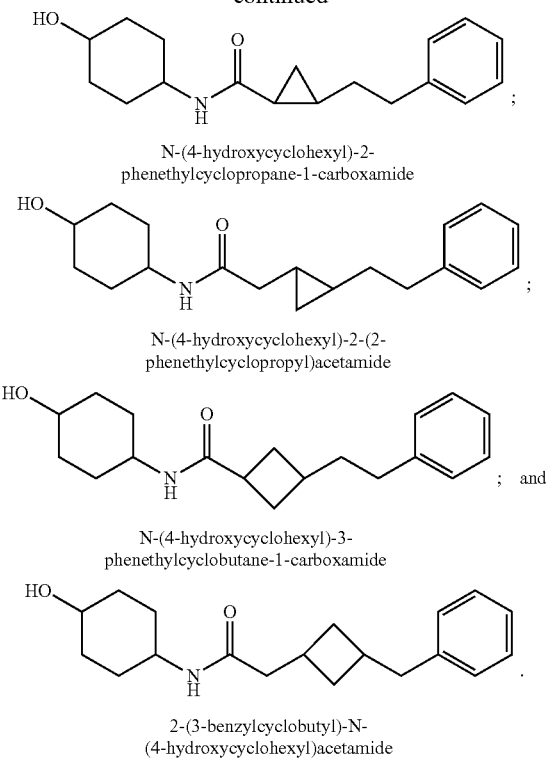

N-(4-hydroxycyclohexyl)-2-phenethylcyclopropane-1-carboxamide

N-(4-hydroxycyclohexyl)-2-(2-phenethylcyclopropyl)acetamide

N-(4-hydroxycyclohexyl)-3-phenethylcyclobutane-1-carboxamide 2-(3-benzylcyclobutyl)-N-(4-hydroxycyclohexyl)acetamide 10. The method of claim 1, wherein the mitochondria-associated disease, disorder or condition is a peripheral nervous system (PNS) or central nervous system (CNS) genetic or non-generic disorder, physical damage, and/or chemical injury.

11. The method of claim 10, wherein the PNS or CNS disorder is selected from any one or a combination of:
a chronic neurodegenerative condition wherein mitochondrial fusion, fitness, or trafficking are impaired;
a disease or disorder associated with mitofusin 1 (MFN1) or mitofusin 2 (MFN2) dysfunction;
a disease associated with mitochondrial fragmentation, dysfunction, or dysmotility;
a degenerative neuromuscular condition such as Charcot-Marie-Tooth disease, Amyotrophic Lateral Sclerosis, Huntington's disease, Alzheimer's disease, Parkinson's disease;
hereditary motor and sensory neuropathy, autism, autosomal dominant optic atrophy (ADOA), muscular dystrophy, Lou Gehrig's disease, cancer, mitochondrial myopathy, diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), mtDNA depletion, mitochondrial neurogastrointestinal encephalomyopathy (MNGIE), dysautonomic mitochondrial myopathy, mitochondrial channelopathy, or pyruvate dehydrogenase complex deficiency (PDCD/PDH);
diabetic neuropathy;
chemotherapy-induced peripheral neuropathy; and
crush injury, spinal cord injury (SCI), traumatic brain injury, stroke, optic nerve injury, and related conditions that involve axonal disconnection.

12. A composition comprising one or more of a mitofusin activator or a pharmaceutically acceptable salt thereof, the mitofusin activator having a formula of

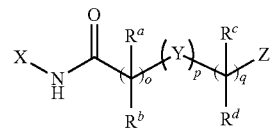

wherein:
X is

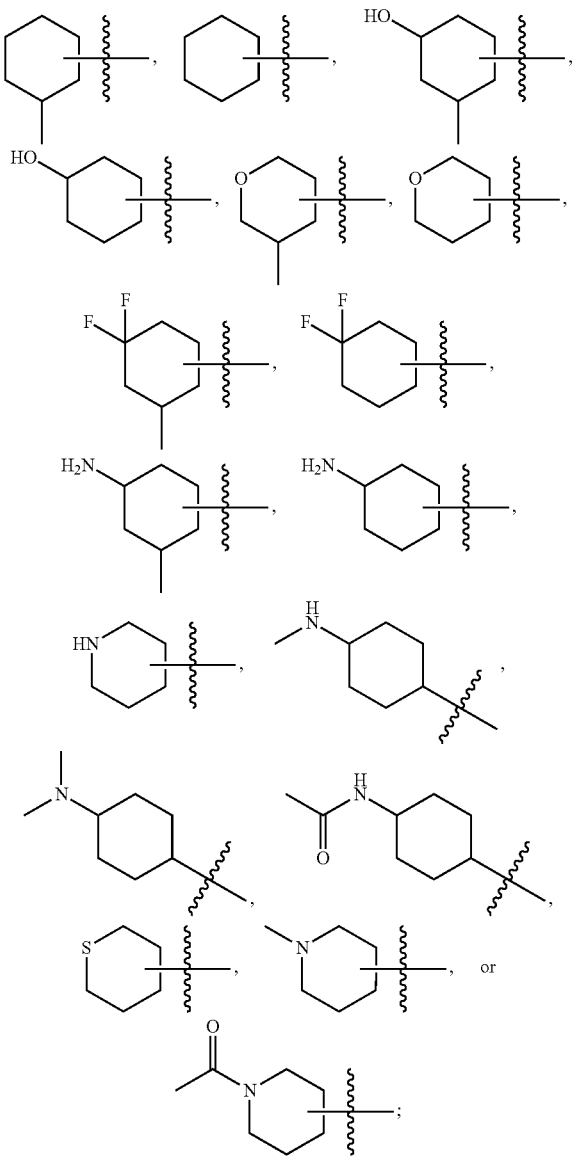

Z is optionally substituted phenyl;

$R^a$ and $R^b$ are independently H, F, alkyl, or $C_{3-7}$ cycloalkyl, or $R^a$ and $R^b$ taken together form a $C_{3-7}$ cycloalkyl or heterocycloalkyl;

$R^c$ and $R^d$ are independently H, F, alkyl, $COR^g$, or $C_{3-7}$ cycloalkyl, or $R^c$ and $R^d$ taken together form a $C_{3-7}$ cycloalkyl or heterocycloalkyl;

Y is O, $CH_2$, cyclopropyl or cyclobutyl;

$R^g$ is H, alkyl, or $C_{3-7}$ cycloalkyl;

o is 0 or 1;

p is 1; and q is 1, 2, 3, or 4, provided that if Y is cyclopropyl or cyclobutyl, the sum of o+p+q is not less than 3 or greater than 5 and otherwise the sum of o+p+q is 5.

13. The composition of claim 12, wherein $R^a$, $R^b$, $R^c$, and $R^d$ are each independently H or alkyl.

14. The composition of claim 13, wherein Y is $CH_2$, cyclopropyl or cyclobutyl.

15. The composition of claim 13, wherein $R^a$, $R^b$, $R^c$, and $R^d$ are each H.

16. The composition of claim 13, wherein X is

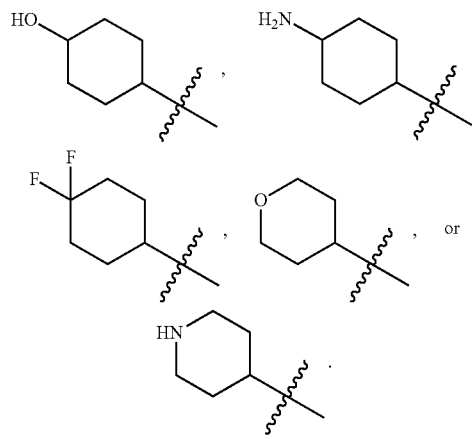

17. The composition of claim 13, wherein Z is phenyl having zero to four substituents independently selected from the group consisting of $R^g$, $OR^g$, Cl, F, CN, $CF_3$, $NR^gR^h$, $SO_2NR^gR^h$, $NR^gSO_2R^i$, $SO_2R^i$, $CONR^gR^h$, $NR^gCOR^i$, $C_{3-7}$ cycloalkyl, and heterocycloalkyl;

$R^a$, $R^b$, $R^c$, and $R^d$ are each H;

$R^h$ is H, alkyl, $COR^g$, or $C_{3-7}$ cycloalkyl, or $R^g$ and $R^h$ taken together form a $C_{3-7}$ cycloalkyl; and $R^i$ is alkyl or $C_{3-7}$ cycloalkyl.

18. The composition of claim 13, wherein the mitofusin activator has a structure of

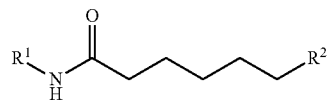

or a pharmaceutically acceptable salt, tautomer, or stereoisomer thereof, wherein $R^1$ is X and $R^2$ is Z.

19. The composition of claim 18, wherein $R^2$ is

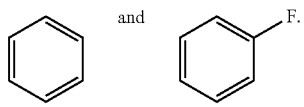 [SMILES: c1ccccc1 ; "and" ; Fc1ccccc1]

20. The composition of claim 13, wherein the mitofusin activator is selected from the group consisting of

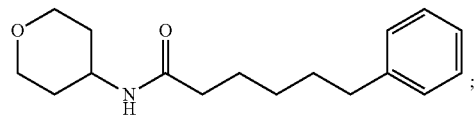

6-phenyl-N-(tetrahydro-2H-pyran-4-yl)hexanamide

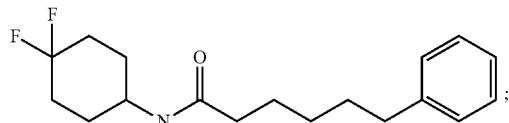

N-(4,4-difluorocyclohexyl)-6-phenylhexanamide

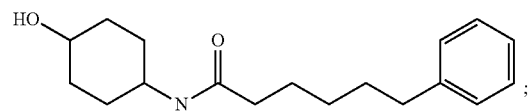

N-(4-hydroxycyclohexyl)-6-phenylhexanamide

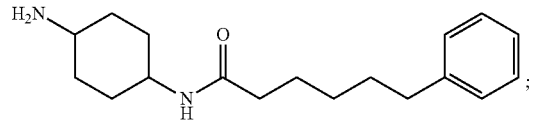

N-(4-aminocyclohexyl)-6-phenylhexanamide

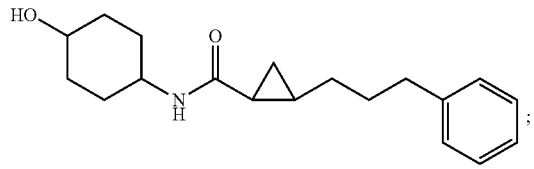

N-(4-hydroxycyclohexyl)-2-(3-phenylpropyl)cyclopropane-1-carboxamide

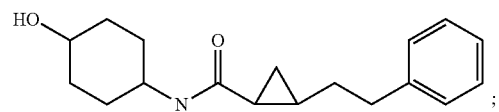

N-(4-hydroxycyclohexyl)-2-phenethylcyclopropane-1-carboxamide

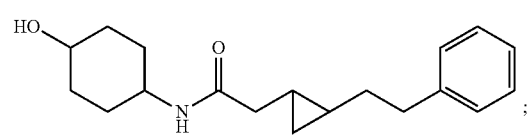

N-(4-hydroxycyclohexyl)-2-(2-phenethylcyclopropyl)acetamide

-continued
N-(4-hydroxycyclohexyl)-3-
phenethylcyclobutane-1-carboxamide
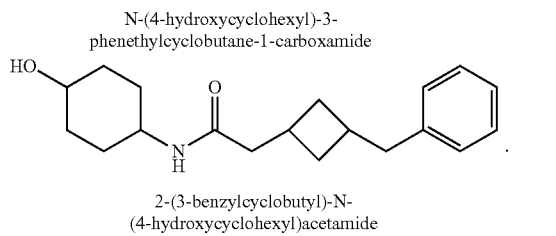
2-(3-benzylcyclobutyl)-N-
(4-hydroxycyclohexyl)acetamide
21. The composition of claim 13, further comprising: a pharmaceutically acceptable excipient.
* * * * *